US00RE42274E

(19) United States
(12) Reissued Patent
Kohn et al.

(10) Patent Number: US RE42,274 E
(45) Date of Reissued Patent: Apr. 5, 2011

(54) CYCLIC PEPTIDE CXCR4 ANTAGONISTS

(75) Inventors: Wayne David Kohn, Avon, IN (US); Sheng-Bin Peng, Carmel, IN (US); Liang Zeng Yan, Carmel, IN (US)

(73) Assignee: Eli Lilly and Company, Indianapolis, IN (US)

(21) Appl. No.: 12/807,694

(22) Filed: Sep. 10, 2010

Related U.S. Patent Documents

Reissue of:

(64) Patent No.: 7,691,813
Issued: Apr. 6, 2010
Appl. No.: 12/123,574
Filed: May 20, 2008

U.S. Applications:

(60) Provisional application No. 60/940,996, filed on May 31, 2007, provisional application No. 60/940,802, filed on May 30, 2007.

(51) Int. Cl.
*A61K 38/12* (2006.01)

(52) U.S. Cl. ..... 514/21.1

(58) Field of Classification Search ..... None
See application file for complete search history.

(56) References Cited

FOREIGN PATENT DOCUMENTS

| | | |
|---|---|---|
| JP | 2004 196769 | 7/2004 |
| WO | WO 2007/096662 | 8/2007 |

OTHER PUBLICATIONS

Tamamura et al. ("Development of Anti-HIV Agents Targeting Dynamic Supramolecular Mechanism: Entry and Fusion Inhibitors Based on CXCR4/CCR5 Antagonists and gp41-C34-Remodeling Peptides," Current HIV Research, 2005, 3, 289-301).*

Grande, et al., "Small Molecules Anti-HIV Therapeutics Targeting CXCR4," *Curr. Pharm. Design* 14:385-404 (2008).

Tamamura et al., "Development of Low Molecular Weight CXCR4 Antagonists by Exploratory Structural Tuning of Cyclic Tetra- and Pentapeptide-Scaffolds Towards the Treatment of HIV Infection, Cancer Metastasis and Rheumatoid Arthritis," *Curr. Med. Chem.* 14:93-102 (2007).

Tamamura, et al., "Development of Anti-HIV Agents Targeting Dynamic Supramolecular Mechanism: Entry and Fusion Inhibitors Based on CXCR4/CCR5 Antagonists and gp41-C34-Remodeling Peptides," *Curr. HIV Research* 3:289-301 (2005).

Ueda, et al., "Structure-Activity Relationships of Cyclic Peptide-Based Chemokine Receptor CXCR4 Antagonists: Disclosing the Importance of Side-Chain and Backbone Functionalities," *J. Med. Chem.* 50:192-198 (2007).

* cited by examiner

*Primary Examiner* — Christina Bradley
(74) *Attorney, Agent, or Firm* — Andrea M. Castetter

(57) ABSTRACT

Provided are lactam-cyclized peptide CXCR4 antagonists useful in the treatment of cancers, rheumatoid arthritis, pulmonary fibrosis, and HIV infection.

14 Claims, No Drawings

CYCLIC PEPTIDE CXCR4 ANTAGONISTS

Matter enclosed in heavy brackets [ ] appears in the original patent but forms no part of this reissue specification; matter printed in italics indicates the additions made by reissue.

*This application claims the priority of U.S. provisional patent application 60/940,802, filed 30 May 2007 and U.S. provisional patent application 60/940,996, filed 31 May, 2007.*

The present invention relates to novel cyclic peptide CXCR4 antagonist compounds and their use in treating diseases in which pathogenesis is mediated by CXCR4 and SDF-1.

CXCR4, a G-protein-coupled receptor, and its naturally occurring ligand, stromal cell-derived factor-1 (SDF-1; CXCL12), are a chemokine receptor-ligand pair. CXCR4 is constitutively- or over-expressed in a wide variety of human cancers. SDF-1, the only known ligand of CXCR4, is highly expressed in tumor microenvironments, as well as in bone marrow, lung, liver, and lymph nodes, i.e., organ sites most commonly involved in tumor metastasis. CXCR4/SDF-1 interaction plays important roles in multiple stages of tumorigenesis, including tumor growth, invasion, angiogenesis, and metastasis, as well as in rheumatoid arthritis, pulmonary fibrosis, and HIV infection (Tsutsumi et al. (2006) Peptide Science 88(2):279-289).

In view of the involvement of CXCR4/SDF-1 in these serious diseases, CXCR4 is an attractive therapeutic target.

AMD3100, a bicyclam CXCR4 antagonist, is currently in Phase III clinical trials for stem cell mobilization for transplantation of stem cells in patients with multiple myeloma and non-Hodgkins lymphoma. AMD070, another small molecule CXCR4 antagonist, is currently in Phase II clinical trials for HIV infection. CTCE9908, a bivalent (dimeric) peptide CXCR4 antagonist, is currently in Phase Ib/II clinical trials for cancer. FC131, a cyclic pentapeptide CXCR4 antagonist, inhibits $^{125}$I-SDF-1 binding to CXCR4 transfectants with an $IC_{50}$ of 4 nM (Fujii et al. (2003) Angew. Chem. Int. Ed 42:3251-3253; Araki et al. (2003) Peptide Science. The Japanese Peptide Society (2004):207-210).

There exists a need for improved CXCR4 antagonists that are potent and selective, exhibiting little or no activity at other chemokine receptors. The compounds of the present invention are such potent and selective CXCR4 antagonists. Their high potency permits the use of low doses in therapeutic regimens, while their high selectivity minimizes non-target related adverse side effects. In addition, compounds disclosed herein possess other highly desirable pharmacologic properties, such as high bioavailability when administered subcutaneously, good in vivo metabolic stability, and pharmacokinetic/pharmacodynamic properties that permit convenient dosing.

Accordingly, in a first aspect, the present invention provides a lactam-cyclized peptide of formula I:

(I) (SEQ ID NO: 1)

$R_1$-cyclo[$X_1$-Tyr-$X_3$-DArg-2Nal-Gly-$X_7$]-$X_8$-$X_9$-$X_{10}$-$R_2$ wherein:

a) said lactam is formed by an amide bond between the side chain amino group of $X_1$ and the side chain carboxyl group of $X_7$, wherein $X_1$ and $X_7$ are, respectively, a pair selected from the group consisting of (D/L)Agl/Glu, Dab/Glu, and Dap/Glu, and $R_1$ is Ac or n-hexanoyl; or b) said lactam is formed by an amide bond between the side chain carboxyl group of $X_1$ and the side chain amino group of $X_7$, wherein $X_1$ and $X_7$ are, respectively, a pair selected from the group consisting of Asp/(D/L)Agl, Asp/Dab, Asp/Dap, Glu/(D/L)Agl, Glu/Dab, Glu/Dap, Glu/DDap, and Glu/Lys, and $R_1$ is Ac or Bz, or wherein $X_1$ and $X_7$ are, respectively, a pair selected from the group consisting of succinyl/(D/L)Agl, succinyl/Dab, succinyl/Dap, succinyl/Lys, and succinyl/Orn, and $R_1$ is absent; or c) said lactam is formed by an amide bond between the α-amino group of $X_1$ and the side chain carboxyl group of $X_7$, wherein $X_1$ and $X_7$ are, respectively, a pair selected from the group consisting of Ala/Glu, Ala/DGlu, DAla/Glu, DAla/DGlu, Dap(Ac)/Glu, Gly/Asp, Gly/Glu, Gly/DGlu, Leu/Glu, Leu/DGlu, Lys/DGlu, Lys(Ac)/Glu, 2Nal/Glu, Phe/Glu, Phe/DGlu, DPhe/Glu, and DPhe/DGlu, and $R_1$ is absent; or d) said lactam is formed by an amide bond between a non-α, non-side-chain amino group of $X_1$ and the side chain carboxyl group of $X_7$, wherein $X_1$ and $X_7$ are, respectively, a pair selected from the group consisting of β-Ala/Asp, β-Ala/Glu, 5-amino-valeryl/Asp, 5-aminovaleryl/Glu, 4-AMB/Glu, 4-AMPA/Asp, and 4-AMPA/Glu, and $R_1$ is absent; or e) said lactam is formed by an amide bond between the α-amino group of $X_2$ and the side chain carboxyl group of $X_7$, wherein $X_2$ and $X_7$ are, respectively, a pair selected from the group consisting of Tyr/Asp, Tyr/Glu, and Tyr/DGlu, and $R_1$ and $X_1$ are each absent;

$R_1$ is a substituent on the α-amino group of $X_1$ when $X_1$ contains an α-amino group and said α-amino group is not a constituent of said lactam amide bond, selected from the group consisting of Ac, Bz, and n-hexanoyl, or is absent, wherein $X_1$ is selected from the group consisting of (D/L)Agl, Asp, Dab, Dap, and Glu;

$X_1$ is selected from the group consisting of (D/L)Agl, Ala, β-Ala, DAla, 5-aminovaleryl, 4-AMB, 4-AMPA, Asp, Dab, Dap, Dap(Ac), Glu, Gly, Leu, Lys, Lys(Ac), 2Nal, Phe, DPhe, and succinyl, or is absent;

$X_3$ is selected from the group consisting of Arg, Lys, Lys(iPr), and Lys($Me_2$);

$X_7$ is selected from the group consisting of (D/L)Agl, Asp, Dab, Dap, DDap, Glu, DGlu, Lys, and Orn;

$X_8$ is selected from the group consisting of β-Ala, Arg, DArg, Gly, Lys, Lys(iPr), and Orn, or is absent;

$X_9$ is selected from the group consisting of Gly, 2Nal, D2Nal, and DPhe, or is absent;

$X_{10}$ is 2Nal, or is absent;

wherein when $X_8$ is absent, $X_9$ and $X_{10}$ are each absent, and when $X_9$ is absent, $X_{10}$ is absent, and $R_2$ is selected from the group consisting of $NH_2$ and NHEt, or a pharmaceutically acceptable salt thereof.

Expressed alternatively, this is equivalent to a lactam-cyclized peptide of formula I:

(I) (SEQ ID NO: 1)

$R_1$-cyclo[$X_1$-Tyr-$X_3$-DArg-2Nal-Gly-$X_7$]-$X_8$-$X_9$-$X_{10}$-$R_2$ wherein:

$R_1$ is a substituent on the α-amino group of $X_1$ when $X_1$ contains an α-amino group and said α-amino group is not a constituent of said lactam amide bond, selected from the group consisting of Ac, Bz, and n-hexanoyl, or is absent, wherein $X_1$ is selected from the group consisting of (D/L)Agl, Asp, Dab, Dap, and Glu;

$X_1$ is selected from the group consisting of (D/L)Agl, Ala, β-Ala, DAla, 5-aminovaleryl, 4-AMB, 4-AMPA, Asp, Dab, Dap, Dap(Ac), Glu, Gly, Leu, Lys, Lys(Ac), 2Nal, Phe, DPhe, and succinyl, or is absent;

$X_3$ is selected from the group consisting of Arg, Lys, Lys (iPr), and Lys($Me_2$);

$X_7$ is selected from the group consisting of (D/L)Agl, Asp, Dab, Dap, DDap, Glu, DGlu, Lys, and Orn;

$X_8$ is selected from the group consisting of β-Ala, Arg, DArg, Gly, Lys, Lys(iPr), and Orn, or is absent;

$X_9$ is selected from the group consisting of Gly, 2Nal, D2Nal, and DPhe, or is absent;

$X_{10}$ is 2Nal, or is absent;

wherein when $X_8$ is absent, $X_9$ and $X_{10}$ are each absent, and when $X_9$ is absent, $X_{10}$ is absent, and $R_2$ is selected from the group consisting of $NH_2$ and NHEt, wherein:

a) said lactam is formed by an amide bond between the side chain amino group of $X_1$ and the side chain carboxyl group of $X_7$, when $X_1$ and $X_7$ are, respectively, a pair selected from the group consisting of (D/L)Agl/Glu, Dab/Glu, and Dap/Glu, and $R_1$ is Ac or n-hexanoyl; or b) said lactam is formed by an amide bond between the side chain carboxyl group of $X_1$ and the side chain amino group of $X_7$, when $X_1$ and $X_7$ are, respectively, a pair selected from the group consisting of Asp/(D/L)Agl, Asp/Dab, Asp/Dap, Glu/(D/L)Agl, Glu/Dab, Glu/Dap, Glu/DDap, and Glu/Lys, and $R_1$ is Ac or Bz, or when $X_1$ and $X_7$ are, respectively, a pair selected from the group consisting of succinyl/(D/L)Agl, succinyl/Dab, succinyl/Dap, succinyl/Lys, and succinyl/Orn, and $R_1$ is absent; or c) said lactam is formed by an amide bond between the α-amino group of $X_1$ and the side chain carboxyl group of $X_7$, when $X_1$ and $X_7$ are, respectively, a pair selected from the group consisting of Ala/Glu, Ala/DGlu, DAla/Glu, DAla/DGlu, Dap(Ac)/Glu, Gly/Asp, Gly/Glu, Gly/DGlu, Leu/Glu, Leu/DGlu, Lys/DGlu, Lys(Ac)/Glu, 2Nal/Glu, Phe/Glu, Phe/DGlu, DPhe/Glu, and DPhe/DGlu, and $R_1$ is absent; or d) said lactam is formed by an amide bond between a non-α, non-side-chain amino group of $X_1$ and the side chain carboxyl group of $X_7$, when $X_1$ and $X_7$ are, respectively, a pair selected from the group consisting of β-Ala/Asp, β-Ala/Glu, 5-amino-valeryl/Asp, 5-aminovaleryl/Glu, 4-AMB/Glu, 4-AMPA/Asp, and 4-AMPA/Glu, and $R_1$ is absent; or e) said lactam is formed by an amide bond between the α-amino group of $X_2$ and the side chain carboxyl group of $X_7$, when $X_2$ and $X_7$ are, respectively, a pair selected from the group consisting of Tyr/Asp, Tyr/Glu, and Tyr/DGlu, and $R_1$ and $X_1$ are each absent, or a pharmaceutically acceptable salt thereof.

In another aspect, the present invention provides a lactam-cyclized peptide of formula I:

(I) (SEQ ID NO: 1)

$R_1$-cyclo[$X_1$-Tyr-$X_3$-DArg-2Nal-Gly-$X_7$]-$X_8$-$X_9$-$X_{10}$-$R_2$ or a pharmaceutically acceptable salt thereof, wherein:

$X_1$ is selected from the group consisting of (D/L)Agl, Ala, β-Ala, DAla, 5-aminovaleryl, 4-AMB, 4-AMPA, Asp, Dab, Dap, Dap(Ac), Glu, Gly, Leu, Lys, Lys(Ac), 2Nal, Phe, DPhe, and succinyl, or is absent, wherein when $X_1$ is (D/L)Agl, Dab, or Dap and the α-amino group of $X_1$ is not a constituent of the lactam amide bond, said α-amino group is substituted with $R_1$ which is selected from the group consisting of Ac and n-hexanoyl;

wherein when $X_1$ is Asp or Glu and the α-amino group of $X_1$ is not a constituent of the lactam amide bond, said α-amino group is substituted with $R_1$ which is selected from the group consisting of Ac and Bz; and wherein when $X_1$ is Ala, β-Ala, DAla, 5-aminovaleryl, 4-AMB, 4-AMPA, Dap(Ac), Gly, Leu, Lys, Lys(Ac), 2Nal, Phe, DPhe or succinyl, $R_1$ is absent;

$X_3$ is selected from the group consisting of Arg, Lys, Lys (iPr), and Lys($Me_2$);

$X_7$ is selected from the group consisting of (D/L)Agl, Asp, Dab, Dap, DDap, Glu, DGlu, Lys, and Orn;

$X_8$ is selected from the group consisting of (D/L)-Ala, Arg, DArg, Gly, Lys, Lys(iPr), and Orn, or is absent;

$X_9$ is selected from the group consisting of Gly, 2Nal, D2Nal, and DPhe, or is absent;

$X_{10}$ is 2Nal, or is absent, wherein when $X_8$ is absent, $X_9$ and $X_{10}$ are each absent, and when $X_9$ is absent, $X_{10}$ is absent; and $R_2$ is selected from the group consisting of $NH_2$ and NHEt, and further wherein:

said lactam is formed by an amide bond between the side chain amino group of $X_1$ and the side chain carboxyl group of $X_7$, and $X_1$ and $X_7$ are, respectively, a pair selected from the group consisting of (D/L)Agl/Glu, Dab/Glu, and Dap/Glu, and $R_1$ is Ac or n-hexanoyl; or said lactam is formed by an amide bond between the side chain carboxyl group of $X_1$ and the side chain amino group of $X_7$, and $X_1$ and $X_7$ are, respectively, a pair selected from the group consisting of Asp/(D/L)Agl, Asp/Dab, Asp/Dap, Glu/(D/L)Agl, Glu/Dab, Glu/Dap, Glu/DDap, and Glu/Lys, and $R_1$ is Ac or Bz, or wherein $X_1$ and $X_7$ are, respectively, a pair selected from the group consisting of succinyl/(D/L)Agl, succinyl/Dab, succinyl/Dap, succinyl/Lys, and succinyl/Orn, and $R_1$ is absent; or said lactam is formed by an amide bond between the α-amino group of $X_1$ and the side chain carboxyl group of $X_7$, and $X_1$ and $X_7$ are, respectively, a pair selected from the group consisting of Ala/Glu, Ala/DGlu, DAla/Glu, DAla/DGlu, Dap(Ac)/Glu, Gly/Asp, Gly/Glu, Gly/DGlu, Leu/Glu, Leu/DGlu, Lys/DGlu, Lys(Ac)/Glu, 2Nal/Glu, Phe/Glu, Phe/DGlu, DPhe/Glu, and DPhe/DGlu, and $R_1$ is absent; or said lactam is formed by an amide bond between a non-α, non-side-chain amino group of $X_1$ and the side chain carboxyl group of $X_7$, and $X_1$ and $X_7$ are, respectively, a pair selected from the group consisting of β-Ala/Asp, β-Ala/Glu, 5-amino-valeryl/Asp, 5-aminovaleryl/Glu, 4-AMB/Glu, 4-AMPA/Asp, and 4-AMPA/Glu, and $R_1$ is absent; or said lactam is formed by an amide bond between the α-amino group of Tyr at $X_2$ and the side chain carboxyl group of $X_7$, and $X_7$ is selected from the group consisting of Asp, Glu, and DGlu, and $R_1$ and $X_1$ are each absent.

A recurrent sequence motif in all the compounds of formula I is the presence of Tyr at position $X_2$, DArg at position $X_4$, 2Nal at position $X_5$, and Gly at position $X_6$.

In another aspect, the present invention provides a lactam-cyclized peptide or pharmaceutically acceptable salt thereof of formula I (SEQ ID NO:1), wherein:

$R_1$ is selected from the group consisting of Ac and Bz, or is absent;

$X_1$ is selected from the group consisting of β-Ala, 4-AMB, 4-AMPA, Asp, Dab, Dap, Dap(Ac), Glu, 2Nal, Phe, and succinyl, or is absent;

$X_3$ is selected from the group consisting of Arg, Lys, Lys (iPr), and Lys($Me_2$);

$X_7$ is selected from the group consisting of Asp, Dab, Dap, Glu, DGlu, Lys, and Orn;

$X_8$ is selected from the group consisting of Arg and Lys, or is absent;

$X_9$ is absent;

$X_{10}$ is absent; and $R_2$ is selected from the group consisting of $NH_2$ and NHEt.

In another aspect, the present invention provides a lactam-cyclized peptide or pharmaceutically acceptable salt thereof of formula I (SEQ ID NO:1), wherein:

$R_1$ is selected from the group consisting of Ac and Bz, or is absent;

$X_1$ is selected from the group consisting of DAla, 5-aminovaleryl, 4-AMPA, Asp, Glu, Leu, Lys(Ac), Phe, DPhe, and succinyl;

$X_3$ is selected from the group consisting of Arg, Lys, Lys (iPr), and Lys($Me_2$);

$X_7$ is selected from the group consisting of (D/L)Agl, Asp, Dab, Dap, DDap, Glu, and DGlu;

$X_8$ is selected from the group consisting of Arg, DArg, and Lys, or is absent;

$X_9$ is absent;

$X_{10}$ is absent; and $R_2$ is selected from the group consisting of $NH_2$ and NHEt.

In another aspect, the present invention provides a lactam-cyclized peptide or pharmaceutically acceptable salt thereof of formula I (SEQ ID NO:1), wherein:

$R_1$ is selected from the group consisting of Ac, Bz, and n-hexanoyl, or is absent;

$X_1$ is selected from the group consisting of (D/L)Agl, Ala, β-Ala, Asp, Dap, Glu, Gly, Lys, and Phe;

$X_3$ is selected from the group consisting of Arg, Lys, Lys (iPr), and Lys($Me_2$);

$X_7$ is selected from the group consisting of (D/L)Agl, Asp, Dap, Glu, and DGlu;

$X_8$ is selected from the group consisting of β-Ala, Arg, Gly, Lys, Lys(iPr), and Orn, or is absent;

$X_9$ is selected from the group consisting of Gly, 2Nal, D2Nal, and DPhe, or is absent;

$X_{10}$ is 2Nal, or is absent; and $R_2$ is selected from the group consisting of $NH_2$ and NHEt.

In a further aspect, the present invention provides a lactam-cyclized peptide or pharmaceutically acceptable salt thereof of formula I (SEQ ID NO:1), wherein:

$R_1$ is selected from the group consisting of Ac and Bz, or is absent;

$X_1$ is selected from the group consisting of Ala, 5-aminovaleryl, Asp, Glu, Gly, Phe, DPhe, and succinyl;

$X_3$ is selected from the group consisting of Arg, Lys(iPr), and Lys($Me_2$);

$X_7$ is selected from the group consisting of (D/L)Agl, Asp, Dap, Glu, and DGlu;

$X_8$ is selected from the group consisting of β-Ala, Arg, Gly, Lys, Lys(iPr), and Orn, or is absent;

$X_9$ is selected from the group consisting of Gly, D2Nal, and DPhe, or is absent;

$X_{10}$ is 2Nal, or is absent; and $R_2$ is selected from the group consisting of $NH_2$ and NHEt.

In another aspect, the present invention provides a lactam-cyclized peptide or pharmaceutically acceptable salt thereof of formula I (SEQ ID NO:1), wherein:

$X_1$ is selected from the group consisting of Gly and Phe;

$X_3$ is Lys(iPr); and $X_7$ is DGlu.

In another aspect, the present invention provides a lactam-cyclized peptide or pharmaceutically acceptable salt thereof of formula I (SEQ ID NO:1), wherein:

$R_1$ is absent;

$X_1$ is selected from the group consisting of Gly and Phe;

$X_3$ is Lys(iPr);

$X_7$ is DGlu;

$X_8$ is selected from the group consisting of Arg and Lys (iPr), or is absent;

$X_9$ is absent;

$X_{10}$ is absent; and $R_2$ is selected from the group consisting of $NH_2$ and NHEt.

In another aspect, the present invention provides a lactam-cyclized peptide or pharmaceutically acceptable salt thereof of formula I (SEQ ID NO:1), wherein:

said lactam is formed by an amide bond between the side chain amino group of $X_1$ and the side chain carboxyl group of $X_7$;

$R_1$ is selected from the group consisting of Ac and n-hexanoyl;

$X_1$ is selected from the group consisting of (D/L)Agl, Dab, and Dap;

$X_3$ is selected from the group consisting of Arg and Lys (iPr);

$X_7$ is Glu;

$X_8$ is Arg;

$X_9$ is absent;

$X_{10}$ is absent; and $R_2$ is $NH_2$.

In a preferred embodiment of this aspect of the invention, $X_1$ is (D/L)Agl or Dap.

In another aspect, the present invention provides a lactam-cyclized peptide or pharmaceutically acceptable salt thereof of formula I (SEQ ID NO:1), wherein:

said lactam is formed by an amide bond between the side chain carboxyl group of $X_1$ and the side chain amino group of $X_7$;

$R_1$ is selected from the group consisting of Ac and Bz;

$X_1$ is selected from the group consisting of Asp and Glu;

$X_3$ is selected from the group consisting of Arg and Lys ($Me_2$);

$X_7$ is selected from the group consisting of (D/L)Agl, Dab, Dap, DDap, and Lys;

$X_8$ is Arg;

$X_9$ is absent;

$X_{10}$ is absent; and $R_2$ is $NH_2$.

In a preferred embodiment of this aspect of the invention, $X_7$ is (D/L)Agl, Dab, Dap, or DDap. In a more preferred embodiment, $X_7$ is (D/L)Agl or Dap.

In another aspect, the present invention provides a lactam-cyclized peptide or pharmaceutically acceptable salt thereof of formula I (SEQ ID NO:1), wherein:

said lactam is formed by an amide bond between the side chain carboxyl group of $X_1$ and the side chain amino group of $X_7$;

$R_1$ is absent;

$X_1$ is succinyl;

$X_3$ is Arg;

$X_7$ is selected from the group consisting of (D/L)Agl, Dab, Dap, Lys, and Orn;

$X_8$ is Arg;

$X_9$ is absent;

$X_{10}$ is absent; and $R_2$ is $NH_2$.

In a preferred embodiment of this aspect of the invention, $X_7$ is (D/L)Agl or Dap.

In another aspect, the present invention provides a lactam-cyclized peptide or pharmaceutically acceptable salt thereof of formula I (SEQ ID NO:1), wherein:

said lactam is formed by an amide bond between the α-amino group of $X_1$ and the side chain carboxyl group of $X_7$;

$R_1$ is absent;

$X_1$ is selected from the group consisting of Ala, DAla, Gly, Dap(Ac), Leu, Lys, Lys(Ac), 2Nal, Phe, and DPhe;

$X_3$ is selected from the group consisting of Arg, Lys, Lys (iPr), and Lys($Me_2$);

$X_7$ is selected from the group consisting of Asp, Glu, and DGlu;

$X_8$ is selected from the group consisting of β-Ala, Arg, Gly, Lys, Lys(iPr), and Orn, or is absent;

$X_9$ is selected from the group consisting of Gly, 2Nal, D2Nal, and DPhe, or is absent;

$X_{10}$ is 2Nal, or is absent;

wherein when $X_8$ is absent, $X_9$ and $X_{10}$ are each absent; and $R_2$ is selected from the group consisting of $NH_2$ and NHEt.

In a preferred embodiment of this aspect of the invention, $X_1$ is Ala, DAla, Gly, Leu, Lys, Lys(Ac), Phe, or DPhe. In a more preferred embodiment, $X_1$ is Ala, Gly, Lys, or Phe.

In a preferred embodiment of this aspect of the invention, $X_3$ is Arg, Lys, Lys(iPr), or Lys($Me_2$). In a more preferred embodiment, $X_3$ is Arg.

In a preferred embodiment of this aspect of the invention, $X_7$ is Asp, Glu, or DGlu. In a more preferred embodiment, $X_7$ is Asp.

In a preferred embodiment of this aspect of the invention, $X_8$ is β-Ala, Arg, Gly, Lys, Lys(iPr), Orn, or is absent. In a more preferred embodiment, $X_8$ is β-Ala, Gly, Lys, Lys(iPr), Orn, or is absent.

In a preferred embodiment of this aspect of the invention, $X_9$ is Gly, 2Nal, D2Nal, DPhe, or is absent. In a more preferred embodiment, $X_9$ is Gly, 2Nal, D2Nal, or DPhe.

In a preferred embodiment of this aspect of the invention, $X_{10}$ is 2Nal, or is absent. In a more preferred embodiment, $X_{10}$ is 2Nal.

In a preferred embodiment of this aspect of the invention, $R_2$ is NHEt.

In another aspect, the present invention provides a lactam-cyclized peptide or pharmaceutically acceptable salt thereof of formula I (SEQ ID NO:1), wherein:

said lactam is formed by an amide bond between a non-α, non-side-chain amino group of $X_1$ and the side chain carboxyl group of $X_7$;

$R_1$ is absent;

$X_1$ is selected from the group consisting of β-Ala, 4-AMB, 5-aminovaleryl, and 4-AMPA;

$X_3$ is Arg;

$X_7$ is selected from the group consisting of Asp and Glu;

$X_8$ is selected from the group consisting of Arg and DArg;

$X_9$ is absent;

$X_{10}$ is absent; and $R_2$ is $NH_2$.

In a preferred embodiment of this aspect of the invention, $X_1$ is β-Ala, 5-amino-valeryl, or 4-AMPA. In a more preferred embodiment, $X_1$ is β-Ala.

In a preferred embodiment of this aspect of the invention, $X_7$ is Asp.

In a preferred embodiment of this aspect of the invention, $X_8$ is Arg.

In another aspect, the present invention provides a lactam-cyclized peptide or pharmaceutically acceptable salt thereof of formula I (SEQ ID NO:1), wherein:

said lactam is formed by an amide bond between the α-amino group of $X_2$ and the side chain carboxyl group of $X_7$;

$R_1$ is absent;

$X_1$ is absent;

$X_3$ is Arg;

$X_7$ is selected from the group consisting of Asp, Glu, and DGlu;

$X_8$ is Arg;

$X_9$ is absent;

$X_{10}$ is absent; and $R_2$ is $NH_2$.

In another aspect, the present invention provides a lactam-cyclized peptide of the formula:

(SEQ ID NO: 70)

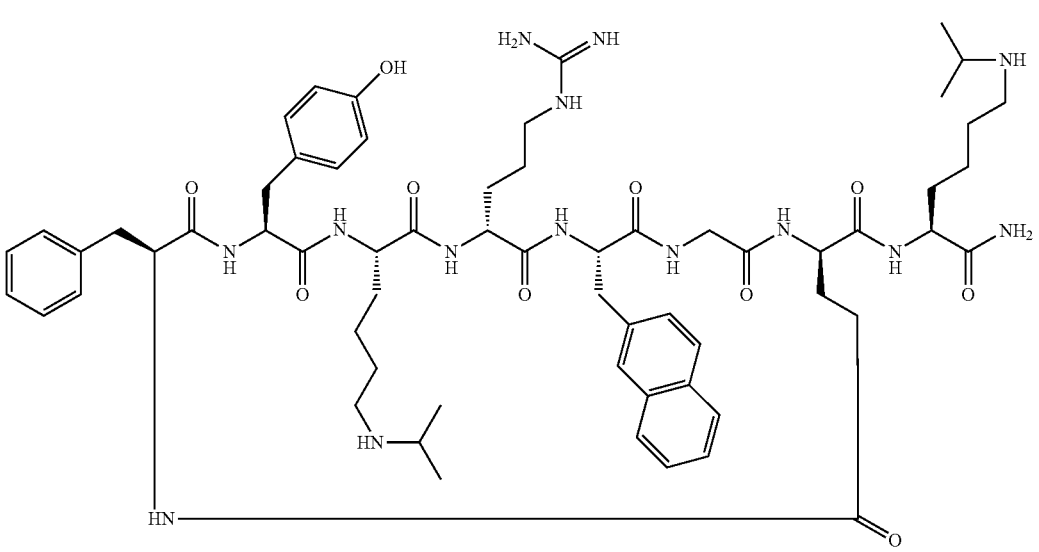

or a pharmaceutically acceptable salt thereof. The lactam is formed by an amide bond between the α-amino group of Phe and the side chain carboxyl group of DGlu. The pharmaceutically acceptable salt can be an acetic acid salt.

In another aspect, the present invention provides a pharmaceutical composition, comprising a lactam-cyclized peptide or pharmaceutically acceptable salt thereof as variously described above, and a pharmaceutically acceptable carrier, diluent, or excipient.

In another aspect, the present invention provides a lactam-cyclized peptide or pharmaceutically acceptable salt thereof as variously described above, for use in therapy.

In another aspect, the present invention provides a lactam-cyclized peptide or pharmaceutically acceptable salt thereof as variously described above, for the treatment of rheumatoid arthritis, pulmonary fibrosis, HIV infection, or a cancer selected from the group consisting of breast cancer, pancreatic cancer, melanoma, prostate cancer, kidney cancer, neuroblastoma, non-Hodgkin's lymphoma, lung cancer, ovarian cancer, colorectal cancer, multiple myeloma, glioblastoma multiforme, and chronic lymphocytic leukemia.

In another aspect, the present invention provides the use of a lactam-cyclized peptide or pharmaceutically acceptable salt thereof as variously described above, for the manufacture of a medicament for the treatment of rheumatoid arthritis, pulmonary fibrosis, HIV infection, or a cancer selected from the group consisting of breast cancer, pancreatic cancer, melanoma, prostate cancer, kidney cancer, neuroblastoma, non-Hodgkin's lymphoma, lung cancer, ovarian cancer, colorectal cancer, multiple myeloma, glioblastoma multiforme, and chronic lymphocytic leukemia.

In another aspect, the present invention provides a method of treating rheumatoid arthritis, pulmonary fibrosis, HIV infection, or a cancer selected from the group consisting of breast cancer, pancreatic cancer, melanoma, prostate cancer, kidney cancer, neuroblastoma, non-Hodgkin's lymphoma, lung cancer, ovarian cancer, colorectal cancer, multiple myeloma, glioblastoma multiforme, and chronic lymphocytic leukemia, comprising administering to a patient in need thereof an effective amount of a lactam-cyclized peptide or pharmaceutically acceptable salt thereof as variously described above.

In the macrocyclic peptidic compounds of the present invention (SEQ ID NO:1), amino acids $X_1$ through $X_{10}$ are referred to herein by their commonly employed three letter symbols, shown left to right from amino-terminal end to carboxy-terminal end. D- and L-(small capital letters) refer to absolute stereochemistry. Where neither designation is indicated in a particular formula, the L-form of the amino acid is present. $X_1$ can also be a dicarboxylic acid residue, i.e., a succinyl group. Amino acid or carboxylic acid residues within the brackets "[ ]" are within the cyclic structure; groups external to the brackets are outside the cyclized ring. In all cases, cyclization is via a lactam (amide) bond between $X_1$ (or $X_2$, i.e., Tyr) and $X_7$, which can be formed in several different ways, depending on the structures of $X_1$, $X_2$, and $X_7$.

When the lactam bond is formed between the side chain amino group of $X_1$ and the side chain carboxyl group of $X_7$ (Schemes 1 and 2; Examples 1-5), the α-amino group of $X_1$ is capped with Ac or n-hexanoyl.

When the lactam bond is formed between the side chain carboxyl group of $X_1$ and the side chain amino group of $X_7$, the α-amino group of $X_1$ is capped with Ac or Bz (Schemes 3 and 4; Examples 6-19). $X_1$ also can be a bifunctional residue other than an α-amino acid, for example one with two carboxyl groups, i.e., a succinyl residue. In this case, one carboxyl group forms an amide bond with the α-amino group of Tyr, and the other forms the cyclic lactam structure through an amide bond with the side chain amino group of $X_7$ (Schemes 3 and 4; Examples 20-24). When $X_1$ is succinyl, $R_1$ is absent.

In most of the lactam-cyclized peptides disclosed herein (Schemes 5-15; Examples 25-28, 32-66, and 75-89), the α-amino group of $X_1$ forms the lactam structure via an amide bond with the side chain carboxyl group of $X_7$, and $R_1$ is absent. Also included in the synthetic schemes of this category are cyclic peptides containing $X_1$ residues, i.e., β-Ala, 4-AMB, 5-aminovaleryl, and 4-AMPA, wherein the amino group is a non-side chain, non-α-amino group (Schemes 5 and 6; Examples 67-74). $R_1$ is also absent in these cases.

When both $R_1$ and $X_1$ are absent, the lactam structure is formed through an amide bond between the α-amino group of Tyr ($X_2$) and the side chain carboxyl group of $X_7$ (Schemes 5 and 6; Examples 29-31).

Structures of common amino acids, e.g., alanine, glycine, etc., are well known in the art. Structures of non-standard and substituted amino acids present in the instant invention compounds are shown below.

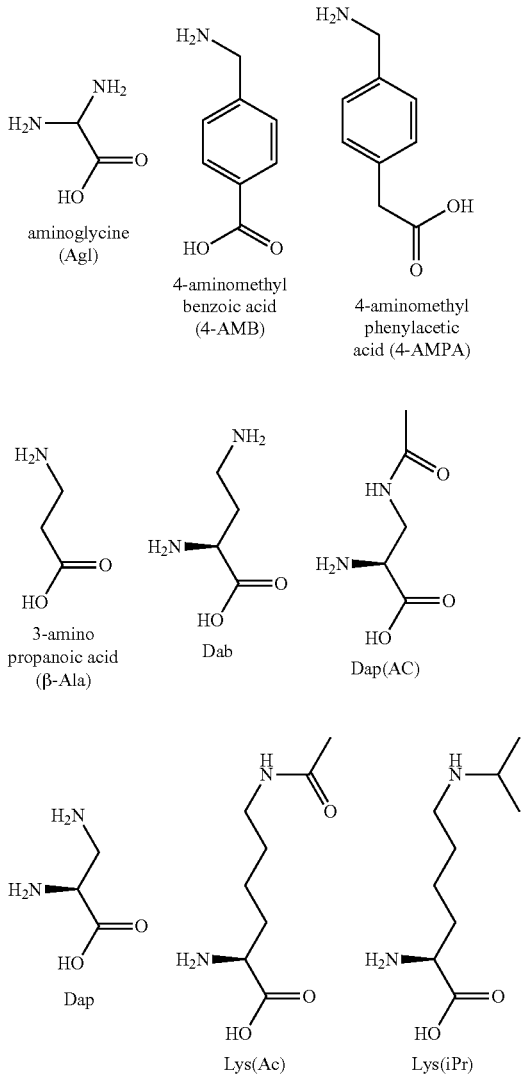

-continued

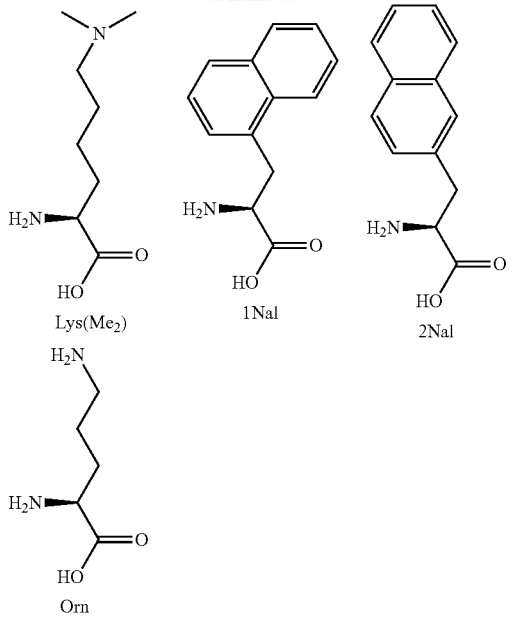

The lactam-cyclized peptides of the present invention can be prepared as pharmaceutically acceptable salts. Such salts, and common methodology for preparing them, are well known in the art. See, e.g., P. Stahl et al. (2002) Handbook of Pharmaceutical Salts Properties, Selection and Use, VCHA/Wiley-VCH; Berge et al. (1977) "Pharmaceutical Salts," Journal of Pharmaceutical Sciences 66(1): 1-19.

The compounds of the present invention are potent antagonists of CXCR4/SDF-1 interaction. Compounds of formula (I) and their pharmaceutically acceptable salts specifically exemplified herein exhibit an average $K_i$ value of about 7.5 nM or less as determined by the CXCR4/$^{125}$I-SDF-1α binding assay described below. More preferred compounds of formula (I) and their pharmaceutically acceptable salts exhibit an average $K_i$ value in the range of from about 0.2 nM to about 1 nM in this assay. Especially preferred compounds of formula (I) and their pharmaceutically acceptable salts exhibit an average $K_i$ value less than about 0.2 nM in this assay.

In addition, the compounds and pharmaceutically acceptable salts of the present invention are preferably highly selective for the CXCR4 receptor, exhibiting little or no inhibitory activity against other chemokine receptors, including CCR1, CCR2, CXCR2, CXCR3, and other G-protein coupled receptors at the concentrations tested, and no significant activity against serotonin, dopamine, and opioid receptors. They also preferably exhibit good stability in blood and plasma, good subcutaneous bioavailability, desirable pharmacokinetic/pharmacodynamic properties, and potent in vivo efficacy in tumor growth inhibition, with a wide safety margin.

In view of these pharmacological properties, the compounds of the present invention are indicated for the treatment of disorders involving CXCR4/SDF-1 interaction, or receptor activity activity of CXCR4, such as in HIV infection. In particular, the present compounds are useful in treating malignancies in which angiogenic, growth, survival, and metastatic pathways mediated by CXCR4 and SDF-1 are implicated in pathogenesis, including breast cancer, pancreatic cancer, melanoma, prostate cancer, kidney cancer, neuroblastoma, non-Hodgkin's lymphoma, lung cancer, ovarian cancer, colorectal cancer, multiple myeloma, glioblastoma multiforme, and chronic lymphocytic leukemia, as well as in rheumatoid arthritis, pulmonary fibrosis, and HIV infection (Tsutsumi et al. (2006) Peptide Science 88(2):279-289).

Agl (aminoglycine) is a pro-chiral building block. When this residue appears in a peptide formula herein, the α-carbon becomes a chiral center at which the two associated α-amino groups are each individually bonded to different moieties. In this case, the final peptide product contains two diastereomers that are unresolved, and that may be present in other than a 1:1 ratio. "(D/L)Agl" in a peptide formula denotes such a mixture of diastereomers. "(DL)Agl" denotes an Agl derivative that is racemic, for example Fmoc-(DL)Agl(Boc).

"$K_i$" values are calculated using $IC_{50}$ values determined in the CXCR4/$^{125}$I-SDF-1α binding assay described below by employing equation 7.22 of Enzymes, A Practical Introduction to Structure, Mechanism, and Data Analysis, Robert A. Copeland, Wiley-VCH, New York, 1996, page 207.

The term "SDF-1" includes two isoforms, SDF-1α and SDF-1β, currently understood to exhibit similar functionality.

"Treatment" as used herein refers to curative treatment of disorders associated with CXCR4/SDF-1 interaction or CXCR4 receptor activity. Curative treatment refers to processes involving a slowing, interrupting, arresting, controlling, or stopping of disease progression, but does not necessarily involve a total elimination of all disease-related symptoms, conditions, or disorders.

The compounds of the present invention can be used as medicaments in human or veterinary medicine, administered by a variety of routes. Most preferably, such compositions are for parenteral administration. Such pharmaceutical compositions can be prepared by methods well known in the art. See, e.g., Remington: The Science and Practice of Pharmacy, 19$^{th}$ ed. (1995), A. Gennaro et al., Mack Publishing Co., and comprise one or more compounds of formula (I) or a pharmaceutically acceptable salt(s) thereof, and a pharmaceutically acceptable carrier, diluent, or excipient.

The effective amount of the present compounds is in the range of from about 1 mg to about 300 mg, more preferably from about 1 mg to about 200 mg, more preferably from about 1 mg to about 100 mg, and even more preferably from about 1 mg to about 50 mg, on a daily basis.

All lactam-cyclized peptides of the present invention can be synthesized either by solid-phase synthesis or solution phase synthesis, or a combination of both, with peptide chain assembly on solid phase and cyclization or other modifications on resin or in solution. Such methods are well known in the art.

The following abbreviations used herein have the indicated meanings:

Ac: acetyl; Agl: aminoglycine; AMB: aminomethyl benzoic acid; AMPA: aminomethyl phenyl acetic acid; Bn: benzyl; Boc: tert-butyloxycarbonyl; BOP: (benzotriazol-1-yloxy)-tris(dimethylamino) phosphoniumhexafluorophosphate; 2-Br-Z: 2-bromobenzyloxycarbonyl; Bz: benzoyl; Bzl: benzyl; 2-Cl-Z: 2-chlorobenzyl-oxycarbonyl; Dab: 2,4-diaminobutyric acid; Dap:

2,3-diamino-propionic acid; DCC: dicyclohexylcarbodiimide; DCM: dichloromethane; DIC: diisopropyl carbodiimide; DIEA: diisopropyl-ethylamine; DMF: N,N-dimethyl formamide; DMSO: dimethyl-sulfoxide; EDT: 1,2-ethane-dithiol; Et: ethyl; Fm: 9-fluorenylmethyl; Fmoc: 9-fluorenylmethoxy carbonyl; HATU: N-[(dimethylamino)-1H-1,2,3-triazolo[4,5-b]pyridin-1-ylmethylene]-N-methylmethanaminium hexafluorophosphate N-oxide; HBTU: O-benzo-triazolyl-N,N,N',N'-tetramethyluronium hexafluorophosphate; HCTU: 1H-benzotriazolium 1[-bis(dimethylamino)methylene]-5-chloro-3-oxide hexafluorophosphate; HF: hydrogen fluoride; HOBt: hydroxybenzotriazole; IBCF: isobutyl chloroformate; iPr: isopropyl; IPA: isopropyl alcohol; Me: methyl; 2Nal: 2-naphthylalanine; NMM: N-methylmorpholine; NMP: N-methyl-pyrrolidone; OtBu: tert-butyl ester; Pbf: 2,2,4,6,7-pentamethyl-dihydrobenzofurane-5-sulfonyl; PBS: phosphate buffered saline; PyBOP: (benzotriazol-1-yloxy)-tris (pyrrolidino)-phosphonium hexafluorophosphate; PyBrOP: bromotris(pyrrolidino)phosphonium hexafluorophosphate; tBu: tert-butyl; TFA: trifluoroacetic acid; THF: tetrahydrofuran; TIS: triisopropyl silane; Tos: p-toluene-sulfonyl; Z: benzyloxycarbonyl; ZOSu: N-(benzyloxycarbonyl-oxy) succinimide.

Preparation of compounds of the present invention as described in the following examples is meant to be illustrative rather than limiting. In each of these examples, the observed molecular weight is reported as a de-convoluted value. The de-convoluted value is derived from the formula MW(observed)=n(m/z)-n, where m/z represents the charged ion (positive mode) and n is the number of charges of the specific species. When multiple charged species are present in the mass spectrum, the observed molecular weight is reported as an average.

The synthetic processes disclosed in Examples 85-87, and isotopic labeling procedures disclosed in Example 89, for cyclic lactam peptides containing isopropyl lysine side chains are equally applicable to other peptides disclosed herein containing lysine alkyl side chains, with appropriate modifications. The synthetic methods of Examples 86-88, which eliminate the need for toxic palladium catalysts, are also equally applicable to other peptides disclosed herein, with appropriate modifications.

EXAMPLE 1

Ac-cyclo[Dap-Tyr-Arg-DArg-2Nal-Gly-Glu]-Arg-$NH_2$ (SEQ ID NO:2)

The sequence Ac-Dap(Alloc)-Tyr(tBu)-Arg(Pbf)-DArg (Pbf)-2Nal-Gly-Glu(Oallyl)-Arg(Pbf) (SEQ ID NO:3) is assembled by standard Fmoc chemistry utilizing an ABI 431 Peptide Synthesizer (Applied Biosystems) as outlined in Scheme 1 below. The automated assembly is carried out by using the standard Applied Biosystems DCC/HOBt chemistry protocol or FastMoc chemistry HBTU/DIEA protocol following the supplier's directions (PE Applied Biosystems Inc., Foster City, Calif.). The solid support is Rink amide resin (4-(2',4'-dimethoxyphenyl-Fmoc-aminomethyl)-phenoxy resin) for C-terminal amides or indole resin [3-({ethyl-Fmoc-amino}-methyl)-indol-1-yl]-acetyl AM resin for C-terminal ethyl amides (NovaBiochem, EMD Biosciences, Inc., San Diego, Calif.). The stepwise chain assembly starts from the C-terminal end of the linear peptide and is accomplished in 9 major steps. In step 1, four equivalents of protected amino acid Fmoc-Arg(Pbf) are activated with DCC/HOBt (or HBTU/DIEA for FastMoc chemistry) in NMP, and coupled to deprotected Rink Amide resin using 20% piperidine. In step 2, four equivalents of Fmoc-Glu(Oallyl) are activated and coupled to the deprotected peptide resin from step 1. Appropriate steps are carried out until step 8, the coupling of Fmoc-Dap(Alloc). Then, Fmoc at the N-terminal end is removed using 20% piperidine in DMF and acetylation of the α-amino group is carried out off-line using 5 equivalents of acetic anhydride, 10 equivalents of DIEA in dry DMF or NMP, for 1 h at room temperature.

The allyl and Alloc side chain protection groups are removed with 0.1 equivalent of $Pd(Ph_3P)_4$ in the presence of 24 equivalents of phenylsilane in dichloromethane (Scheme 2). This process is repeated once for complete side chain deprotection. The deprotected carboxylic acid moiety of Glu is activated with PyBOP/DIEA and cyclized to the side chain amino group of Dap on the resin. The cyclized peptide is simultaneously deprotected and cleaved from the resin using a scavenger cocktail of TFA/$H_2O$/TIS/EDT (95/2/1/2, v/v/v/v), or TFA/$H_2O$/TIS/anisole (92/2/4/2, v/v/v/v) for 2 hours at room temperature. The solvents are then evaporated under vacuum, and the peptide is precipitated and washed three times with cold diethyl ether to remove the scavengers. Molecular weight calculated (MW cal.): 1142.30; MW observed (MW obs.): 1142.50.

Scheme 1.
Amino side chain to carboxyl side chain peptide assembly

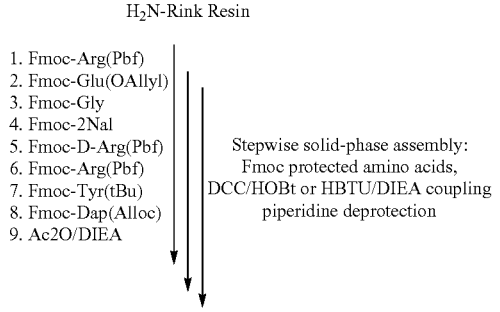

-continued

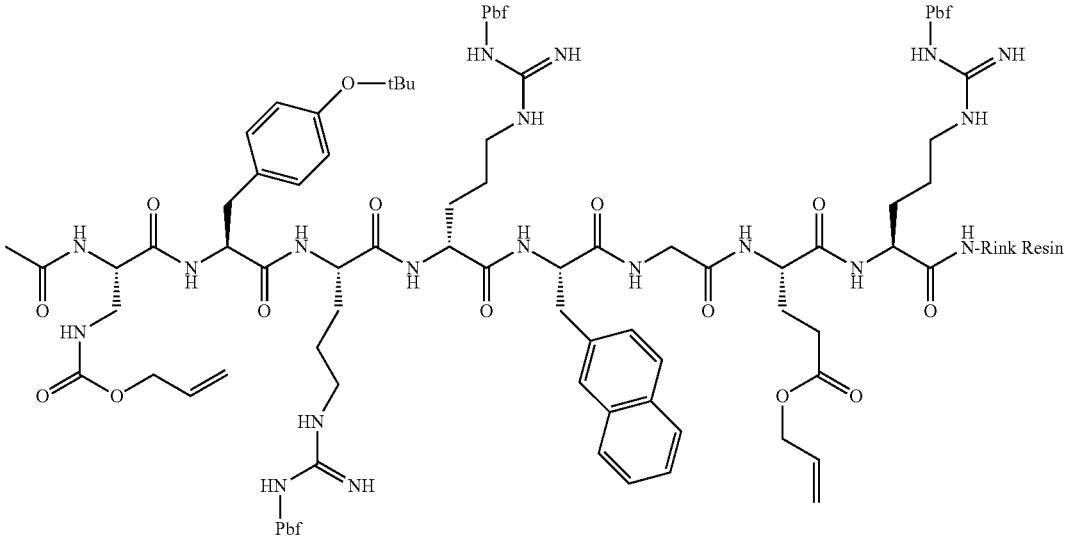

(SEQ ID NO: 4

Peptide purification is accomplished using standard preparative HPLC techniques. Immediately following the cyclization, the peptide solution is diluted with water containing 0.1% (v/v) TFA, loaded onto a reversed phase C18 HPLC column, and eluted with an aqueous 0.1% trifluoroacetic acid/acetonitrile (v/v) gradient while monitoring at 214 nm. The appropriate fractions are pooled and lyophilized. Further characterization of the final product is performed using analytical HPLC and mass spectral analysis by conventional techniques. For peptides with a basic side chain, the final lyophilized product is a TFA salt.

Scheme 2.
Amino side chain to carboxyl side chain ring cyclization and cleavage

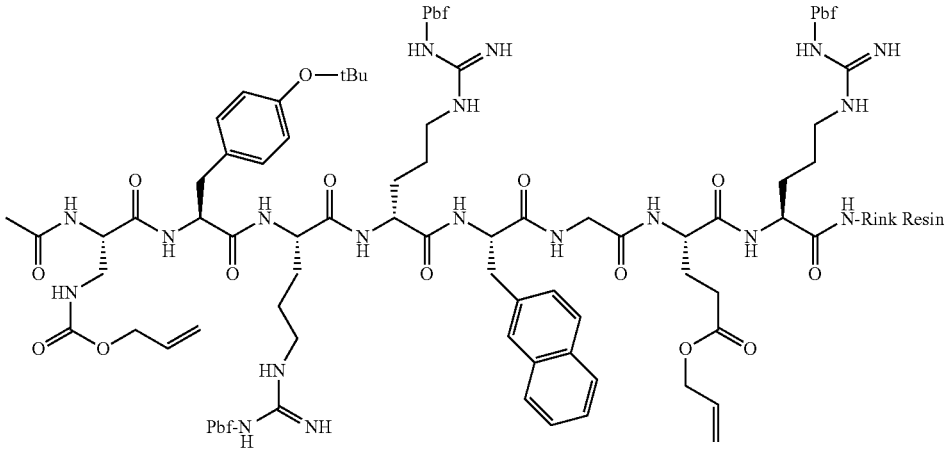

(SEQ ID NO: 4)

1. Allyl removal with $Pd(Ph_3P)_4(0)$
2. Cyclization with PyBOP/DIEA

-continued

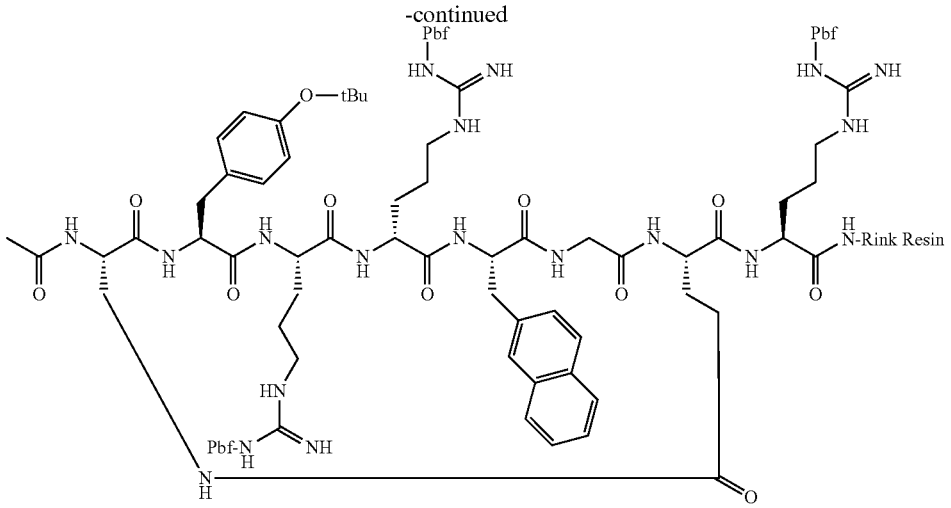

(SEQ ID NO: 5)

Side chain deprotection and TFA cleavage

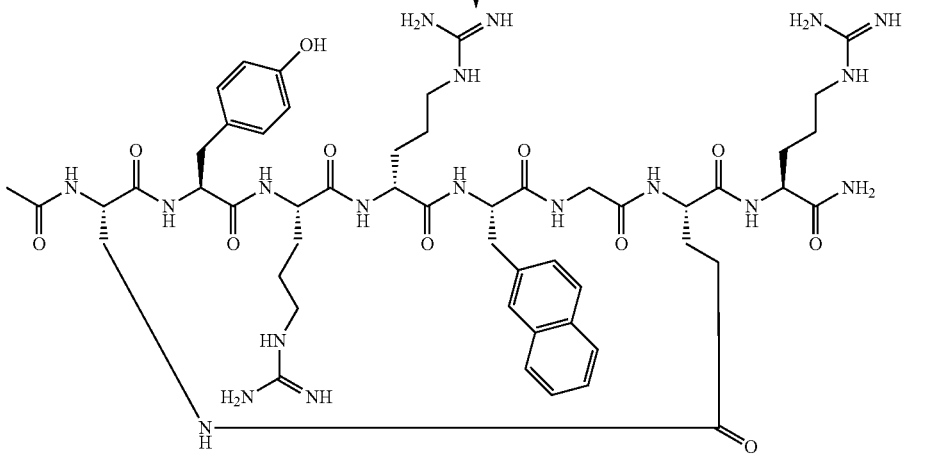

(SEQ ID NO: 2)

EXAMPLE 2

Ac-cyclo[Dab-Tyr-Arg-DArg-2Nal-Gly-Glu]-Arg-$NH_2$ (SEQ ID NO:6)

Prepare as in Example 1, except that Fmoc-Dap(Alloc) in step 8 is replaced with Fmoc-Dab(Alloc). MW cal.: 1156.33; MW obs.: 1156.10.

EXAMPLE 3

Ac-cyclo[Dap-Tyr-Lys(iPr)-DArg-2Nal-Gly-Glu]-Arg-NH (SEQ ID NO:7)

Prepare as in Example 1, except that Fmoc-Arg(Pbf) in step 6 is replaced with Fmoc-Lys(iPr)(Boc). MW cal.: 1156.37; MW obs.: 1156.78.

EXAMPLE 4 n-Hexanoyl-cyclo[Dap-Tyr-Lys(iPr)-DArg-2Nal-Gly-Glu]-Arg-$NH_2$ (SEQ ID NO:8)

Prepare as in Example 1, except that Fmoc-Arg(Pbf) in step 6 is replaced with Fmoc-Lys(iPr)(Boc). Additionally, acetic anhydride in step 9 is replaced with hexanoic acid activated with PyBOP/DIEA. MW cal.: 1212.47; MW obs.: 1212.92.

EXAMPLE 5

Ac-cyclo[(D/L)Agl-Tyr-Ar-DArg-2Nal-Gly-Glu]-Arg-$NH_2$ (SEQ ID NO:9)

Prepare as in Example 1, except that Fmoc-Glu(Oallyl) in step 2 is replaced with Fmoc-Glu(OtBu), and Fmoc-Dap (Alloc) in step 8 is replaced with Fmoc-(DL)Agl(Boc). After chain assembly, there is no $Pd(Ph_3P)_4$ treatment since no allyl protection is present. Instead, cyclization is carried out in solution after the linear peptide is cleaved from the solid support and deprotected. The crude linear peptide (0.25 mmol) from the cleavage is dried under vacuum and dissolved in 10 mL of dry DMF. This peptide solution is delivered to the following solution via a syringe pump during a 2 h period: 15 mL of dry dichloromethane and 15 mL of dry DMF containing 1.0 mmole of PyBOP and 4.0 mmoles of DIEA. The reaction is then allowed to proceed at room temperature for 2 h. Solvents are then evaporated under vacuum, the residue is loaded onto a preparative reversed phase C18 HPLC column, and target cyclic peptide is isolated and characterized as described in Example 1. MW cal.: 1128.27; MW obs.: 1128.26.

EXAMPLE 6

Ac-cyclo[Glu-Tyr-Arg-DArg-2Nal-Gly-Dap]-Arg-$NH_2$ (SEQ ID NO:10)

The sequence Glu(OtBu)-Tyr(tBu)-Arg(Pbf)-DArg(Pbf)-2Nal-Gly-Dap(Boc)-Arg(Pbf) (SEQ ID NO:11) is assembled by standard Fmoc chemistry utilizing an ABI 431 instrument as outlined in Scheme 3 below. The automated assembly is carried out by using the standard Applied Biosystems DCC/HOBt chemistry protocol or FastMoc chemistry (HBTU/DIEA) protocol following the supplier's directions (PE Applied Biosystems Inc., Foster City, Calif.). The solid support is Rink amide resin for C-terminal amides or indole resin [3-({ethyl-Fmoc-amino}-methyl)-indol-1-yl]-acetyl AM resin for C-terminal ethyl amides. Stepwise chain assembly starts from the C-terminal end of the linear peptide and is accomplished in 9 major steps. In step 1, four equivalents of protected amino acid Fmoc-Arg(Pbf) are activated with DCC/HOBt (or HBTU/DIEA for FastMoc chemistry) in NMP, and coupled to deprotected Rink Amide resin. In step 2, four equivalents of Fmoc-Dap(Boc) are activated and coupled to the deprotected resin from step 1. Appropriate steps are carried out until step 8, the coupling of Fmoc-Glu(OtBu). For step 9, Fmoc at the N-terminal end is removed using 20% piperidine in DMF and acetylation of the α-amino group is carried out off-line with 5 equivalents acetic anhydride, 10 equivalents DIEA in dry DMF or NMP, for 1 h at room temperature. The finished peptide is simultaneously deprotected and cleaved from the resin using a scavenger cocktail of TFA/$H_2O$/TIS/EDT (95/2/1/2, v/v/v/v), or TFA/$H_2O$/TIS/anisole (92/2/4/2, v/v/v/v) for 2 hours at room temperature (Scheme 4). The solvents are then evaporated under vacuum, and the peptide is precipitated and washed three times with cold diethyl ether to remove the scavengers. The crude product is used directly in the cyclization reaction. MW cal.: 1142.30; MW obs.: 1142.83.

Scheme 3.
Amino side chain to amino side chain peptide assembly

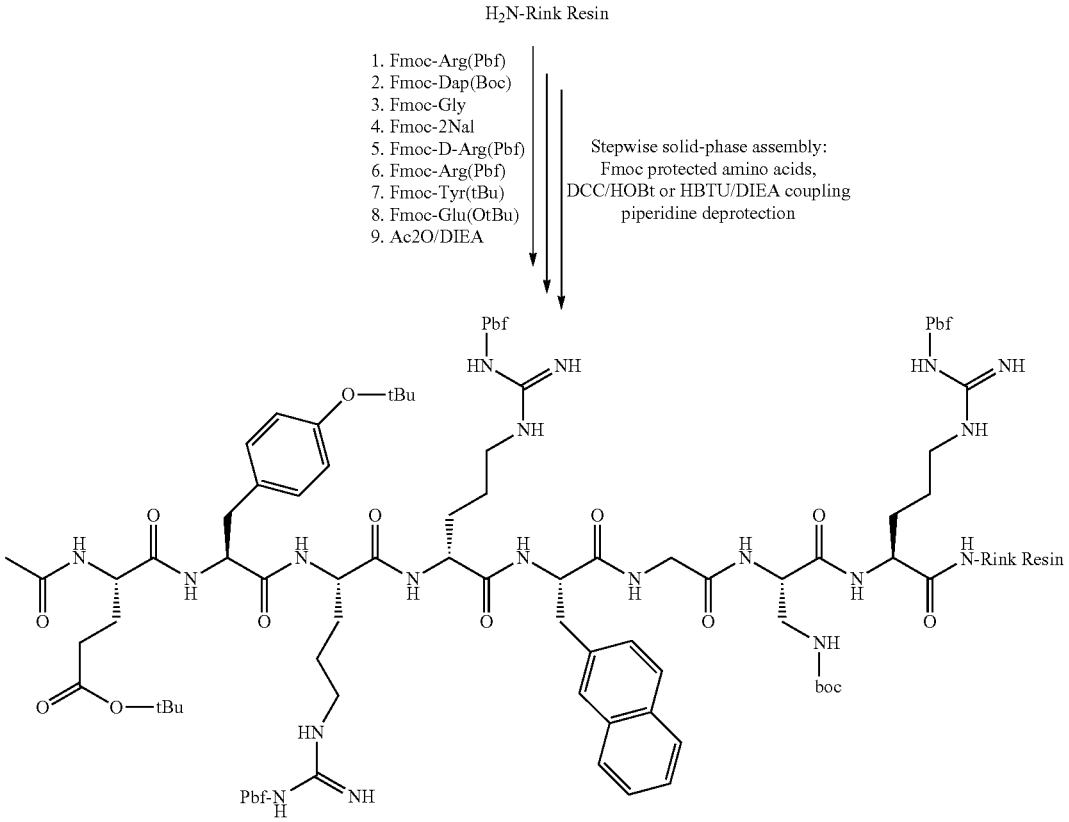

(SEQ ID NO: 12)

Cyclization is carried out in solution after the linear peptide is cleaved from the solid support with all the side chains deprotected (Scheme 4). The cleaved crude linear peptide (0.25 mmole) is dried under vacuum and dissolved in 10 mL of dry DMF. This peptide solution is delivered to the following reaction mixture via a syringe pump during a 2 h period: 15 mL of dry dichloromethane and 15 mL of dry DMF containing 1.0 mmole of PyBOP and 4.0 mmoles of DIEA. The reaction is then allowed to proceed at room temperature for 2 h. Solvents are evaporated under vacuum, the residue is loaded onto a preparative reversed phase C18 HPLC column, and target cyclic peptide is isolated and characterized as described in Example 1.

Scheme 4.
Amino side chain to amino side chain ring cyclization
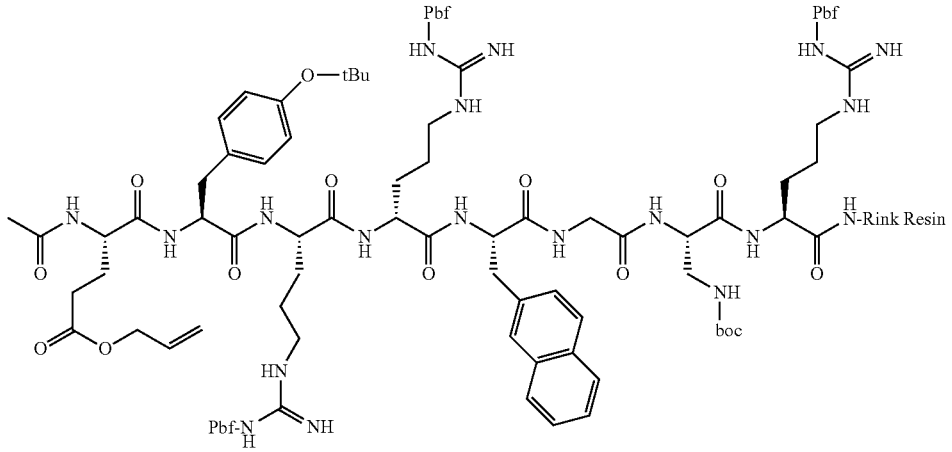
(SEQ ID NO: 12)
Side chain deprotection and TFA cleavage
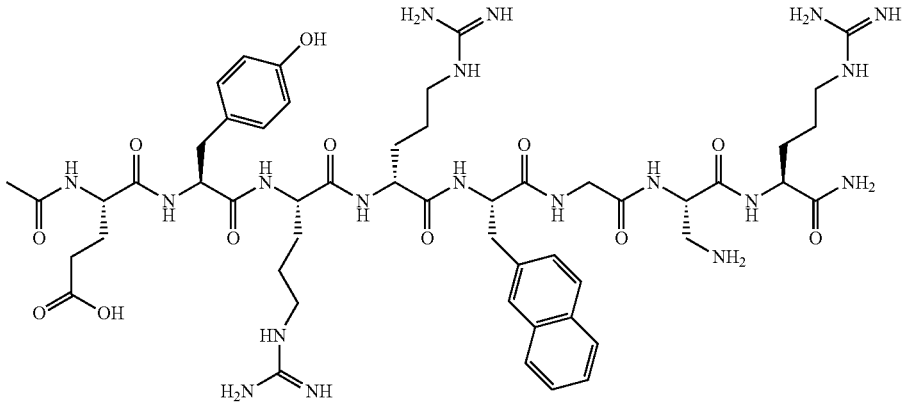
(SEQ ID NO: 13)
Cyclization in solution
PyBOP/DIEA
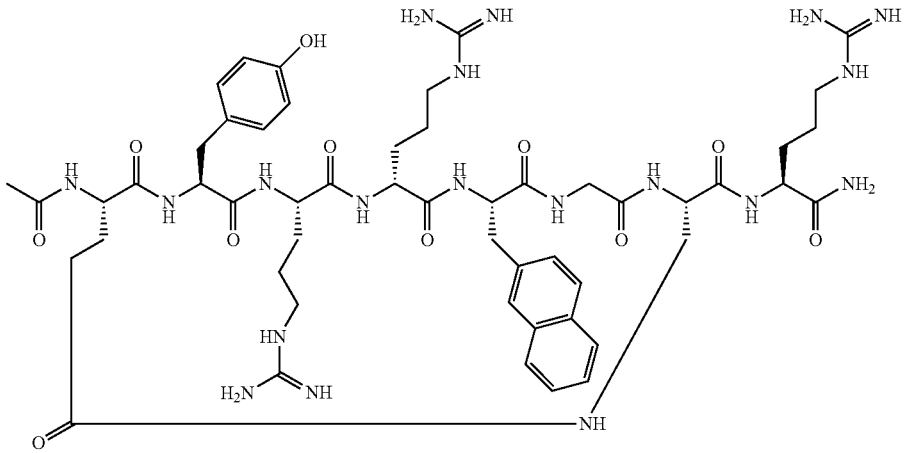
(SEQ ID NO: 10)

EXAMPLE 7

Bz-cyclo[Glu-Tyr-Arg-DArg-2Nal-Gly-Dap]-Arg-$NH_2$ (SEQ ID NO:14)

Prepare as in Example 6, except that acetic anhydride in step 9 is replaced with benzoic acid anhydride. MW cal.: 1204.37; MW obs.: 1204.87.

EXAMPLE 8

Ac-cyclo[Glu-Tyr-Arg-DArg-2Nal-Gly-DDap]-Arg-$NH_2$ (SEQ ID NO:15)

Prepare as in Example 6, except that Fmoc-Dap(Boc) in step 2 is replaced with Fmoc-DDap(Boc). MW cal.: 1142.30; MW obs.: 1142.73.

EXAMPLE 9

Ac-cyclo[Glu-Tyr-Arg-DArg-2Nal-Gly-Lys]-Arg-$NH_2$ (SEQ ID NO:16)

Prepare as in Example 6, except that Fmoc-Dap(Boc) in step 2 is replaced with Fmoc-Lys(Boc). MW cal.: 1184.38; MW obs.: 1184.23.

EXAMPLE 10

Ac-cyclo[Glu-Tyr-Arg-DArg-2Nal-Gly-Dab]-Arg-$NH_2$ (SEQ ID NO:17)

Prepare as in Example 6, except that Fmoc-Dap(Boc) in step 2 is replaced with Fmoc-Dab(Boc). MW cal.: 1156.33; MW obs.: 1156.07.

EXAMPLE 11

Ac-cyclo[Glu-Tyr-Arg-DArg-2Nal-Gly-(D/L)Agl]-Arg-$NH_2$ (SEQ ID NO:18)

Prepare as in Example 6, except that Fmoc-Dap(Boc) in step 2 is replaced with Fmoc-(DL)Agl(Boc). MW cal.: 1128.27; MW obs.: 1128.86.

EXAMPLE 12

Bz-cyclo[Glu-Tyr-Arg-DArg-2Nal-Gly-(D/L)Agl]-Arg-$NH_2$ (SEQ ID NO:19)

Prepare as in Example 6, except that Fmoc-Dap(Boc) in step 2 is replaced with Fmoc-(DL)Agl(Boc). In addition, acetic anhydride in step 9 is replaced with benzoic acid anhydride. MW cal.: 1190.34; MW obs.: 1190.99.

EXAMPLE 13

Bz-cyclo[Asp-Tyr-Arg-DArg-2Nal-Gly-Dab]-Arg-$NH_2$ (SEQ ID NO:20)

Prepare as in Example 6, except that Fmoc-Dap(Boc) in step 2 is replaced with Fmoc-Dab(Boc), and Fmoc-Glu (OtBu) in step 8 is replaced with Fmoc-Asp(OtBu). In addition, acetic anhydride in step 9 is replaced with benzoic acid anhydride. MW cal.: 1204.37; MW obs.: 1204.87.

EXAMPLE 14

Ac-cyclo[Asp-Tyr-Arg-DArg-2Nal-Gly-Dab]-Arg-$NH_2$ (SEQ ID NO:21)

Prepare as in Example 6, except that Fmoc-Dap(Boc) in step 2 is replaced with Fmoc-Dab(Boc), and Fmoc-Glu (OtBu) in step 8 is replaced with Fmoc-Asp(OtBu). MW cal.: 1142.30; MW obs.: 1142.81.

EXAMPLE 15

Ac-cyclo[Asp-Tyr-Arg-DArg-2Nal-Gly-Dap]-Arg-$NH_2$ (SEQ ID NO:22)

Prepare as in Example 6, except that Fmoc-Glu(OtBu) in step 8 is replaced with Fmoc-Asp(OtBu). MW cal.: 1128.27; MW obs.: 1128.78.

EXAMPLE 16

Bz-cyclo[Asp-Tyr-Arg-DArg-2Nal-Gly-Dap]-Arg-$NH_2$ (SEQ ID NO:23)

Prepare as in Example 6, except that Fmoc-Glu(OtBu) in step 8 is replaced with Fmoc-Asp(OtBu). In addition, acetic anhydride in step 9 is replaced with benzoic acid anhydride. MW cal.: 1190.34; MW obs.: 1190.69.

EXAMPLE 17

Ac-cyclo[Asp-Tyr-Arg-DArg-2Nal-Gly-(D/L)Agl]-Arg-$NH_2$ (SEQ ID NO:24)

Prepare as in Example 6, except that Fmoc-Dap(Boc) in step 2 is replaced with Fmoc-(DL)Agl(Boc), and Fmoc-Glu (OtBu) in step 8 is replaced with Fmoc-Asp(OtBu). MW cal.: 1114.24; MW obs.: 1114.85.

EXAMPLE 18

Ac-cyclo[Asp-Tyr-Lys($Me_2$)-DArg-2Nal-Gly-Dap]-Arg-$NH_2$ (SEQ ID NO:25)

Prepare as in Example 6, except that Fmoc-Arg(Pbf) in step 6 is replaced with Fmoc-Lys($Me_2$), and Fmoc-Glu(OtBu) in step 8 is replaced with Fmoc-Asp(OtBu). MW cal.: 1128.31; MW obs.: 1128.92.

EXAMPLE 19

Bz-cyclo[Asp-Tyr-Lys($Me_2$)-DArg-2Nal-Gly-Dap]-Arg-$NH_2$ (SEQ ID NO:26)

Prepare as in Example 6, except that Fmoc-Arg(Pbf) in step 6 is replaced with Fmoc-Lys($Me_2$), and Fmoc-Glu(OtBu) in step 8 is replaced with Fmoc-Asp(OtBu). In addition, acetic anhydride in step 9 is replaced with benzoic acid anhydride. MW cal.: 1190.38; MW obs.: 1191.14.

EXAMPLE 20 cyclo[Succinyl-Tyr-Arg-DArg-2Nal-Gly-(D/L)Agl]-Arg-$NH_2$ (SEQ ID NO:27)

Prepare as in Example 6, except that Fmoc-Dap(Boc) in step 2 is replaced with Fmoc-(DL)Agl(Boc), Fmoc-Glu(OtBu)

in step 8 is not used, and this step is omitted. In addition, acetic anhydride in step 9 is replaced with succinic anhydride. MW cal.: 1057.19; MW obs.: 1057.87.

EXAMPLE 21 cyclo[Succinyl-Tyr-Arg-DArg-2Nal-Gly-Dap]-Arg-$NH_2$ (SEQ ID NO:28)

Prepare as in Example 6, except that Fmoc-Glu(OtBu) in step 8 is not used, and this step is omitted. In addition, acetic anhydride in step 9 is replaced with succinic anhydride. MW cal.: 1071.22; MW obs.: 1071.85.

EXAMPLE 22 cyclo[Succinyl-Tyr-Arg-DArg-2Nal-Gly-Dab]-Arg-$NH_2$ (SEQ ID NO:29)

Prepare as in Example 6, except that Fmoc-Dap(Boc) in step 2 is replaced with Fmoc-Dab(Boc), Fmoc-Glu(OtBu) in step 8 is not used, and this step is omitted. In addition, acetic anhydride in step 9 is replaced with succinic anhydride. MW cal.: 1085.25; MW obs.: 1085.87.

EXAMPLE 23 cyclo[Succinyl-Tyr-Arg-DArg-2Nal-Gly-Orn]-Arg-$NH_2$ (SEQ ID NO:30)

Prepare as in Example 6, except that Fmoc-Dap(Boc) in step 2 is replaced with Fmoc-Orn(Boc), Fmoc-Glu(OtBu) in step 8 is not used, and this step is omitted. In addition, acetic anhydride in step 9 is replaced with succinic anhydride. MW cal.: 1099.27; MW obs.: 1100.23.

EXAMPLE 24 cyclo[Succinyl-Tyr-Arg-DArg-2Nal-Gly-Lys]-Arg-$NH_2$ (SEQ ID NO:31)

Prepare as in Example 6, except that Fmoc-Dap(Boc) in step 2 is replaced with Fmoc-Lys(Boc), Fmoc-Glu(OtBu) in step 8 is not used, and this step is omitted. In addition, acetic anhydride in step 9 is replaced with succinic anhydride. MW cal.: 1113.30; MW obs.: 1114.25.

EXAMPLE 25 cyclo[Gly-Tyr-Lys(iPr)-DArg-2Nal-Gly-DGlu]-Arg-$NH_2$ (SEQ ID NO:32)

The sequence Gly-Tyr(tBu)-Lys(iPr)(Boc)-DArg(Pbf)-2Nal-Gly-DGlu(Oallyl)-Arg(Pbf) (SEQ ID NO:33) is assembled by standard Fmoc chemistry utilizing an ABI 431 instrument as outlined in Scheme 5 below. The automated assembly is carried out by using the standard Applied Biosystems DCC/HOBt chemistry protocol or FastMoc HBTU/DIEA chemistry protocol following the supplier's directions (PE Applied Biosystems Inc., Foster City, Calif.). The solid support is Rink amide resin for amides or indole resin [3-({ethyl-Fmoc-amino}-methyl)-indol-1-yl]-acetyl AM resin for C-terminal ethyl amides. Stepwise chain assembly starts from the C-terminal end of the linear peptide and is accomplished in 8 major steps (Scheme 5). In step 1, four equivalents of protected amino acid Fmoc-Arg(Pbf) are activated with DCC/HOBt (or HBTU/DIEA for FastMoc chemistry) in NMP, and are coupled to deprotected Rink amide resin. In step 2, four equivalents of Fmoc-DGlu(Oallyl) are activated and coupled to the deprotected peptide resin from step 1. Appropriate steps are carried out until step 8, the coupling of Fmoc-Gly.

The allyl ester side chain protection group is removed with 0.1 equivalent of $Pd(Ph_3P)_4$ in the presence of 24 equivalents of phenylsilane in dichloromethane (Scheme 6). This process is repeated once for complete side chain deprotection. Then Fmoc at the N-terminal end is removed using 20% piperidine in DMF. The deprotected carboxylic acid moiety of DGlu is activated with PyBOP/DIEA, and cyclized to the α-amino group of glycine on the resin. The cyclized peptide is simultaneously deprotected and cleaved from the resin using a scavenger cocktail of TFA/$H_2O$/TIS/EDT (95/2/1/2, v/v/v/v), or TFA/$H_2O$/TIS/anisole (92/2/4/2, v/v/v/v) for 2 hours at room temperature. The solvents are then evaporated under vacuum, and the peptide is precipitated and washed three times with cold diethyl ether to remove the scavengers. MW cal.: 1085.29; MW obs.: 1085.32.

EXAMPLE 25A cyclo[Gly-Tyr-Lys(iPr)-DArg-2Nal-Gly-DGlu]-Arg-$NH_2$.Acetic Acid Salt (SEQ ID NO:34)

The TFA salt of the peptide of Example 25 is converted to an acetic acid salt by adsorbing the material onto a preparative C18 column of suitable size, equilibrated with 2% acetic acid/$H_2O$ (v/v). The column is then washed with three to five column volumes of 2% aqueous acetic acid (v/v). The peptide is eluted using 1:1 water/acetonitrile (v/v) containing 2% acetic acid by volume, and lyophilized. MW cal.: 1085.29; MW obs.: 1085.32.

Scheme 5.
α-amino group tocarboxyl side chain peptide assembly

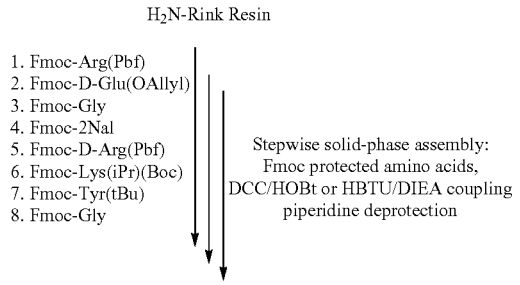

-continued

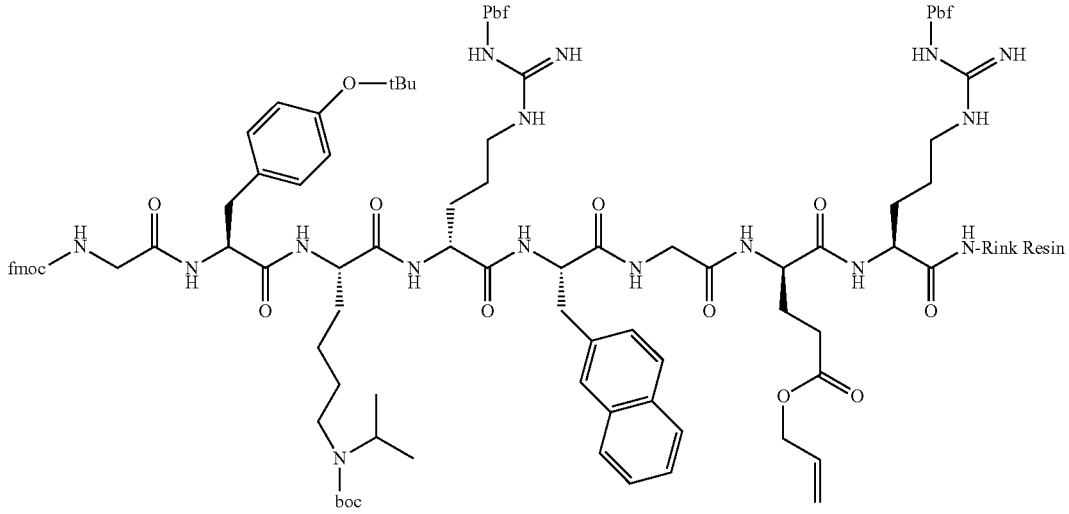

(SEQ ID NO: 35)

Peptide purification is accomplished using standard preparative HPLC techniques. Immediately following cyclization, the peptide solution is diluted with water containing 0.1% (v/v) TFA, loaded onto a reversed phase C18 HPLC column, and eluted with an aqueous 0.1% trifluoroacetic acid/acetonitrile (v/v) gradient while monitoring at 214 nm. The appropriate fractions are pooled and lyophilized. Further characterization of the final product is performed using analytical HPLC and mass spectral analysis by conventional methods. For peptides with a basic side chain, the final lyophilized product is a TFA salt.

Scheme 6.

α-amino group to carboxyl side chain ring cyclization and cleavage

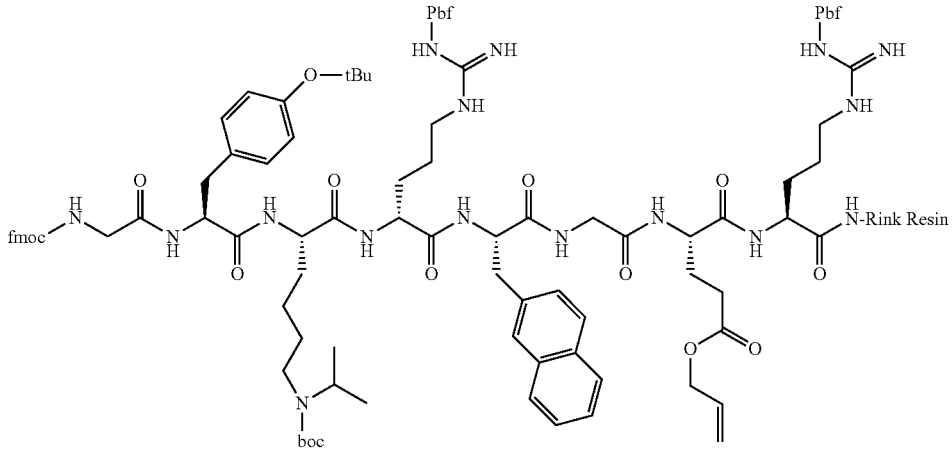

(SEQ ID NO: 35)

1. Allyl removal with $Pd(Ph_3P)_4(0)$
2. Fmoc removal with piperidine
3. Cyclization with PyBOP/DIEA -continued

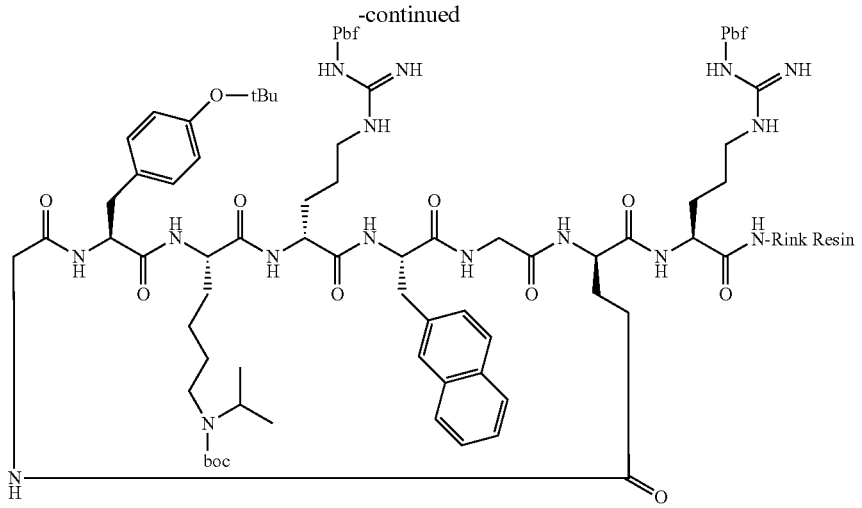

(SEQ ID NO: 36)

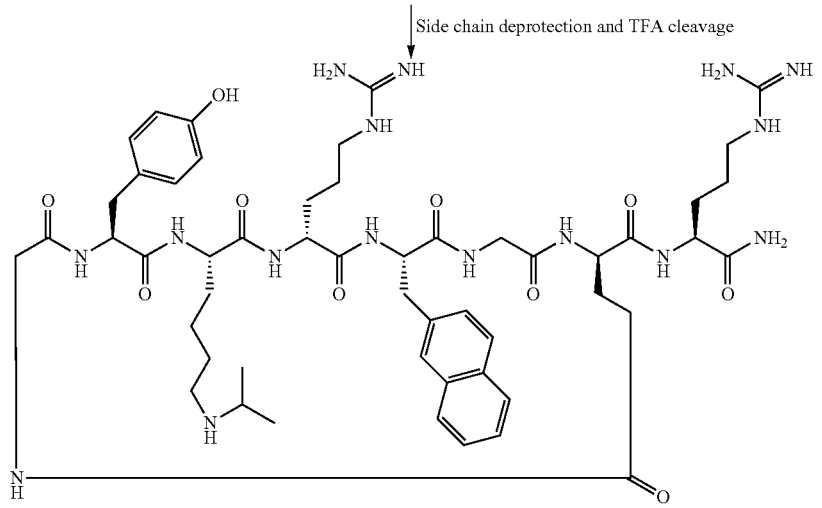

(SEQ ID NO: 32)

EXAMPLE 26 cyclo[Gly-Tyr-Lys(iPr)-DArg-2Nal-Gly-DGlu]-$NH_2$ (SEQ ID NO:37)

Prepare as in Example 25, except that step 1 is omitted. MW cal.: 929.10; MW obs.: 929.39.

EXAMPLE 26a cyclo[Gly-Tyr-Lys(iPr)-DArg-2Nal-Gly-DGlu]-$NH_2$.acetic acid salt (SEQ ID NO:38)

The TFA salt of the peptide of Example 26 is converted to an acetic acid salt by adsorbing the material onto a preparative C18 column of suitable size, equilibrated with 2% acetic acid/$H_2O$ (v/v). The column is then washed with three to five column volumes of 2% aqueous acetic acid (v/v). The peptide is eluted using 1:1 water/acetonitrile (v/v) containing 2% acetic acid by volume, and lyophilized. MW cal.: 929.10; MW obs.: 929.39.

EXAMPLE 27 cyclo[Gly-Tyr-Arg-DArg-2Nal-Gly-DGlu]-Arg-$NH_2$ (SEQ ID NO:39)

Prepare as in Example 25, except that Fmoc-Lys(iPr)(Boc) in step 6 is replaced with Fmoc-Arg(Pbf). MW cal.: 1071.22; MW obs.: 1071.02.

EXAMPLE 28 cyclo[Gly-Tyr-Lys(iPr)-DArg-2Nal-Gly-DGlu]-Lys (iPr)-$NH_2$ (SEQ ID NO:40)

Prepare as in Example 25, except that Fmoc-Arg(Pbf) in step 1 is replaced with Fmoc-Lys(iPr)(Boc). MW cal.: 1099.35; MW obs.: 1099.91.

EXAMPLE 29 cyclo[Tyr-Arg-DArg-2Nal-Gly-Glu]-Arg-$NH_2$ (SEQ ID NO:41)

Prepare as in Example 25, except that Fmoc-DGlu(Oallyl) in step 2 is replaced with Fmoc-Glu(Oallyl), Fmoc-Lys(iPr)

(Boc) in step 6 is replaced with Fmoc-Arg(Pbf), Fmoc-Gly in step 8 is not used, and step 8 is omitted. MW cal.: 1014.17; MW obs.: 1014.78.

EXAMPLE 30 cyclo[Tyr-Arg-DArg-2Nal-Gly-DGlu]-Arg-$NH_2$ (SEQ ID NO:42)

Prepare as in Example 25, except that Fmoc-Lys(iPr)(Boc) in step 6 is replaced with Fmoc-Arg(Pbf), Fmoc-Gly in step 8 is not used, and step 8 is omitted. MW cal.: 1014.17; MW obs.: 1014.65.

EXAMPLE 31 cyclo[Tyr-Arg-DArg-2Nal-Gly-Asp]-Arg-$NH_2$ (SEQ ID NO:43)

Prepare as in Example 25, except that Fmoc-DGlu(Oallyl) in step 2 is replaced with Fmoc-Asp(allyl), Fmoc-Lys(iPr)(Boc) in step 6 is replaced with Fmoc-Arg(Pbf), Fmoc-Gly in step 8 is not used, and step 8 is omitted. MW cal.: 1000.14; MW obs.: 1000.63.

EXAMPLE 32 cyclo[Gly-Tyr-Arg-DArg-2Nal-Gly-Asp]-Arg-$NH_2$ (SEQ ID NO:44)

Prepare as in Example 25, except that Fmoc-DGlu(Oallyl) in step 2 is replaced with Fmoc-Asp(allyl), and Fmoc-Lys(iPr)(Boc) in step 6 is replaced with Fmoc-Arg(Pbf). MW cal.: 1057.19; MW obs.: 1057.35.

EXAMPLE 33 cyclo[Gly-Tyr-Lys($Me_2$)-DArg-2Nal-Gly-Asp]-Arg-$NH_2$ (SEQ ID NO:45)

Prepare as in Example 25, except that Fmoc-DGlu(Oallyl) in step 2 is replaced with Fmoc-Asp(allyl), and Fmoc-Lys(iPr)(Boc) in step 6 is replaced with Fmoc-Lys($Me_2$). MW cal.: 1057.23; MW obs.: 1057.86.

EXAMPLE 34 cyclo[Gly-Tyr-Lys(iPr)-DArg-2Nal-Gly-Asp]-Arg-$NH_2$ (SEQ ID NO:46)

Prepare as in Example 25, except that Fmoc-DGlu(Oallyl) in step 2 is replaced with Fmoc-Asp(allyl). MW cal.: 1071.26; MW obs.: 1071.76.

EXAMPLE 35 cyclo[Gly-Tyr-Lys(iPr)-DArg-2Nal-Gly-Asp]-$NH_2$ (SEQ ID NO:47)

Prepare as in Example 25, except that step 1 is omitted, and Fmoc-DGlu(Oallyl) in step 2 is replaced with Fmoc-Asp(allyl). MW cal.: 915.07; MW obs.: 915.38.

EXAMPLE 36 cyclo[Gly-Tyr-Lys(iPr)-DArg-2Nal-Gly-Asp]-Lys(iPr)-$NH_2$ (SEQ ID NO:48)

Prepare as in Example 25, except that Fmoc-Arg(Pbf) in step 1 is replaced with Fmoc-Lys(iPr)(Boc), and Fmoc-DGlu(Oallyl) in step 2 is replaced with Fmoc-Asp(allyl). MW cal.: 1085.33; MW obs.: 1085.78.

EXAMPLE 37 cyclo[Gly-Tyr-Lys($Me_2$)-DArg-2Nal-Gly-Glu]-Arg-$NH_2$ (SEQ ID NO:49)

Prepare as in Example 25, except that Fmoc-DGlu(Oallyl) in step 2 is replaced with Fmoc-Glu(Oallyl), and Fmoc-Lys(iPr)(Boc) in step 6 is replaced with Fmoc-Lys($Me_2$). MW cal.: 1071.26; MW obs.: 1071.05.

EXAMPLE 38 cyclo[Gly-Tyr-Arg-DArg-2Nal-Gly-Glu]-Arg-$NH_2$ (SEQ ID NO:50)

Prepare as in Example 25, except that Fmoc-DGlu(Oallyl) in step 2 is replaced with Fmoc-Glu(Oallyl), and Fmoc-Lys(iPr)(Boc) in step 6 is replaced with Fmoc-Arg(Pbf). MW cal.: 1071.22; MW obs.: 1071.50.

EXAMPLE 39 cyclo[Gly-Tyr-Lys(iPr)-DArg-2Nal-Gly-Glu]-Arg-$NH_2$ (SEQ ID NO:51)

Prepare as in Example 25, except that Fmoc-DGlu(Oallyl) in step 2 is replaced with Fmoc-Glu(Oallyl). MW cal.: 1085.29; MW obs.: 1085.91.

EXAMPLE 40 cyclo[Gly-Tyr-Lys(iPr)-DArg-2Nal-Gly-Glu]-$NH_2$ (SEQ ID NO:52)

Prepare as in Example 25, except that step 1 is omitted, and Fmoc-DGlu(Oallyl) in step 2 is replaced with Fmoc-Glu(Oallyl). MW cal.: 929.10; MW obs.: 929.39.

EXAMPLE 41 cyclo[Gly-Tyr-Lys(iPr)-DArg-2Nal-Gly-Asp]-NHEt (SEQ ID NO:53)

Prepare as in Example 25, except that Rink amide resin is replaced with [3-({ethyl-Fmoc-amino}-methyl)-indol-1-yl]-acetyl AM resin, step 1 is omitted, and Fmoc-DGlu(Oallyl) in step 2 is replaced with Fmoc-Asp(allyl). MW cal.: 943.13; MW obs.: 943.36.

EXAMPLE 42 cyclo[Gly-Tyr-Lys(iPr)-DArg-2Nal-Gly-Glu]-NHEt (SEQ ID NO:54)

Prepare as in Example 25, except that Rink amide resin is replaced with [3-({ethyl-Fmoc-amino}-methyl)-indol-1-yl]- acetyl AM resin, step 1 is omitted, and Fmoc-DGlu(Oallyl) in step 2 is replaced with Fmoc-Glu(Oallyl). MW cal.: 957.15; MW obs.: 957.50.

EXAMPLE 43 cyclo[Gly-Tyr-Lys(iPr)-DArg-2Nal-Gly-DGlu]-NHEt (SEQ ID NO:55)

Prepare as in Example 25, except that Rink amide resin is replaced with [3-({ethyl-Fmoc-amino}-methyl)-indol-1-yl]-acetyl AM resin, and step 1 is omitted. MW cal.: 957.15; MW obs.: 957.46.

EXAMPLE 44 cyclo[Gly-Tyr-Lys(iPr)-DArg-2Nal-Gly-DGlu]-Arg-NHEt (SEQ ID NO:56)

Prepare as in Example 25, except that Rink amide resin is replaced with [3-({ethyl-Fmoc-amino}-methyl)-indol-1-yl]-acetyl AM resin. MW cal.: 1113.34; MW obs.: 1113.81.

EXAMPLE 44a cyclo[Gly-Tyr-Lys(iPr)-DArg-2Nal-Gly-DGlu]-Arg-NHEt.acetic acid salt (SEQ ID NO:57)

The TFA salt of the peptide of Example 44 is converted to an acetic acid salt by adsorbing the material onto a preparative C18 column of suitable size, equilibrated with 2% acetic acid/$H_2O$ (v/v). The column is then washed with three to five column volumes of 2% aqueous acetic acid (v/v). The peptide is eluted using 1:1 water/acetonitrile (v/v) containing 2% acetic acid by volume, and lyophilized. MW cal.: 1113.34; MW obs.: 1113.81.

EXAMPLE 45 cyclo[Gly-Tyr-Lys(iPr)-DArg-2Nal-Gly-DGlu]-Lys (iPr)-NHEt (SEQ ID NO:58)

Prepare as in Example 25, except that Rink amide resin is replaced with [3-({ethyl-Fmoc-amino}-methyl)-indol-1-yl]-acetyl AM resin, and Fmoc-Arg(Pbf) in step 1 is replaced with Fmoc-Lys(iPr)(Boc). MW cal.: 1127.41; MW obs.: 1127.35.

EXAMPLE 46 cyclo[Lys(Ac)-Tyr-Lys($Me_2$)-DArg-2Nal-Gly-Glu]-Arg-$NH_2$ (SEQ ID NO:59)

Prepare as in Example 25, except that Fmoc-DGlu(Oallyl) in step 2 is replaced with Fmoc-Glu(OtBu), Fmoc-Lys(iPr)(Boc) in step 6 is replaced with Fmoc-Lys($Me_2$), and Fmoc-Gly in step 8 is replaced with Boc-Lys(Fmoc). After chain assembly, Fmoc on the side chain of the N-terminal Lys is removed with 20% piperidine in DMF and the Lys side chain is then acetylated using 10 equivalents of acetic anhydride/DIEA at room temperature for one hour. All side chain protection groups are removed and the linear peptide is cleaved from the solid support using a mixture of TFA/water/TIS/anisole (90/5/2.5/2.5, v/v/v/v) for 2 h at room temperature. Cyclization of the crude linear peptide is carried out in solution. The cleaved crude linear peptide (~0.25 mmole) is dried under vacuum and dissolved in 10 mL of dry DMF. This peptide solution is delivered to the following reaction mixture via a syringe pump during a 2 h period: 15 mL of dry dichloromethane and 15 mL of dry DMF containing 1.0 mmole of PyBOP and 4.0 mmoles of DIEA. The reaction is then allowed to proceed at room temperature for 2 h. Solvents are then evaporated under vacuum, the residue is loaded onto a reversed phase C18 preparative HPLC column, and the target cyclic peptide is isolated and characterized as described in Example 1. MW cal.: 1184.42; MW obs.: 1184.06.

EXAMPLE 47 cyclo[Dap(Ac)-Tyr-Lys($Me_2$)-DArg-2Nal-Gly-Glu]-$NH_2$ (SEQ ID NO:60)

Prepare as in Example 25, except that step 1 is omitted, Fmoc-DGlu(Oallyl) in step 2 is replaced with Fmoc-Glu (OtBu), Fmoc-Lys(iPr)(Boc) in step 6 is replaced with Fmoc-Lys($Me_2$), and Fmoc-Gly in step 8 is replaced with Boc-Dap (Fmoc). After chain assembly, Fmoc on the side chain of the N-terminal Dap is removed using 20% piperidine in DMF, and the Dap side chain is then acetylated with 10 equivalents of acetic anhydride/DIEA at room temperature for one hour. All side chain protection groups are then removed and the linear peptide is cleaved from the solid support using a mixture of TFA/water/TIS/anisole (90/5/2.5/2.5, v/v/v/v) for 2 h at room temperature. Cyclization of the crude linear peptide is carried out in solution. The cleaved crude linear peptide (~0.25 mmole) is dried under vacuum and dissolved in 10 mL of dry DMF. This peptide solution is delivered to the following reaction mixture via a syringe pump during a 2 h period: 15 mL of dry dichloromethane and 15 mL of dry DMF containing 1.0 mmole of PyBOP and 4.0 mmoles of DIEA. The reaction is allowed to proceed at room temperature for 2 h. Solvents are then evaporated under vacuum, the residue is loaded onto a preparative HPLC column, and the target cyclic peptide is isolated and characterized as described in Example 1. MW cal.: 986.15; MW obs.: 985.97.

EXAMPLE 48 cyclo[Ala-Tyr-Lys(iPr)-DArg-2Nal-Gly-Glu]-$NH_2$ (SEQ ID NO:61)

Prepare as in Example 25, except that step 1 is omitted, Fmoc-DGlu(Oallyl) in step 2 is replaced with Fmoc-Glu(Oallyl), and Fmoc-Gly in step 8 is replaced with Fmoc-Ala. MW cal.: 943.13; MW obs.: 942.92.

EXAMPLE 49 cyclo[DAla-Tyr-Lys(iPr)-DArg-2Nal-Gly-Glu]-$NH_2$ (SEQ ID NO:62)

Prepare as in Example 25, except that step 1 is omitted, Fmoc-DGlu(Oallyl) in step 2 is replaced with Fmoc-Glu(Oallyl), and Fmoc-Gly in step 8 is replaced with Fmoc-DAla. MW cal.: 943.13; MW obs.: 943.44.

EXAMPLE 50 cyclo[DAla-Tyr-Lys(iPr)-DArg-2Nal-Gly-DGlu]-$NH_2$ (SEQ ID NO:63)

Prepare as in Example 25, except that step 1 is omitted, and Fmoc-Gly in step 8 is replaced with Fmoc-DAla. MW cal.: 943.13; MW obs.: 943.42.

EXAMPLE 51 cyclo[Ala-Tyr-Lys(iPr)-DArg-2Nal-Gly-DGlu]-$NH_2$ (SEQ ID NO:64)

Prepare as in Example 25, except that step 1 is omitted, and Fmoc-Gly in step 8 is replaced with Fmoc-Ala. MW cal.: 943.13; MW obs.: 943.48.

EXAMPLE 52 cyclo[Leu-Tyr-Lys(iPr)-DArg-2Nal-Gly-DGlu]-$NH_2$ (SEQ ID NO:65)

Prepare as in Example 25, except that step 1 is omitted, and Fmoc-Gly in step 8 is replaced with Fmoc-Leu. MW cal.: 985.21; MW obs.: 985.56.

EXAMPLE 53 cyclo[Leu-Tyr-Lys(iPr)-DArg-2Nal-Gly-Glu]-$NH_2$ (SEQ ID NO:66)

Prepare as in Example 25, except that step 1 is omitted, Fmoc-DGlu(Oallyl) in step 2 is replaced with Fmoc-Glu(Oallyl), and Fmoc-Gly in step 8 is replaced with Fmoc-Leu. MW cal.: 985.21; MW obs.: 985.49.

EXAMPLE 54 cyclo[DPhe-Tyr-Lys(iPr)-DArg-2Nal-Gly-Glu]-$NH_2$ (SEQ ID NO:67)

Prepare as in Example 25, except that step 1 is omitted, Fmoc-DGlu(Oallyl) in step 2 is replaced with Fmoc-Glu(Oallyl), and Fmoc-Gly in step 8 is replaced with Fmoc-DPhe. MW cal.: 1019.22; MW obs.: 1019.52.

EXAMPLE 55 cyclo[Phe-Tyr-Lys(iPr)-DArg-2Nal-Gly-Glu]-$NH_2$ (SEQ ID NO:68)

Prepare as in Example 25, except that step 1 is omitted, Fmoc-DGlu(Oallyl) in step 2 is replaced with Fmoc-Glu(Oallyl), and Fmoc-Gly in step 8 is replaced with Fmoc-Phe. MW cal.: 1019.22; MW obs.: 1019.53.

EXAMPLE 56 cyclo[DPhe-Tyr-Lys(iPr)-DArg-2Nal-Gly-DGlu]-$NH_2$ (SEQ ID NO:69)

Prepare as in Example 25, except that step 1 is omitted, and Fmoc-Gly in step 8 is replaced with Fmoc-DPhe. MW cal.: 1019.22; MW obs.: 1019.50.

EXAMPLE 57 cyclo[Phe-Tyr-Lys(iPr)-DArg-2Nal-Gly-DGlu]-Lys (iPr)-$NH_2$ (SEQ ID NO:70)

Prepare as in Example 25, except that Fmoc-Arg(Pbf) in step 1 is replaced with Fmoc-Lys(iPr)(Boc), and Fmoc-Gly in step 8 is replaced with Fmoc-Phe. MW cal.: 1189.48; MW obs.: 1189.92.

EXAMPLE 57a cyclo[Phe-Tyr-Lys(iPr)-DArg-2Nal-Gly-DGlu]-Lys (iPr)-$NH_2$.acetic acid salt (SEQ ID NO:71)

The TFA salt of the peptide of Example 57 is converted to an acetic acid salt by adsorbing the material onto a preparative C18 column of suitable size, equilibrated with 2% acetic acid/$H_2O$ (v/v). The column is then washed with three to five column volumes of 2% aqueous acetic acid (v/v). The peptide is eluted using 1:1 water/acetonitrile (v/v) containing 2% acetic acid by volume, and lyophilized. MW cal.: 1189.48; MW obs.: 1189.92.

EXAMPLE 58 cyclo[Phe-Tyr-Lys(iPr)-DArg-2Nal-Gly-DGlu]-Arg-$NH_2$ (SEQ ID NO:72)

Prepare as in Example 25, except that Fmoc-Gly in step 8 is replaced with Fmoc-Phe. MW cal.: 1175.41; MW obs.: 1175.81.

EXAMPLE 59 cyclo[Phe-Tyr-Lys(iPr)-DArg-2Nal-Gly-DGlu]-$NH_2$ (SEQ ID NO:73)

Prepare as in Example 25, except that step 1 is omitted, and Fmoc-Gly in step 8 is replaced with Fmoc-Phe. MW cal.: 1019.22; MW obs.: 1019.56.

EXAMPLE 60 cyclo[Phe-Tyr-Lys(iPr)-DArg-2Nal-Gly-DGlu]-Lys (iPr)-NHEt (SEQ ID NO:74)

Prepare as in Example 25, except that Rink amide resin is replaced with [3-({ethyl-Fmoc-amino}-methyl)-indol-1-yl]-acetyl AM resin, Fmoc-Arg(Pbf) in step 1 is replaced with Fmoc-Lys(iPr)(Boc), and Fmoc-Gly in step 8 is replaced with Fmoc-Phe. MW cal.: 1217.53; MW obs.: 1217.97.

EXAMPLE 60a cyclo[Phe-Tyr-Lys(iPr)-DArg-2Nal-Gly-DGlu]-Lys (iPr)-NHEt.acetic acid salt (SEQ ID NO:75)

The TFA salt of the peptide of Example 60 is converted to an acetic acid salt by adsorbing the material onto a preparative C18 column of suitable size, equilibrated with 2% acetic acid/$H_2O$ (v/v). The column is then washed with three to five column volumes of 2% aqueous acetic acid (v/v). The peptide is eluted using 1:1 water/acetonitrile (v/v) containing 2% acetic acid by volume, and lyophilized. MW cal.: 1217.53; MW obs.: 1217.97.

EXAMPLE 61 cyclo[DAla-Tyr-Lys(iPr)-DArg-2Nal-Gly-Glu]-NHEt (SEQ ID NO:76)

Prepare as in Example 25, except that Rink amide resin is replaced with [3-({ethyl-Fmoc-amino}-methyl)-indol-1-yl]-acetyl AM resin, step 1 is omitted, Fmoc-DGlu(Oallyl) in step 2 is replaced with Fmoc-Glu(Oallyl), and Fmoc-Gly in step 8 is replaced with Fmoc-DAla. MW cal.: 971.18; MW obs.: 971.49.

EXAMPLE 62 cyclo[2Nal-Tyr-Lys(iPr)-DArg-2Nal-Gly-Glu]NHEt (SEQ ID NO:77)

Prepare as in Example 25, except that Rink amide resin is replaced with [3-({ethyl-Fmoc-amino}-methyl)-indol-1-yl]-acetyl AM resin, step 1 is omitted, Fmoc-DGlu(Oallyl) in step 2 is replaced with Fmoc-Glu(Oallyl), and Fmoc-Gly in step 8 is replaced with Fmoc-2Nal. MW cal.: 1097.34; MW obs.: 1097.53.

EXAMPLE 63 cyclo[DPhe-Tyr-Lys(iPr)-DArg-2Nal-Gly-Glu]-NHEt (SEQ ID NO:78)

Prepare as in Example 25, except that Rink amide resin is replaced with [3-({ethyl-Fmoc-amino}-methyl)-indol-1-yl]-acetyl AM resin, step 1 is omitted, Fmoc-DGlu(Oallyl) in step 2 is replaced with Fmoc-Glu(Oallyl), and Fmoc-Gly in step 8 is replaced with Fmoc-DPhe. MW cal.: 1047.28; MW obs.: 1047.51.

EXAMPLE 64 cyclo[Phe-Tyr-Lys(iPr)-DArg-2Nal-Gly-Glu]-NHEt (SEQ ID NO:79)

Prepare as in Example 25, except that Rink amide resin is replaced with [3-({ethyl-Fmoc-amino}-methyl)-indol-1-yl]-acetyl AM resin, step 1 is omitted, Fmoc-DGlu(Oallyl) in step 2 is replaced with Fmoc-Glu(Oallyl), and Fmoc-Gly in step 8 is replaced with Fmoc-Phe. MW cal.: 1047.28; MW obs.: 1047.57.

EXAMPLE 65 cyclo[Gly-Tyr-Lys(iPr)-DArg-2Nal-Gly-DGlu]-Gly-2Nal-$NH_2$ (SEQ ID NO:80)

Prepare as in Example 25, except that Fmoc-Arg(Pbf) in step 1 is replaced with Fmoc-2Nal, and one step is added between steps 1 and 2 using Fmoc-Gly. MW cal.: 1183.39; MW obs.: 1183.26.

EXAMPLE 66 cyclo[Gly-Tyr-Lys(iPr)-DArg-2Nal-Gly-Glu]-β-Ala-D2Nal-$NH_2$ (SEQ ID NO:81)

Prepare as in Example 25, except that Fmoc-Arg(Pbf) in step 1 is replaced with Fmoc-D2Nal, one step is added between steps 1 and 2 using Fmoc-β-Ala, and Fmoc-DGlu (Oallyl) in step 2 is replaced with Fmoc-Glu(Oallyl). MW cal.: 1197.40; MW obs.: 1196.70.

EXAMPLE 67 cyclo[β-Ala-Tyr-Arg-DArg-2Nal-Gly-Glu]-Arg-$NH_2$ (SEQ ID NO:82)

Prepare as in Example 25, except that Fmoc-DGlu(Oallyl) in step 2 is replaced with Fmoc-Glu(Oallyl), Fmoc-Lys(iPr) (Boc) in step 6 is replaced with Fmoc-Arg(Pbf), and Fmoc-Gly in step 8 is replaced with Fmoc-β-Ala. MW cal.: 1085.25; MW obs.: 1085.05.

EXAMPLE 68 cyclo[β-Ala-Tyr-Arg-DArg-2Nal-Gly-Asp]-Arg-$NH_2$ (SEQ ID NO:83)

Prepare as in Example 25, except that Fmoc-DGlu(Oallyl) in step 2 is replaced with Fmoc-Asp(Oallyl), Fmoc-Lys(iPr) (Boc) in step 6 is replaced with Fmoc-Arg(Pbf), and Fmoc-Gly in step 8 is replaced with Fmoc-β-Ala. MW cal.: 1071.22; MW obs.: 1071.15.

EXAMPLE 69 cyclo[5-aminovaleryl-Tyr-Arg-DArg-2Nal-Gly-Glu]-Arg-$NH_2$ (SEQ ID NO:84)

Prepare as in Example 25, except that Fmoc-DGlu(Oallyl) in step 2 is replaced with Fmoc-Glu(Oallyl), Fmoc-Lys(iPr) (Boc) in step 6 is replaced with Fmoc-Arg(Pbf), and Fmoc-Gly in step 8 is replaced with Fmoc-5-aminovalieric acid. MW cal.: 1113.30; MW obs.: 1113.40.

EXAMPLE 70 cyclo[5-aminovaleryl-Tyr-Arg-DArg-2Nal-Gly-Asp]-Arg-$NH_2$ (SEQ ID NO:85)

Prepare as in Example 25, except that Fmoc-DGlu(Oallyl) in step 2 is replaced with Fmoc-Asp(Oallyl), Fmoc-Lys(iPr) (Boc) in step 6 is replaced with Fmoc-Arg(Pbf), and Fmoc-Gly in step 8 is replaced with Fmoc-5-amino valeric acid. MW cal.: 1099.27; MW obs.: 1100.25.

EXAMPLE 71 cyclo[(4-AMPA)-Tyr-Arg-DArg-2Nal-Gly-Asp]-Arg-$NH_2$ (SEQ ID NO:86)

Prepare as in Example 25, except that Fmoc-DGlu(Oallyl) in step 2 is replaced with Fmoc-Asp(Oallyl), Fmoc-Lys(iPr) (Boc) in step 6 is replaced with Fmoc-Arg(Pbf), and Fmoc-Gly in step 8 is replaced with Fmoc-4-aminomethyl phenylacetic acid (4-AMPA). MW cal.: 1147.32; MW obs.: 1148.20.

EXAMPLE 72 cyclo[(4-AMPA)-Tyr-Arg-DArg-2Nal-Gly-Glu]-Arg-$NH_2$ (SEQ ID NO:87)

Prepare as in Example 25, except that Fmoc-DGlu(Oallyl) in step 2 is replaced with Fmoc-Glu(Oallyl), Fmoc-Lys(iPr) (Boc) in step 6 is replaced with Fmoc-Arg(Pbf), and Fmoc-Gly in step 8 is replaced with Fmoc-4-aminomethyl phenylacetic acid (4-AMPA). MW cal.: 1161.34; MW obs.: 1161.99.

EXAMPLE 73 cyclo[(4-AMPA)-Tyr-Arg-DArg-2Nal-Gly-Glu]-DArg-$NH_2$ (SEQ ID NO:88)

Prepare as in Example 25, except that Fmoc-Arg(Pbf) in step 1 is replaced with Fmoc-DArg(Pbf), Fmoc-DGlu(Oallyl)

in step 2 is replaced with Fmoc-Glu(Oallyl), Fmoc-Lys(iPr)(Boc) in step 6 is replaced with Fmoc-Arg(Pbf), and Fmoc-Gly in step 8 is replaced with Fmoc-4-aminomethyl phenylacetic acid (4-AMPA). MW cal.: 1161.34; MW obs.: 1161.83.

EXAMPLE 74 cyclo[(4-AMB)-Tyr-Arg-DArg-2Nal-Gly-Glu]-Arg-$NH_2$ (SEQ ID NO:89)

Prepare as in Example 25, except that Fmoc-DGlu(Oallyl) in step 2 is replaced with Fmoc-Glu(Oallyl), Fmoc-Lys(iPr)(Boc) in step 6 is replaced with Fmoc-Arg(Pbf), and Fmoc-Gly in step 8 is replaced with Fmoc-4-aminomethyl benzoic acid (4-AMB). MW cal.: 1147.32; MW obs.: 1147.66.

EXAMPLE 75 cyclo[Gly-Tyr-Lys(iPr)-DArg-2Nal-Gly-DGlu]-Lys(iPr)-Gly-2Nal-$NH_2$ (SEQ ID NO:90)

Prepare as in Example 25, except that step 1 is replaced with three sequential residue couplings: first Fmoc-2Nal, then Fmoc-Gly, and then Fmoc-Lys(iPr)(Boc). MW cal.: 1353.69; MW obs.: 1354.03.

EXAMPLE 76 cyclo[Phe-Tyr-Lys(iPr)-DArg-2Nal-Gly-DGlu]-Lys(iPr)-Gly-2Nal-$NH_2$ (SEQ ID NO:91)

Prepare as in Example 25, except that step 1 is replaced with three sequential residue couplings: first Fmoc-2Nal, then Fmoc-Gly, and then Fmoc-Lys(iPr)(Boc). In addition, Fmoc-Gly in step 8 is replaced with Fmoc-Phe. MW cal.: 1443.82; MW obs.: 1444.13.

EXAMPLE 77 cyclo[Gly-Tyr-Lys(iPr)-DArg-2Nal-Gly-DGlu]-Gly-DPhe-$NH_2$ (SEQ ID NO:92)

Prepare as in Example 25, except that step 1 is replaced with two sequential residue couplings: first Fmoc-DPhe, then Fmoc-Gly. MW cal.: 1133.36; MW obs.: 1133.73.

EXAMPLE 78 cyclo[Gly-Tyr-Lys(iPr)-DArg-2Nal-Gly-DGlu]-Lys(iPr)-DPhe-$NH_2$ (SEQ ID NO:93)

Prepare as in Example 25, except that step 1 is replaced with two sequential residue couplings: first Fmoc-DPhe, then Fmoc-Lys(iPr)(Boc). MW cal.: 1246.58; MW obs.: 1246.88.

EXAMPLE 79 cyclo[Lys-Tyr-Lys(iPr)-DArg-2Nal-Gly-DGlu]-Lys(iPr)-$NH_2$ (SEQ ID NO:94)

Prepare as in Example 25, except that Fmoc-Arg(Pbf) in step 1 is replaced with Fmoc-Lys(iPr)(Boc), and Fmoc-Gly in step 8 is replaced with Fmoc-Lys(Boc). MW cal.: 1170.50; MW obs.: 1169.80.

EXAMPLE 80 cyclo[Phe-Tyr-Lys-DArg-2Nal-Gly-DGlu]-Lys(iPr)-$NH_2$ (SEQ ID NO:95)

Prepare as in Example 25, except that Fmoc-Arg(Pbf) in step 1 is replaced with Fmoc-Lys(iPr)(Boc), Fmoc-Lys(iPr)(Boc) in step 6 is replaced with Fmoc-Lys(Boc), and Fmoc-Gly in step 8 is replaced with Fmoc-Phe. MW cal.: 1147.40; MW obs.: 1146.70.

EXAMPLE 81 cyclo[Phe-Tyr-Lys(iPr)-DArg-2Nal-Gly-DGlu]-Lys-$NH_2$ (SEQ ID NO:96)

Prepare as in Example 25, except that Fmoc-Arg(Pbf) in step 1 is replaced with Fmoc-Lys(Boc), and Fmoc-Gly in step 8 is replaced with Fmoc-Phe. MW cal.: 1147.40; MW obs.: 1146.70.

EXAMPLE 82 cyclo[Phe-Tyr-Lys(iPr)-DArg-2Nal-Gly-DGlu]-Orn-$NH_2$ (SEQ ID NO:97)

Prepare as in Example 25, except that Fmoc-Arg(Pbf) in step 1 is replaced with Fmoc-Orn(Boc), and Fmoc-Gly in step 8 is replaced with Fmoc-Phe. MW cal.: 1133.40; MW obs.: 1132.70.

EXAMPLE 83 cyclo[Phe-Tyr-Lys-DArg-2Nal-Gly-DGlu]-Lys-$NH_2$ (SEQ ID NO:98)

Prepare as in Example 25, except that Fmoc-Arg(Pbf) in step 1 and Fmoc-Lys(iPr)(Boc) in step 6 are each replaced with Fmoc-Lys(Boc), and Fmoc-Gly in step 8 is replaced with Fmoc-Phe. MW cal.: 1105.37; MW obs.: 1105.40.

EXAMPLE 84 cyclo[Phe-Tyr-Lys-DArg-2Nal-Gly-DGlu]-Lys-NHEt (SEQ ID NO:99)

Prepare as in Example 25, except that Rink resin is replaced with [3-({ethyl-Fmoc-amino}-methyl)-indol-1-yl]-acetyl AM resin, Fmoc-Arg(Pbf) in step 1 and Fmoc-Lys(iPr)(Boc) in step 6 are each replaced with Fmoc-Lys(Boc), and Fmoc-Gly in step 8 is replaced with Fmoc-Phe. MW cal.: 1133.36; MW obs.: 1133.82.

EXAMPLE 85

Alternative Synthesis I of cyclo[Phe-Tyr-Lys(iPr)-DArg-2Nal-Gly-DGlu]-Lys(iPr)-$NH_2$ (SEQ ID NO:70)

Example 57 discloses the synthesis of SEQ ID NO:70 via Fmoc solid phase peptide synthesis chemistry employing the commercially available building block Fmoc-Lys(iPr)Boc, which is expensive and difficult to obtain in large quantity. The process described in this example permits the synthesis of SEQ ID NO:70 using less expensive Fmoc-Lys(Boc), solution cyclization, and lysine alkylation through reductive amination using sodium cyanoborohydride, providing a more economical route to this end product. Additional advantages are that the reaction media (acetic acid, acetone, and methanol) are relatively inexpensive, the reaction conditions are easily controlled, the ratio of solvents can vary significantly without affecting the alkylation reaction, and the recovery yield is 90% or higher.

The sequence Phe-Tyr(tBu)-Lys(Boc)-DArg(Pbf)-2Nal-Gly-DGlu(Oallyl)-Lys(Boc) (SEQ ID NO:100) is assembled on Rink Amide Resin by standard Fmoc chemistry utilizing an ABI 431 Peptide Synthesizer as outlined in Scheme 7. The automated assembly is carried out using the standard Applied Biosystems DCC/HOBt chemistry protocol or FastMoc chemistry (HBTU/DIEA) protocol following the supplier's directions (PE Applied Biosystems Inc., Foster City, Calif.). The side chain protecting group scheme is: Lys(Boc), DGlu (Oallyl), DArg(Pbf), Tyr(tBu). The stepwise chain assembly starts from the C-terminal end of the linear peptide and is accomplished in 8 steps. In step 1, four equivalents of protected amino acid Fmoc-Lys(Boc) are activated with DCC/HOBt (or HBTU/DIEA for FastMoc chemistry) in NMP, and coupled to deprotected Rink amide resin. In step 2, four equivalents of Fmoc-DGlu(Oallyl) are activated and coupled to the deprotected peptide resin from step 1. These steps are repeated appropriately until step 8, the coupling of Fmoc-Phe.

The allyl ester side chain protecting group is removed with 0.1 equivalent of $Pd(Ph_3P)_4$ in the presence of 24 equivalents of phenylsilane in dichloromethane (Scheme 8). This process is repeated once for complete side chain deprotection. Fmoc at the N-terminal end is then removed using 20% piperidine in DMF. The deprotected carboxylic acid moiety of DGlu is activated with PyBOP/DIEA and cyclized to the α-amino group of Phe on the resin. The cyclized peptide is simultaneously deprotected and cleaved from the resin using a scavenger cocktail of TFA/$H_2O$/TIS/EDT (95/2/1/2, v/v/v/v) or TFA/$H_2O$/TIS/anisole (92/2/4/2, v/v/v/v) for 2 hours at room temperature. The solvents are then evaporated under vacuum, and the peptide is precipitated and washed three times with cold diethyl ether to remove the scavengers.

Scheme 7.
Peptide chain assembly on solid phase

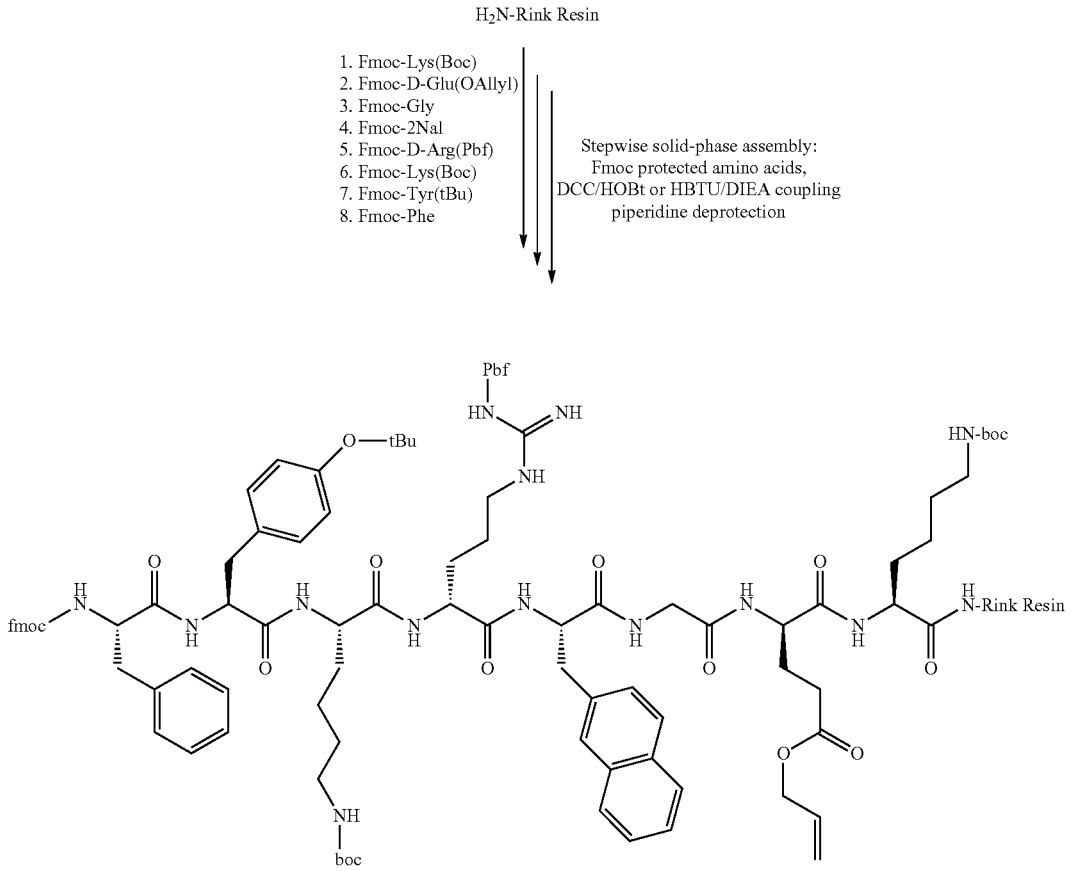

(SEQ ID NO: 100)

Scheme 8.
Preparation of cyclic precursor peptide
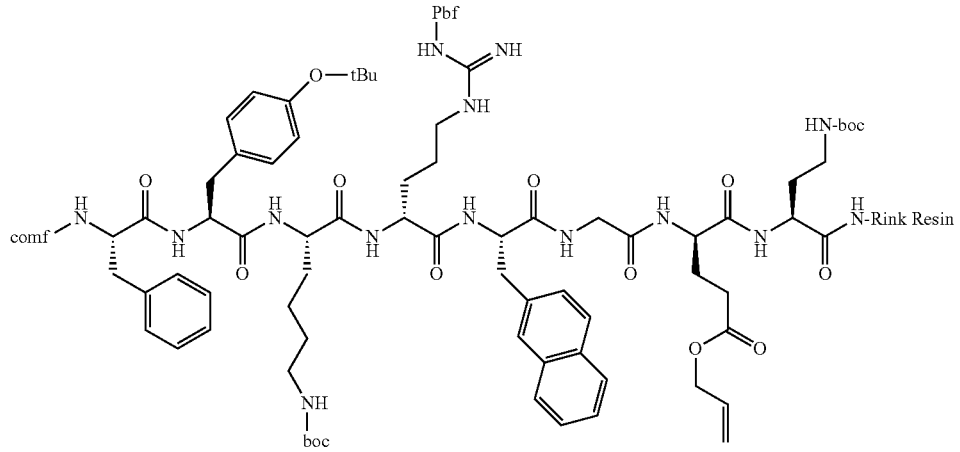
(SEQ ID NO: 100)
1. Allyl removal with Pd(PPh3)4(0)
2. Fmoc removal with piperidine
3. Cyclization with PyBOP/DIEA
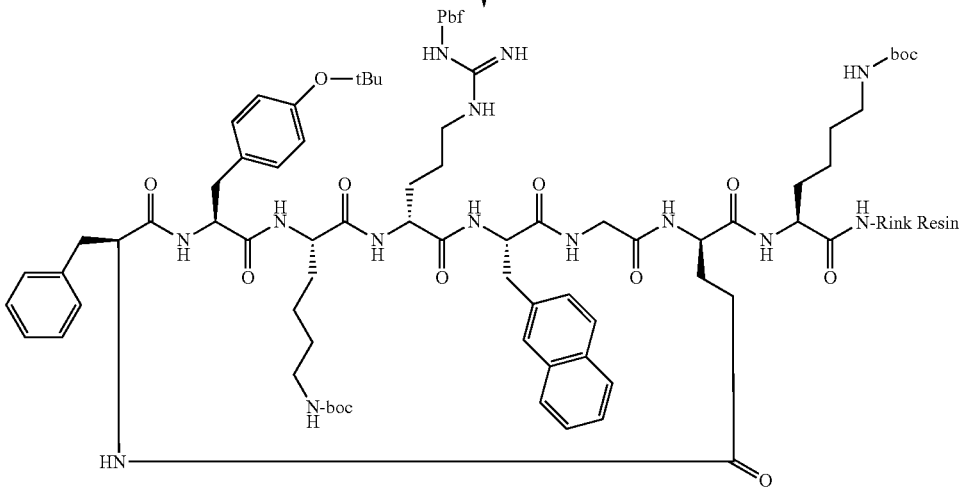
(SEQ ID NO: 101)
Side chain deprotection and TFA cleavage
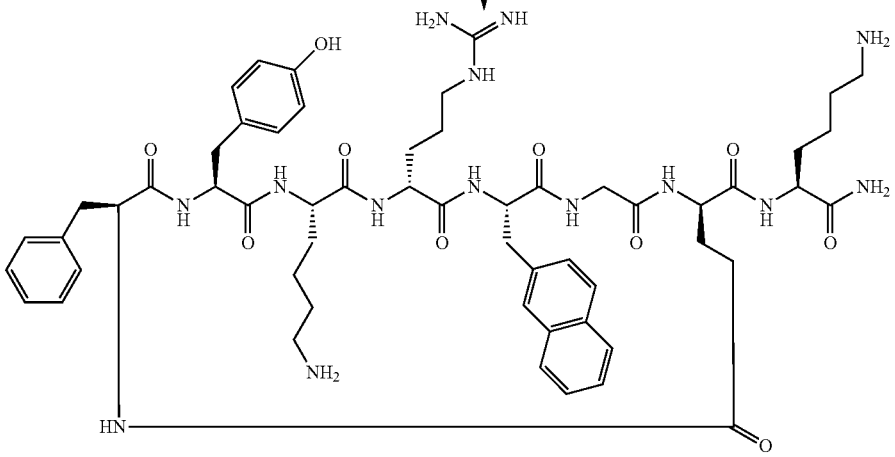
(SEQ ID NO: 98)

Purification of the cyclic precursor peptide is accomplished using standard preparative HPLC techniques. The crude cleavage product is dissolved in a minimum amount of DMSO, loaded onto a reversed phased C18 HPLC column, and eluted with an aqueous 0.1% trifluoroacetic acid/acetonitrile gradient (v/v) while monitoring at 214 nm. The appropriate fractions are pooled and lyophilized. Further characterization of the intermediate precursor cyclic peptide is performed using analytical HPLC and mass spectral analysis by conventional techniques.

The lyophilized precursor cyclic peptide is then alkylated in a solution of acetic acid/acetone/methanol (1:1:4, v/v/v) through reductive amination using sodium cyanoborohydride (Scheme 9). Peptide concentration is about 10 mg/mL, and can vary significantly without affecting the results. Three to 5 equivalents of the reducing reagent sodium cyanoborohydride are used, and the reaction is normally completed within 2 h at room temperature. The recovery yield is 90% or higher. For example, 20 mg of the precursor cyclic peptide are dissolved in 2 mL of methanol, to which 0.5 mL of acetic acid and 0.5 mL of acetone are added, mixed well, and then 5.6 mg of sodium cyanoborohydride (2.5 equivalents in methanol) are added under stirring. The reaction mixture is stirred at room temperature for 30 min, upon which another 5.6 mg of sodium cyanoborohydride are added. The reaction is monitored by HPLC and mass spectral analysis. After the reaction is complete, desalting of the reaction mixture and lyophilization yields 18.9 mg of final product (SEQ ID NO:70) with a purity of 97.5%. MW cal.: 1189.48; MW obs.: 1189.6.

Scheme 9.
Reductive amination converting Lys to Lys(iPr)

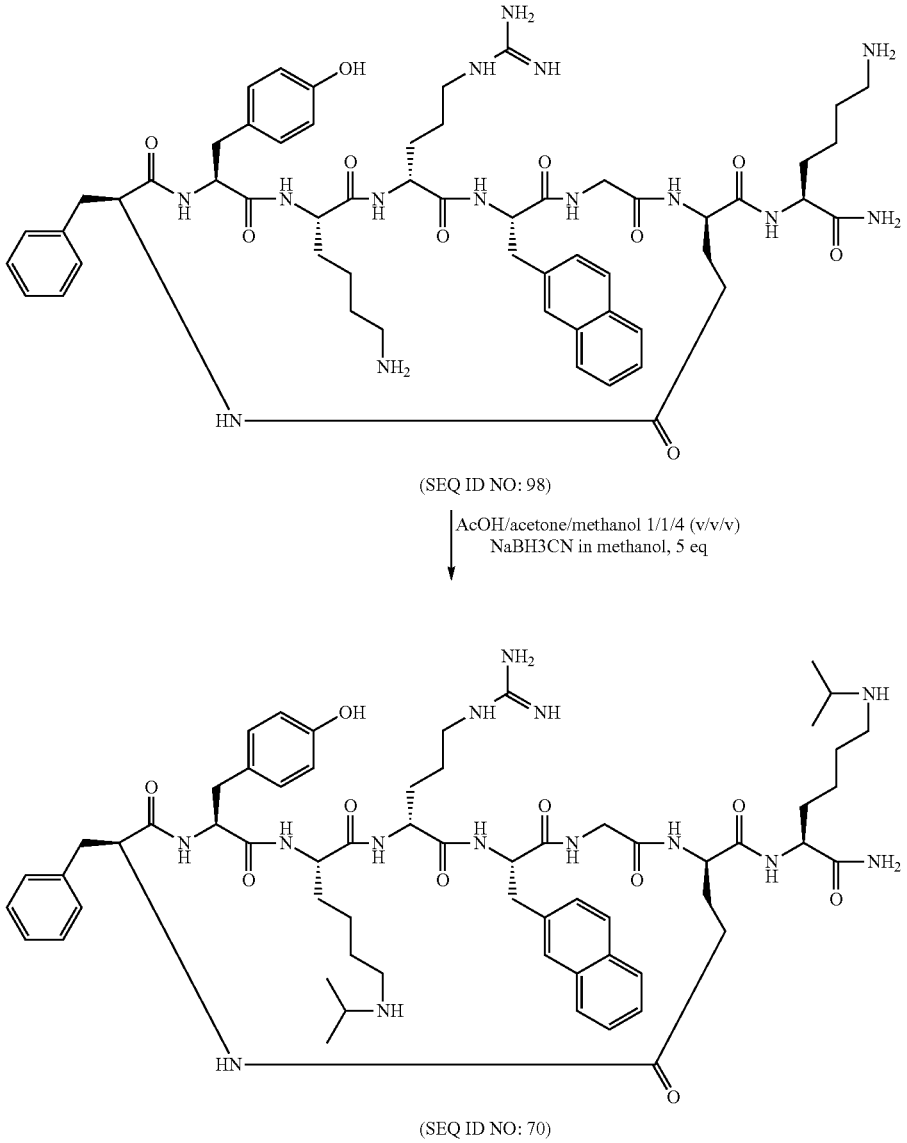

The compound of Example 60 (SEQ ID NO:74) can also be prepared in an analogous manner, with appropriate modifications based on its constituent amino acids, using [3-({ethyl-Fmoc-amino}-methyl)-indol-1-y]-acetyl AM resin. First, the precursor peptide (SEQ ID NO:99) is prepared as described in Example 84, and then reductive amination is carried out as shown in Scheme 9. This affords a final cyclic C-terminal ethyl amide peptide with a purity of 99.16%. MW cal.: 1217.53; MW obs.: 1217.84.

EXAMPLE 86

Alternative Synthesis II of cyclo[Phe-Tyr-Lys(iPr)-DArg-2Nal-Gly-DGlu]-Lys(iPr)-$NH_2$ (SEQ ID NO:70)

Example 85 discloses a cost effective synthesis of SEQ ID NO:70 via Fmoc solid phase peptide synthesis chemistry employing relatively inexpensive Fmoc-Lys(Boc) and alkylation of lysine through reductive amination using sodium cyanoborohydride in relatively inexpensive solvents (acetic acid, acetone, and methanol). However, this process involves the use of the heavy metal catalyst palladium for the removal of the allyl ester side chain protective group. Palladium is highly toxic, and quality control to insure complete removal of this element is complicated and difficult. The Boc solid phase peptide synthesis process with cyclization on the resin described in this example permits the production of SEQ ID NO:70 using relatively inexpensive Boc-Lys(2-Cl-Z) without the need for a toxic and expensive palladium catalyst, providing an even more economical, easily upscalable, less toxic route to an end product requiring a simpler quality control process.

The sequence Fmoc-Phe-Tyr(2-Br-Z)-Lys(2-Cl-Z)-DArg(Tos)-2Nal-Gly-DGlu(OFm)-Lys(2-Cl-Z) (SEQ ID NO:102) is manually assembled on MBHA (4-methyl-benzhydrylamine) resin (Cat. No. D-2095, BaChem California Inc., Torrance, Calif.) using established solid phase peptide synthesis Boc chemistry (Schnolzer et al. (1992) Int. J. Pept. Protein Res. 40:180-193) as outlined in Scheme 10. The chain assembly is carried out using an in situ neutralization/HBTU/DIEA activation procedure as described in this reference. The side chain protecting group scheme is: Lys(2-Cl-Z), DGlu(OFm), DArg(Tos), and Tyr(2-Br-Z). The alpha-amino group of all the amino acid building blocks is protected with tert-butoxycarbonyl (Boc) except the N-terminal residue Phe, which is protected with Fmoc for efficiency of synthesis. The stepwise chain assembly starts from the C-terminal end of the linear peptide and is accomplished in 8 steps. In step 1, five equivalents of protected amino acid Boc-Lys(2-Cl-Z) are activated with HBTU/DIEA in DMF, and coupled to MBHA resin. In step 2, five equivalents of Boc-DGlu(OFm) are activated and coupled to the deprotected peptide resin from step 1 using neat TFA. These steps are repeated appropriately until step 8, the coupling of Fmoc-Phe.

The Fm side chain protecting group of DGlu, together with the Fmoc at the N-terminal end, is removed using 20% piperidine in DMF. The deprotected carboxylic acid moiety of DGlu is activated with PyBOP/DIEA, HCTU/DIEA, or other appropriate activation reagents, and cyclized to the α-amino group of Phe on the resin. The cyclic peptide is simultaneously deprotected and cleaved from the resin using HF with 5% m-cresol or p-cresol as a scavenger for 1 hour at 0° C. The solvents are then evaporated and the crude peptide is precipitated and washed three times with cold diethyl ether.

Scheme 10.
Peptide chain assembly on solid phase using Boc chemistry

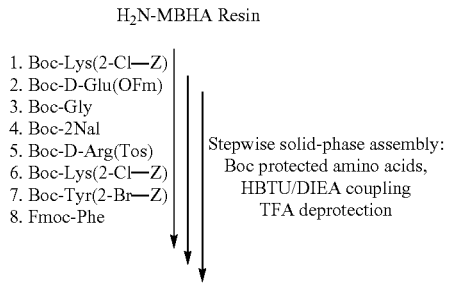

-continued

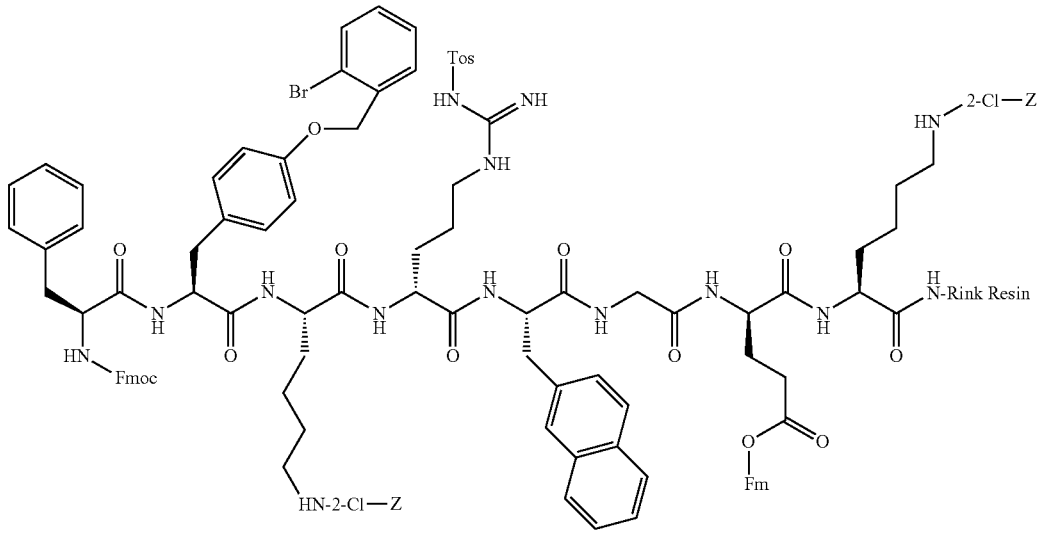

(SEQ ID NO: 102)

a. piperidine (20%) in DMF
b. cyclization, PyBOP/DIEA
c. HF cleavage, 0° C., 1 h

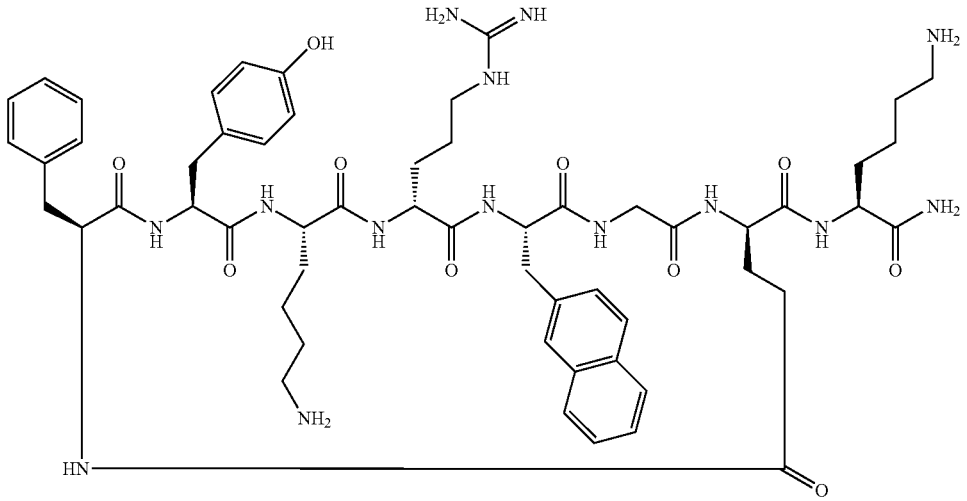

(SEQ ID NO: 98)

Purification of the cyclic precursor peptide (SEQ ID NO:98 as shown in Scheme 10) is accomplished using standard preparative HPLC techniques. The crude cleavage product is dissolved in a minimum amount of DMSO, loaded onto a reversed phased C18 HPLC column, and eluted with an aqueous 0.1% trifluoroacetic acid/acetonitrile gradient (v/v) while monitoring at 214 nm. The appropriate fractions are pooled and lyophilized. Further characterization of the intermediate precursor cyclic peptide is performed using analytical HPLC and mass spectral analysis by conventional techniques. For SEQ ID NO:98, MW cal.: 1105.29; MW obs.: 1105.4.

The lyophilized precursor cyclic peptide (SEQ ID NO:98) is then alkylated in a solution of acetic acid/acetone/methanol (1:1:4, v/v/v) through reductive amination using sodium cyanoborohydride as in Scheme 9. Peptide concentration is about 10 mg/mL, and can vary significantly without affecting the results. Five equivalents of the reducing reagent sodium cyanoborohydride are used, and the reaction is normally completed within 2 h at room temperature. The recovery yield is 90% or higher. For example, 6.6 mg of the precursor cyclic peptide are dissolved in 0.8 mL of methanol, to which 0.2 mL of acetic acid and 0.2 mL of acetone are added, mixed well, and then 1.9 mg of sodium cyanoborohydride (2.5 equivalents in methanol) are added under stirring in two equal portions. The reaction mixture is stirred at room temperature for 30 min, upon which another 1.9 mg of sodium cyanoborohydride are added. The reaction is monitored by HPLC and mass spectral analysis. After the reaction is complete, desalting of the reaction mixture and lyophilization yields the final product (SEQ ID NO:70) with a purity of 96.5%. MW cal.: 1189.45; MW obs.: 1189.6.

EXAMPLE 87

Alternative Synthesis III of cyclo[Phe-Tyr-Lys(iPr)-DArg-2Nal-Gly-DGlu]-Lys(iPr)-$NH_2$ (SEQ ID NO:70)

The compound of Example 57 (SEQ ID NO:70) can also be prepared without the use of a palladium catalyst via solution cyclization, facilitating scaleup, as follows.

The sequence Boc-Phe-Tyr(2-Br-Z)-Lys(Fmoc)-DArg(Tos)-2Nal-Gly-DGlu(OBzl)-Lys(Fmoc) (SEQ ID NO:103) is manually assembled on MBHA resin using solid phase peptide synthesis Boc chemistry (Schnolzer et al. (1992) Int. J. Pept. Protein Res. 40:180-193) as outlined in Scheme 11. The chain assembly is carried out using the in situ neutralization/HBTU/DIEA activation procedure as described in Schnolzer et al. The side chain protecting group scheme is: Lys(Fmoc), DGlu(OBZl), DArg(Tos), Tyr(2-Br-Z). The alpha-amino group of all the amino acid building blocks is protected with tert-butoxycarbonyl (Boc). The stepwise chain assembly starts from the C-terminal end of the linear peptide and is accomplished in 8 steps as shown in Scheme 11. In step 1, five equivalents of protected amino acid Boc-Lys(2-Cl-Z) are activated with HBTU (4 eq)/DIEA (10 eq) in DMF, and coupled to MBHA resin. In step 2, five equivalents of Boc-DGlu(OBzl) are activated and coupled to the deprotected peptide resin from step 1 using neat TFA. These steps are repeated appropriately until step 8, the coupling of Boc-Phe. The Boc protecting group is removed with neat TFA, the resin is neutralized with DIEA, and washed with DMF and methanol and dried in air before HF cleavage. The linear peptide is simultaneously deprotected and cleaved from the resin using HF with 5% m-cresol or p-cresol as a scavenger for 1 hour at 0° C. The solvents are then evaporated and the crude peptide is precipitated and washed three times with cold diethyl ether.

Scheme 11.
Chain assembly using Boc chemistry

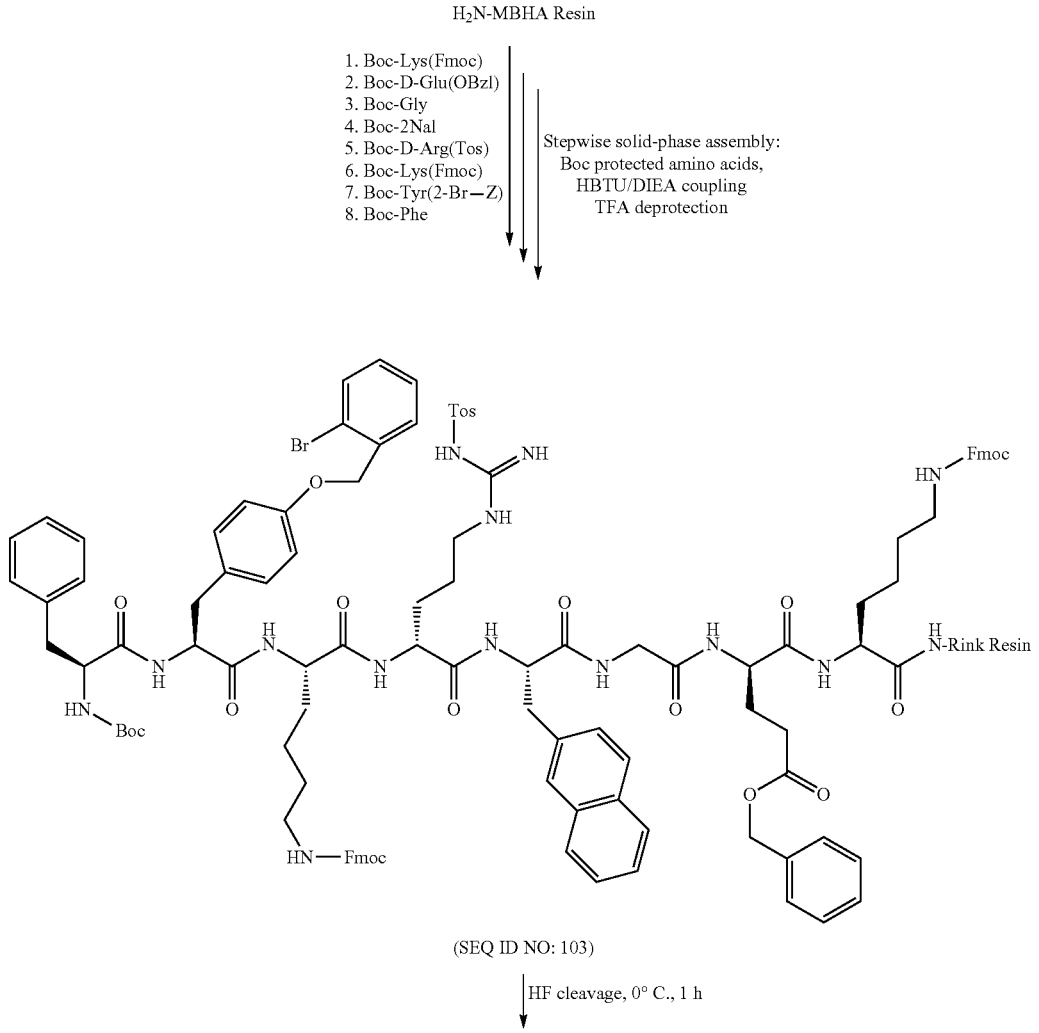

-continued

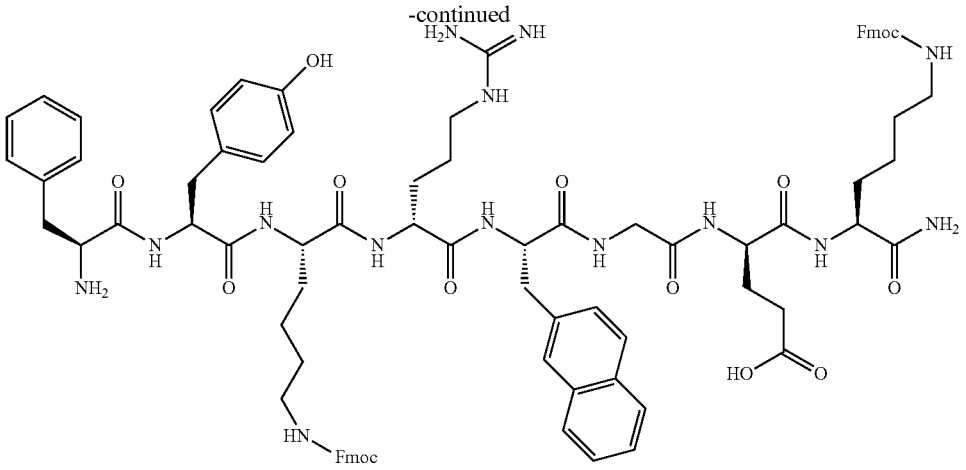

(SEQ ID NO: 104)

Purification of the linear precursor peptide (SEQ ID NO:104) is accomplished using standard preparative HPLC techniques. The crude cleavage product is dissolved in a minimum amount of DMSO, loaded onto a reversed phased C18 HPLC column, and eluted with an aqueous 0.1% trifluoroacetic acid/acetonitrile gradient (v/v) while monitoring at 214 nm. The appropriate fractions are pooled and lyophilized. Further characterization of the intermediate precursor cyclic peptide is performed using analytical HPLC and mass spectral analysis by conventional techniques. For SEQ ID NO:104, MW cal.: 1567.78; MW obs.: 1567.6.

Cyclization of the lyophilized precursor linear peptide (SEQ ID NO:104) is carried out in solution (Scheme 12). The linear peptide is dissolved in a small amount of dry DMF (~10 mg/mL). This peptide solution is slowly delivered via a syringe pump to the reaction mixture of PyBOP (2 eq, or other appropriate activation reagents, such as HCTU, BOP, HBTU, etc.) and DIEA (10 eq) in dry DMF under magnetic stirring. The reaction is then allowed to proceed at room temperature for 2 h. Neat piperidine is then added to the reaction mixture to a final concentration of 25% (v/v). The reaction mixture is kept under stirring for another 20 min to completely remove Fmoc protection. Solvents are evaporated under vacuum and the residue is loaded onto a preparative reversed phase C18 HPLC column, and eluted with an aqueous 0.1% trifluoroacetic acid/acetonitrile gradient (v/v) while monitoring at 214 nm. The appropriate fractions are pooled and lyophilized, and afford the cyclic precursor peptide (SEQ ID NO:98). Further characterization of the intermediate precursor cyclic peptide is performed using analytical HPLC and mass spectral analysis by conventional techniques. For SEQ ID NO:98, MW cal.: 1105.29; MW obs.: 1105.4.

Alkylation of cyclic peptide SEQ ID NO:98 is carried out in a solution of acetic acid/acetone/methanol (1:1:4, v/v/v) through reductive amination using sodium cyanoborohydride as in Scheme 9 to generate the final product (SEQ ID NO:70). MW cal.: 1189.45; MW obs.: 1189.6.

Scheme 12.
Cyclization and Fmoc removal

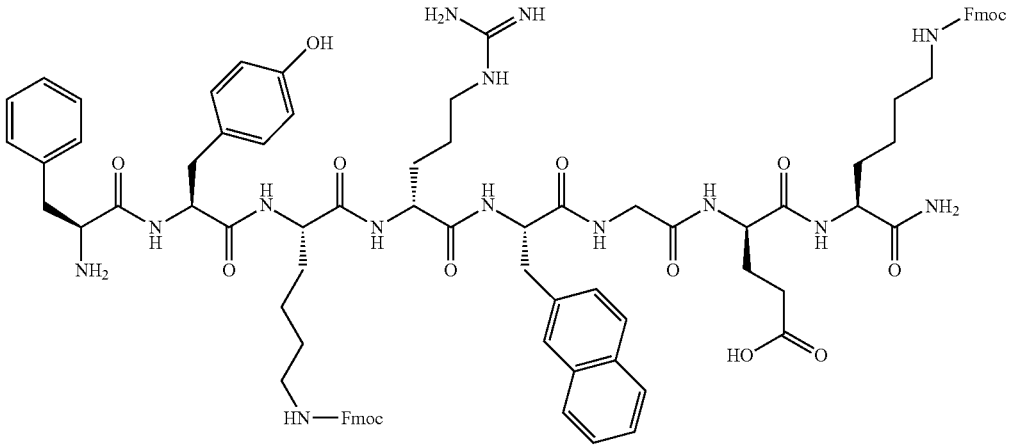

(SEQ ID NO: 104)

1. cyclization, PyBOP/DIEA/DMF
2. Fmoc removal: piperidine (20%) in DMF

-continued

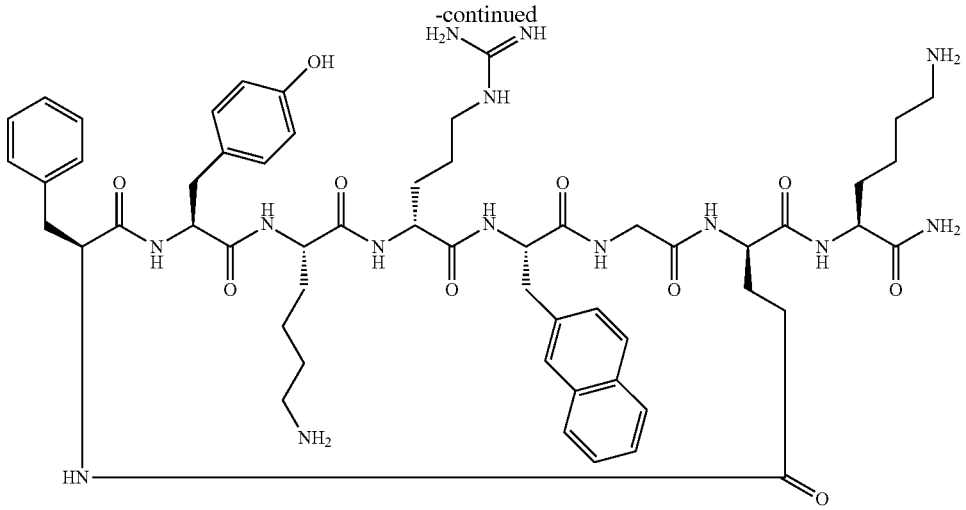

(SEQ ID NO: 98)

EXAMPLE 88

Alternative Synthesis IV of cyclo[Phe-Tyr-Lys(iPr)-DArg-2Nal-Gly-DGlu]-Lys(iPr)-$NH_2$ (SEQ ID NO:70)

The compound of Example 57 (SEQ ID NO:70) can also be prepared without the use of a palladium catalyst by the synthetic process summarized in Scheme 13 below.

The dipeptide Fmoc-DGlu-Lys(iPr,Z)-$NH_2$ is first prepared in solution with an exposed DGlutamic acid side chain. The dipeptide is linked to a hyper-acid labile CTC (2-chlorotrityl-chloride PS resin, 1% DVB (100-200 mesh) resin (Senn Chemicals USA Inc., San Diego, Calif.; catalog number 40207), and the final peptide product is then synthesized on this resin via standard Fmoc synthesis as described above. Selective removal of the peptide from the CTC resin allows only the DGlutamic acid side chain to react with the N-terminus of the peptide in solution and generate the cyclic peptide product. Subsequently, the remaining side chains are cleaved with 95% TFA or other strong acid.

Scheme 13.
Overall synthetic scheme from Fmoc-DGlu-Lys(iPr,Z)-$NH_2$

Fmoc-D-Glu(2-CTC resin)-Lys(iPr,Z)-$NH_2$

↓

Assembly by Fmoc-SPPS

H-Phe-Tyr(tBu)-Lys(iPr,Boc)-D-Arg(Pbf)-2Nal-Gly-D-Glu(2-CTC resin-Lys(iPr,Z)-$NH_2$ (SEQ ID NO: 105)

↓

Cleavage

H-Phe-Tyr(tBu)-Lys(iPr,Boc)-D-Arg(Pbf)-2Nal-Gly-D-Glu(OH)-Lys(iPr,Z)-$NH_2$ (SEQ ID NO: 106)

↓

-continued

Cyclization

Phe-Try(tBu)-Lys(iPr,Boc)-D-Arg(Pbf)-2Nal-Gly-D-Glu-Lys(iPr,Z)-$NH_2$ (SEQ ID NO: 107)

↓

Deprotection

Phe-Try-Lys(iPr)-D-Arg-2Nal-Gly-D-Glu-Lys(iPr)-$NH_2$ (SEQ ID NO: 70)

The dipeptide Fmoc-DGlu-Lys(iPr,Z)-$NH_2$ is first prepared as shown below (Scheme 14):

Scheme 14.
Preparation of Fmoc-DGlu-Lys(iPr,Z)-$NH_2$

Boc-Lys(iPr,Z)-OH

Aminolysis ↓

Boc-Lys(iPr,Z)-$NH_2$

Deprotection (25-50% TFA) ↓

H-Lys(iPr,Z)-$NH_2$

Fmoc-D-Glu(OtBu)-OH ↓

Fmoc-D-Glu(OtBu)-Lys(iPr,Z)-$NH_2$

Deprotection (25-50% TFA) ↓

Fmoc-D-Glu-Lys(iPr,Z)-$NH_2$

Boc-Lys(iPr,Z)-OH is reacted with NMM and IBCF in THF. After addition of $NH_4OH$, the solvents are removed by rotary evaporation and the product is taken up in ethyl acetate. The ethyl acetate phase is washed extensively with 5% $NaHCO_3$ and then with 0.1 N HCl, and then dried over anhydrous sodium sulfate. Sodium sulfate is removed by filtration and the ethyl acetate is removed by evaporation at reduced pressure. The resulting Boc-Lys(iPr,Z)-$NH_2$ is dissolved in DCM, and TFA is added. Once the reaction has proceeded to completion, the solvents are removed by rotary evaporation. H-Lys(iPr,Z)-$NH_2$ is then dissolved in DMF. The pH is adjusted to 8 with DIEA. In a separate vessel, Fmoc-DGlu (OtBu)-OH, HBTU, and HOBt are dissolved in DMF; DIEA is added to adjust the pH to 8. The two solutions are mixed, and the reaction is monitored by C18 reversed phase HPLC. The pH is monitored and adjusted, where necessary, with DIEA. The solvents are removed by rotary evaporation, and the product dissolved in ethyl acetate. The ethyl acetate phase is washed extensively with 5% $NaHCO_3$ and then with 0.1 N HCl, and then dried over anhydrous sodium sulfate. The sodium sulfate is removed by filtration and the ethyl acetate is removed by evaporation at reduced pressure. Rotary evaporation is continued until a dry residue is formed. The resulting Fmoc-DGlu(OtBu)-Lys(iPr,Z)-$NH_2$ is dissolved in DCM, and TFA is added. Once the reaction has proceeded to completion, the solvents are removed by rotary evaporation. The solid product is obtained by trituration with diethyl ether. After the precipitate is washed with ether, the product is dried in a vacuum oven.

Solid phase peptide synthesis of the final product is performed as follows. Fmoc-DGlu(OtBu)-Lys(iPr,Z)-$NH_2$ is dissolved in DCM and reacted with CTC resin in the presence of DIEA in a reaction vessel. After 3 h, the peptide-resin is washed free of reagents with DCM and Z-OSu is added. The pH is monitored and adjusted to pH 8-9 by adding DIEA if necessary. After 8 h, the peptide-resin is washed free of reagents with DCM, transferred to a polypropylene container, and dried in a vacuum oven.

The protected peptide-resin is assembled using Fmoc-chemistry as follows. The coupling cycle used is: 1) De-blocking: treatment with 25% piperidine in DMF; 2) Washing cycles with DMF, IPA and DMF again; 3) Ninhydrin test (qualitative: if positive, proceed to coupling Step 4); 4) Coupling with 2 equivalents Fmoc-amino acid in presence of HOBt/DIC in DMF; 5) Washing cycles with DMF; 6) Ninhydrin test (qualitative: if negative, proceed to next de-blocking/coupling cycle; if positive, proceed to re-coupling Step 7; if slightly positive, proceed to acetylation Step 10); 7) Re-coupling (if required), with 1 equivalent Fmoc-amino acid in the presence of HOBt, HBTU/DIEA in DMF; 8) Washing cycles with DMF; 9) Ninhydrin test (qualitative: if negative, proceed to next de-blocking/coupling cycle; if positive, proceed to acetylation Step 10); 10) Acetylation (if required) with 2% acetic anhydride in 4% DIEA in DMF; 11) Washing cycles (with DMF, IPA, and DMF again); 12) Ninhydrin test (qualitative: if positive, proceed to next de-blocking/coupling cycle). After the final coupling cycle, the peptide-resin (SEQ ID NO:105) is washed with ether and dried under vacuum.

The protected peptide-resin is washed with DCM. Cleavage of the fully protected linear peptide from the resin is performed with 2% TFA in DCM followed by filtration. The solvents are removed by rotary evaporation, and the fully linear protected peptide (SEQ ID NO:106) is precipitated by trituration with ether. The fully protected linear peptide is transferred to a polypropylene container and dried in a vacuum oven.

The fully protected linear peptide is cyclized in the presence of PyBOP, HOBt, and DIEA in DMF. The pH is maintained between pH 7-8 by addition of DIEA, if necessary. After the reaction has proceeded to completion, the solvents are removed by rotary evaporation, and the product is taken up in ethyl acetate. The ethyl acetate phase is washed extensively with 5% $NaHCO_3$ and then with 0.1 N HCl and saturated NaCl solution. It is then dried over anhydrous sodium sulfate. The sodium sulfate is removed by filtration and the ethyl acetate is removed by rotary evaporation at reduced pressure. The protected cyclic peptide (SEQ ID NO:107) is precipitated by trituration with ether and dried in a vacuum oven.

Deprotection is performed in TFA:$H_2O$:TIS. When the reaction is complete, the solvents are removed by rotary evaporation and the cyclic peptide (SEQ ID NO:70) is precipitated by trituration with ether and dried in a vacuum oven. MW cal.: 1189.48; MW obs.: 1189.50.

EXAMPLE 89

Incorporation of Isotopic Labels

Synthesis of cyclo[Phe-Tyr-Lys(iPr-$d_6$)-DArg-2Nal-Gly-DGlu]-Lys(iPr-$d_6$)-$NH_2$ (SEQ ID NO:108)

Starting with isotopically labeled acetone such as $^{13}C$-, $^{14}C$-, deuterium-, or tritium-labeled acetones as shown below, the processes of Examples 85-87 permit site-specific isotopic labeling of cyclic peptide CXCR4 antagonists for various pharmacological and imaging studies. The isotopically labeled acetones are commercially available from various sources. An example is given below using acetone-$d_6$ to prepare a peptide containing 12 deuterium atoms. The resulting compound, differing in molecular weight by 12 Da compared to the non-labeled counterpart, is easily differentiated in mass spectra and exhibits identical target receptor affinity.

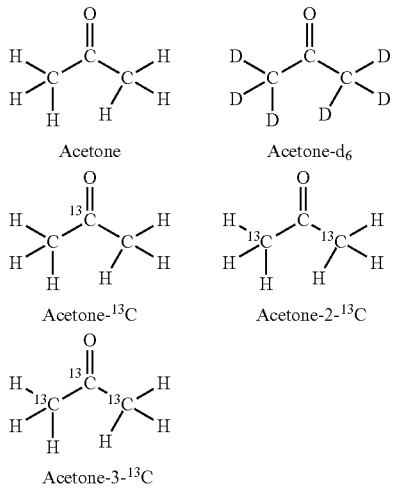

Using any of the methods in Examples 85-87, one can prepare and purify cyclic peptide precursors (SEQ ID NO:98, SEQ ID NO:99, etc.). Alkylation is carried out in a solution of acetic acid/acetone/methanol (1:1:4, v/v/v) through reductive amination using sodium cyanoborohydride as in Scheme 9, with the exception that standard acetone is replaced with the desired isotopically labeled acetone. In the present example, deuterium acetone-d6 is used Peptide (97 mg) is dissolved in 15 mL of acetic acid/acetone-$d_6$/methanol (1:1:4, v/v/v). Peptide concentration can vary significantly without affecting the results. Five equivalents of sodium cyanoborohydride are used, and the reaction is normally completed within 2 h at room temperature. The reaction is monitored by HPLC and mass spectral analysis. After the reaction is complete, desalting of the reaction mixture and lyophilization yields 90.5 mg of final product (SEQ ID NO:108) with a purity of 99.9%. MW cal.: 1201.48; MW obs.: 1201.7.

Scheme 15.
Site-specific deuterium labeling of CXCR4 antagonist

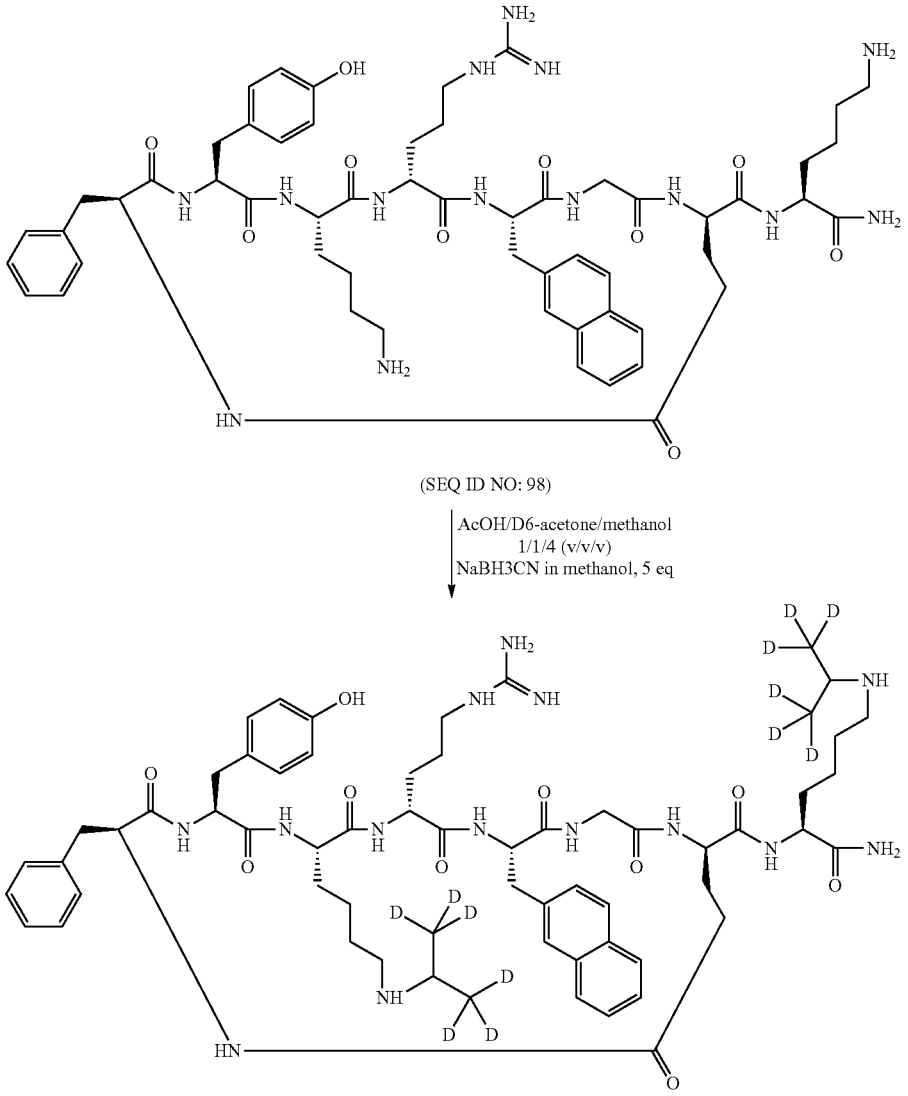

Use of isotopically labeled sodium cyanoborohydride (such as NaBD3CN, NaBT3C N, etc.) permits incorporation of additional variations to the site-specific labeling patterns.

The pharmacological properties of the present compounds can be determined by employing the assays described below.

Human CXCR4/$^{125}$I-SDF-1α Binding Inhibition Assay

SDF-1 binding to CXCR4 is the first step in activating the CXCR4 intracellular signalling pathway. To determine if a compound can block the interaction of SDF-1 and CXCR4, human leukemia CCRF-CEM cells (ATCC CCL 119) expressing endogenous CXCR4 are employed in an $^{125}$I-labeled SDF-1α binding assay. The assay is performed in a 96-well U-bottom, non-treated polystyrene plate (Corning Incorporated, Costar, No. 3632). The binding assay buffer is prepared with RPMI 1640 medium (Gibco, Grand Island, N.Y.) containing 10 mM HEPES, pH 7.5, and 0.2% BSA. Briefly, 200 μL reaction mixtures containing 300 pM SDF ligand (60 pM $^{125}$I-SDF-1α (Perkin Elmer) and 240 pM cold SDF-1α (R&D Systems), different concentrations of the test compound in assay buffer, 100,000 human CCRF-CEM cells, and 0.5 mg SPA beads (Wheatgerm agglutinin beads; Amersham) are incubated at room temperature for 2 hr. Plates are then counted in a 1450 Microbeta Liquid Scintillation and Luminescence Counter (Wallac) in SPA mode. CXCR4 antagonists decrease the bound radioactivity in this assay in a dose-dependent manner. The inhibitory potency ($K_1$ or $IC_{50}$) of a test compound is calculated using GraphPad Prism software, based on the dose-dependent decrease of bound radioactivity.

All compounds exemplified above exhibit an average $K_i$ value of about 7.5 nM or less in this assay. For example, the compound of Example 1 exhibits an average $K_i$ of 3.45 nM in this assay. Many of these compounds exhibit an average $K_i$ value between about 0.2 nM and about 1 nM. For example, the compound of Example 50 exhibits an average $K_i$ value of 0.285 nM in this assay. Other compounds exhibit an average $K_i$ value less than about 0.2 nM. For example, the compound of Example 75 exhibits an average $K_i$ value of 0.096 nM in this assay.

Chemotaxis Assay

CXCR4/SDF-1 interaction regulates migration (chemotaxis) of cells bearing CXCR4 on their surface. To determine the antagonist and cellular activities of a test compound, a chemotaxis assay using human histiocytic lymphoma U937 cells (ATCC CRL 1593) that express endogenous CXCR4 are employed. Briefly, U937 cells, grown in DMEM medium (Gibco, Grand Island, N.Y.) containing 10% FBS, 1% MEM sodium pyruvate (Gibco), 1% MEM nonessential amino acids (Gibco), and 1% GlutaMAX 1 (Gibco), are harvested and washed once with chemotaxis assay buffer prepared with 1×RPMI medium (Gibco) containing 10 mM HEPES, pH 7.5, and 0.3% BSA. After washing, cells are resuspended in assay buffer at a concentration of $5\times10^6$ cells/mL. The assay is performed in a 96-well ChemoTx plate (NeuroProbe) according to the manufacturer's directions. Generally, 50 μL of cell mixture with or without test compound are plated on the upper chamber, and 30 μL of SDF-1α (R&D Systems, 10 ng/mL) prepared in 1× chemotaxis buffer are added to the lower chamber. After assembly, the plate is incubated for 2.5 hr at 37° C. under 5% $CO_2$. Following the incubation, 5 μL of CellTiter 96 AQ (Promega, Madison, Wis.) are added into the lower chamber. The plate is then incubated for 60 min at 37° C., and the migrated cells are detected by measuring the absorbance at 492 nm with a Tecan Spectrafluor Plus Microplate Reader (Salzburg, Austria). CXCR4 antagonists inhibit cell migration, reducing the absorbance reading. The inhibitory potency ($IC_{50}$) of a test compound in this assay is calculated using GraphPad Prism software, based on the dose-dependent decrease of absorbance at 492 nm.

Most of the compounds exemplified above exhibit an average $IC_{50}$ value of about 60 nM or less in this assay. Many of these compounds exhibit an average $IC_{50}$ value of about 6 nM or less, e.g., the compound of Example 19 exhibits an average $IC_{50}$ value of 2.05 nM in this assay. Many of these compounds exhibit an average $IC_{50}$ value of about 0.6 nM or less, e.g., the compound of Example 50 exhibits an average $IC_{50}$ value of 0.171 nM in this assay.

Chemokine Receptor Binding Selectivity Assays

The binding selectivity of the present compounds for the CXCR4 receptor compared to that for other chemokine receptors, such as human CCR1, CCR2, CXCR2, or CXCR3, and other G-protein-coupled receptors, can be assessed in cells transfected with nucleic acid encoding and expressing such receptors, or in cells in which such receptors are endogenously expressed. Whole cells or membrane fragments can be used to assess competition of test compounds with the respective ligands for these receptors in a manner similar to that described above for the CXCR4/$^{125}$I-SDF-1α binding inhibition assay.

For example, the compound of Example 57a exhibits a $K_i$ value greater than 73,000 nM in a ligand binding assay using human chemokine receptor CXCR2.

Compound-Induced White Blood Cell and Neutrophil Mobilization in C57BL/6 Mice

Stem cells within the bone marrow actively maintain continuous production of all mature blood cell lineages throughout life. Bone marrow is the primary site for white blood cell (WBC)/neutrophil production and release into the circulation. The CXCR4/SDF-1 axis appears to be critical for the retention and release of WBCs, neutrophils, and hematopoietic progenitor cells in the bone marrow, and interruption of CXCR4/SDF-1 interaction in bone marrow leads to an increase of these cells in peripheral blood. A short-term mouse WBC/neutrophil mobilization model can be used to determine the in vivo target-modulating activity of a test compound. Briefly, pathogen-free 5-6 week old female C57BL/6 mice (Taconic) are housed for at least one week prior to assay. Animals are allowed continuous access to sterilized rodent chow and acidified water. Groups of 5 mice are injected subcutaneously with test compounds in saline, or with saline control, and then sacrificed by $CO_2$ asphyxiation and cervical dislocation at various time points post compound administration. Peripheral blood is collected by cardiac puncture using EDTA-coated syringes and tubes. Complete blood cell analysis is performed on a Hemavet Mascot hematology analyzer (Drew Scientific Group, Dallas, Tex.). Total WBCs, neutrophils, and lymphocytes in the peripheral blood are recorded. Effective CXCR4 antagonists administered subcutaneously to mice increase the neutrophil and WBC counts in peripheral blood compared to saline control.

A significant number of compounds exemplified above exhibit an average neutrophil ratio (ratio of neutrophil increase in treatment group vs. neutrophil increase in saline control group), measured 3 hours after compound administration, greater than about 2 in this assay. For example, the compound of Example 39 exhibits an average neutrophil ratio of 4.6 at a dose of 5 mg/kg in this assay.

Anti-Tumor Activity in a SCID/Namalwa Xenograft Model

SDF-1/CXCR4 interaction appears to play an important role in multiple stages of tumorigenesis, including tumor growth, invasion, angiogenesis, and metastasis. To evaluate in vivo anti-tumor activity of a test compound, a tumor xenograft model using NOD/SCID mice (Jackson Laboratories) and human non-Hodgkin's lymphoma Namalwa cells (ATCC CRL 1432) are employed. Briefly, 200,000 Namalwa cells mixed with matrigel (1:1) are implanted subcutaneously into the rear flank of the animals. The implanted tumor cells grow as solid tumors, the dimensions of which can be continuously monitored and measured using a caliper. To determine the in vivo efficacy of a test compound in this model, one can treat animals (10/group) with different doses of test compounds dissolved in saline or PBS, beginning 48 hours post tumor cell implantation. Compounds are dosed subcutaneously, and tumor volume and body weight are determined every 2 or 3 days. Studies generally last 3-4 weeks, depending on tumor growth. The anti-tumor growth activity of a test compound is determined by the percent reduction in tumor volume in treatment groups compared to tumor volume in control groups treated with vehicle alone.

Several compounds exemplified above, for example the compound of Example 26, significantly inhibit tumor growth in this assay when administered at 1 mg/kg BID.

Pharmacologic properties such as compound bioavailability, in vivo metabolic stability, and pharmacokinetic/pharmacodynamic properties can be determined by methods well known in the art of drug development. Preferred compounds of the present invention exhibit high bioavailability when administered subcutaneously. Some compounds exemplified herein exhibit bioavailability near 100% in rats, for example the compound of Example 44. Preferred compounds also exhibit good in vivo metabolic stability. For example, no detectable metabolites are observed in dog and monkey plasma and urine up to 24 hours after administration of the compound of Example 57a. Preferred compounds also exhibit favorable pharmacokinetic/pharmacodynamic properties that permit convenient dosing. For example, in mice, the half-life (T½) of the compound of Example 58 is about 3 hours. With respect to pharmacodynamic properties, preferred compounds induce prolonged neutrophil and white blood cell mobilization in mice. For example, the compound of Example 25 induces a significant increase of neutrophils and white blood cells in peripheral blood for at least 6 hours after single dose subcutaneous administration at 5 mg/kg in mice.

SEQUENCE LISTING

```
<160> NUMBER OF SEQ ID NOS: 108

<210> SEQ ID NO 1
<211> LENGTH: 10
<212> TYPE: PRT
<213> ORGANISM: Artificial
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: Ac, Bz or n-hexanoyl or is absent
<220> FEATURE:
<221> NAME/KEY: MOD_RES
<222> LOCATION: (1)..(7)
<223> OTHER INFORMATION: Lactam bridge, when Xaa at position 1 is
      present
<220> FEATURE:
<221> NAME/KEY: MISC_FEATURE
<222> LOCATION: (1)..(1)
<223> OTHER INFORMATION: Xaa = d or l isomer Agl, Dab, Dap, Asp, Glu,
      Ala, d isomer Ala, Gly, Dap(Ac), Leu, Lys, Lys(Ac), 2Nal, Phe, d
      isomer Phe, beta-Ala or is absent
<220> FEATURE:
<221> NAME/KEY: MOD_RES
<222> LOCATION: (2)..(7)
<223> OTHER INFORMATION: Lactam bridge, when Xaa at position 1 is absent
<220> FEATURE:
<221> NAME/KEY: MOD_RES
<222> LOCATION: (2)..(2)
<223> OTHER INFORMATION: 5-amino-valeryl, 4-AMB, 4-AMPA, succinyl or is
      absent
<220> FEATURE:
<221> NAME/KEY: MISC_FEATURE
<222> LOCATION: (3)..(3)
<223> OTHER INFORMATION: Xaa = Arg, Lys, Lys(iPr) or Lys(Me2)
<220> FEATURE:
<221> NAME/KEY: MOD_RES
<222> LOCATION: (4)..(4)
<223> OTHER INFORMATION: d isomer
<220> FEATURE:
<221> NAME/KEY: MISC_FEATURE
<222> LOCATION: (5)..(5)
<223> OTHER INFORMATION: Xaa = 2Nal
<220> FEATURE:
<221> NAME/KEY: MISC_FEATURE
<222> LOCATION: (7)..(7)
<223> OTHER INFORMATION: Xaa = Glu, d or l isomer Agl, Dab, Dap, d
      isomer Dap, Lys, Orn, d isomer Glu, or Asp
<220> FEATURE:
<221> NAME/KEY: MISC_FEATURE
<222> LOCATION: (8)..(8)
<223> OTHER INFORMATION: Xaa = beta-Ala, Arg, d isomer Arg, Gly, Lys,
      Lys(iPr), Orn or is absent, and when absent, Xaa at positions 9
      and 10 are also absent
<220> FEATURE:
<221> NAME/KEY: MISC_FEATURE
<222> LOCATION: (9)..(9)
<223> OTHER INFORMATION: Xaa = Gly, 2Nal, d isomer 2Nal, d isomer Phe,
      or is absent, and when absent, Xaa at position 10 is also absent
<220> FEATURE:
<221> NAME/KEY: MISC_FEATURE
<222> LOCATION: (10)..(10)
<223> OTHER INFORMATION: Xaa = 2Nal or is absent
<220> FEATURE:
<221> NAME/KEY: MOD_RES
<222> LOCATION: (10)..(10)
<223> OTHER INFORMATION: Amidated as NH2 or NHEt
```

<400> SEQUENCE: 1

Xaa Tyr Xaa Arg Xaa Gly Xaa Xaa Xaa Xaa
1 5 10

<210> SEQ ID NO 2
<211> LENGTH: 8
<212> TYPE: PRT
<213> ORGANISM: Artificial
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: Ac modified
<220> FEATURE:
<221> NAME/KEY: MOD_RES
<222> LOCATION: (1)..(7)
<223> OTHER INFORMATION: Lactam bridge
<220> FEATURE:
<221> NAME/KEY: MISC_FEATURE
<222> LOCATION: (1)..(1)
<223> OTHER INFORMATION: Xaa = Dap
<220> FEATURE:
<221> NAME/KEY: MOD_RES
<222> LOCATION: (4)..(4)
<223> OTHER INFORMATION: d isomer
<220> FEATURE:
<221> NAME/KEY: MISC_FEATURE
<222> LOCATION: (5)..(5)
<223> OTHER INFORMATION: Xaa = 2Nal
<220> FEATURE:
<221> NAME/KEY: MOD_RES
<222> LOCATION: (8)..(8)
<223> OTHER INFORMATION: AMIDATION

<400> SEQUENCE: 2

Xaa Tyr Arg Arg Xaa Gly Glu Arg
1 5

<210> SEQ ID NO 3
<211> LENGTH: 8
<212> TYPE: PRT
<213> ORGANISM: Artificial
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: Ac modified
<220> FEATURE:
<221> NAME/KEY: MISC_FEATURE
<222> LOCATION: (1)..(1)
<223> OTHER INFORMATION: Xaa = Dap(Alloc)
<220> FEATURE:
<221> NAME/KEY: MISC_FEATURE
<222> LOCATION: (2)..(2)
<223> OTHER INFORMATION: Xaa = Tyr(tBu)
<220> FEATURE:
<221> NAME/KEY: MISC_FEATURE
<222> LOCATION: (3)..(3)
<223> OTHER INFORMATION: Xaa = Arg(Pbf)
<220> FEATURE:
<221> NAME/KEY: MISC_FEATURE
<222> LOCATION: (4)..(4)
<223> OTHER INFORMATION: Xaa = d isomer Arg(Pbf)
<220> FEATURE:
<221> NAME/KEY: MISC_FEATURE
<222> LOCATION: (5)..(5)
<223> OTHER INFORMATION: Xaa = 2Nal
<220> FEATURE:
<221> NAME/KEY: MISC_FEATURE
<222> LOCATION: (7)..(7)
<223> OTHER INFORMATION: Xaa = Glu(Oallyl)
<220> FEATURE:
<221> NAME/KEY: MISC_FEATURE <222> LOCATION: (8)..(8)
<223> OTHER INFORMATION: Xaa = Arg(Pbf)

<400> SEQUENCE: 3

Xaa Xaa Xaa Xaa Xaa Gly Xaa Xaa
1 5

<210> SEQ ID NO 4
<211> LENGTH: 8
<212> TYPE: PRT
<213> ORGANISM: Artificial
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: Ac modified
<220> FEATURE:
<221> NAME/KEY: MISC_FEATURE
<222> LOCATION: (1)..(1)
<223> OTHER INFORMATION: Xaa = Dap(Alloc)
<220> FEATURE:
<221> NAME/KEY: MISC_FEATURE
<222> LOCATION: (2)..(2)
<223> OTHER INFORMATION: Xaa = Tyr(tBu)
<220> FEATURE:
<221> NAME/KEY: MISC_FEATURE
<222> LOCATION: (3)..(3)
<223> OTHER INFORMATION: Xaa = Arg(Pbf)
<220> FEATURE:
<221> NAME/KEY: MISC_FEATURE
<222> LOCATION: (4)..(4)
<223> OTHER INFORMATION: Xaa = d isomer Arg(Pbf)
<220> FEATURE:
<221> NAME/KEY: MISC_FEATURE
<222> LOCATION: (5)..(5)
<223> OTHER INFORMATION: Xaa = 2Nal
<220> FEATURE:
<221> NAME/KEY: MISC_FEATURE
<222> LOCATION: (7)..(7)
<223> OTHER INFORMATION: Xaa = Glu(OAllyl)
<220> FEATURE:
<221> NAME/KEY: MISC_FEATURE
<222> LOCATION: (8)..(8)
<223> OTHER INFORMATION: Xaa = Arg(Pbf)
<220> FEATURE:
<221> NAME/KEY: MOD_RES
<222> LOCATION: (8)..(8)
<223> OTHER INFORMATION: AMIDATION

<400> SEQUENCE: 4

Xaa Xaa Xaa Xaa Xaa Gly Xaa Xaa
1 5

<210> SEQ ID NO 5
<211> LENGTH: 8
<212> TYPE: PRT
<213> ORGANISM: Artificial
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: Ac modified
<220> FEATURE:
<221> NAME/KEY: MOD_RES
<222> LOCATION: (1)..(7)
<223> OTHER INFORMATION: Lactam bridge
<220> FEATURE:
<221> NAME/KEY: MISC_FEATURE
<222> LOCATION: (1)..(1)
<223> OTHER INFORMATION: Xaa = Dap
<220> FEATURE:
<221> NAME/KEY: MISC_FEATURE
<222> LOCATION: (2)..(2)
<223> OTHER INFORMATION: Xaa = Tyr(tBu)

<220> FEATURE:
<221> NAME/KEY: MISC_FEATURE
<222> LOCATION: (3)..(3)
<223> OTHER INFORMATION: Xaa = Arb(Pbf)
<220> FEATURE:
<221> NAME/KEY: MISC_FEATURE
<222> LOCATION: (4)..(4)
<223> OTHER INFORMATION: Xaa = d isomer Arg(Pbf)
<220> FEATURE:
<221> NAME/KEY: MISC_FEATURE
<222> LOCATION: (5)..(5)
<223> OTHER INFORMATION: Xaa = 2Nal
<220> FEATURE:
<221> NAME/KEY: MISC_FEATURE
<222> LOCATION: (8)..(8)
<223> OTHER INFORMATION: Xaa = Arg(Pbf)
<220> FEATURE:
<221> NAME/KEY: MOD_RES
<222> LOCATION: (8)..(8)
<223> OTHER INFORMATION: AMIDATION

<400> SEQUENCE: 5

Xaa Xaa Xaa Xaa Xaa Gly Glu Xaa
1 5

<210> SEQ ID NO 6
<211> LENGTH: 8
<212> TYPE: PRT
<213> ORGANISM: Artificial
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: Ac modified
<220> FEATURE:
<221> NAME/KEY: MOD_RES
<222> LOCATION: (1)..(7)
<223> OTHER INFORMATION: Lactam bridge
<220> FEATURE:
<221> NAME/KEY: MISC_FEATURE
<222> LOCATION: (1)..(1)
<223> OTHER INFORMATION: Xaa = Dab
<220> FEATURE:
<221> NAME/KEY: MOD_RES
<222> LOCATION: (4)..(4)
<223> OTHER INFORMATION: d isomer
<220> FEATURE:
<221> NAME/KEY: MISC_FEATURE
<222> LOCATION: (5)..(5)
<223> OTHER INFORMATION: Xaa = 2Nal
<220> FEATURE:
<221> NAME/KEY: MOD_RES
<222> LOCATION: (8)..(8)
<223> OTHER INFORMATION: AMIDATION

<400> SEQUENCE: 6

Xaa Tyr Arg Arg Xaa Gly Glu Arg
1 5

<210> SEQ ID NO 7
<211> LENGTH: 8
<212> TYPE: PRT
<213> ORGANISM: Artificial
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: Ac modified
<220> FEATURE:
<221> NAME/KEY: MISC_FEATURE
<222> LOCATION: (1)..(1)
<223> OTHER INFORMATION: Xaa = Dap
<220> FEATURE:
<221> NAME/KEY: MOD_RES <222> LOCATION: (1)..(7)
<223> OTHER INFORMATION: Lactam bridge
<220> FEATURE:
<221> NAME/KEY: MISC_FEATURE
<222> LOCATION: (3)..(3)
<223> OTHER INFORMATION: Xaa = Lys(iPr)
<220> FEATURE:
<221> NAME/KEY: MOD_RES
<222> LOCATION: (4)..(4)
<223> OTHER INFORMATION: d isomer
<220> FEATURE:
<221> NAME/KEY: MISC_FEATURE
<222> LOCATION: (5)..(5)
<223> OTHER INFORMATION: Xaa = 2Nal
<220> FEATURE:
<221> NAME/KEY: MOD_RES
<222> LOCATION: (8)..(8)
<223> OTHER INFORMATION: AMIDATION

<400> SEQUENCE: 7

Xaa Tyr Xaa Arg Xaa Gly Glu Arg
1 5

<210> SEQ ID NO 8
<211> LENGTH: 8
<212> TYPE: PRT
<213> ORGANISM: Artificial
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: n-Hexanoyl modified
<220> FEATURE:
<221> NAME/KEY: MOD_RES
<222> LOCATION: (1)..(7)
<223> OTHER INFORMATION: Lactam bridge
<220> FEATURE:
<221> NAME/KEY: MISC_FEATURE
<222> LOCATION: (1)..(1)
<223> OTHER INFORMATION: Xaa = Dap
<220> FEATURE:
<221> NAME/KEY: MISC_FEATURE
<222> LOCATION: (3)..(3)
<223> OTHER INFORMATION: Xaa = Lys(iPr)
<220> FEATURE:
<221> NAME/KEY: MOD_RES
<222> LOCATION: (4)..(4)
<223> OTHER INFORMATION: d isomer
<220> FEATURE:
<221> NAME/KEY: MISC_FEATURE
<222> LOCATION: (5)..(5)
<223> OTHER INFORMATION: Xaa = 2Nal
<220> FEATURE:
<221> NAME/KEY: MOD_RES
<222> LOCATION: (8)..(8)
<223> OTHER INFORMATION: AMIDATION

<400> SEQUENCE: 8

Xaa Tyr Xaa Arg Xaa Gly Glu Arg
1 5

<210> SEQ ID NO 9
<211> LENGTH: 8
<212> TYPE: PRT
<213> ORGANISM: Artificial
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: Ac modified
<220> FEATURE:
<221> NAME/KEY: MISC_FEATURE
<222> LOCATION: (1)..(1)
<223> OTHER INFORMATION: Xaa = d or l isomer Agl <220> FEATURE:
<221> NAME/KEY: MOD_RES
<222> LOCATION: (1)..(7)
<223> OTHER INFORMATION: Lactam bridge
<220> FEATURE:
<221> NAME/KEY: MOD_RES
<222> LOCATION: (4)..(4)
<223> OTHER INFORMATION: d isomer
<220> FEATURE:
<221> NAME/KEY: MISC_FEATURE
<222> LOCATION: (5)..(5)
<223> OTHER INFORMATION: Xaa = 2Nal
<220> FEATURE:
<221> NAME/KEY: MOD_RES
<222> LOCATION: (8)..(8)
<223> OTHER INFORMATION: AMIDATION

<400> SEQUENCE: 9

Xaa Tyr Arg Arg Xaa Gly Glu Arg
1 5

<210> SEQ ID NO 10
<211> LENGTH: 8
<212> TYPE: PRT
<213> ORGANISM: Artificial
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: Ac modified
<220> FEATURE:
<221> NAME/KEY: MOD_RES
<222> LOCATION: (1)..(7)
<223> OTHER INFORMATION: Lactam bridge
<220> FEATURE:
<221> NAME/KEY: MOD_RES
<222> LOCATION: (4)..(4)
<223> OTHER INFORMATION: d isomer
<220> FEATURE:
<221> NAME/KEY: MISC_FEATURE
<222> LOCATION: (5)..(5)
<223> OTHER INFORMATION: Xaa = 2Nal
<220> FEATURE:
<221> NAME/KEY: MISC_FEATURE
<222> LOCATION: (7)..(7)
<223> OTHER INFORMATION: Xaa = Dap
<220> FEATURE:
<221> NAME/KEY: MOD_RES
<222> LOCATION: (8)..(8)
<223> OTHER INFORMATION: AMIDATION

<400> SEQUENCE: 10

Glu Tyr Arg Arg Xaa Gly Xaa Arg
1 5

<210> SEQ ID NO 11
<211> LENGTH: 8
<212> TYPE: PRT
<213> ORGANISM: Artificial
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa = Glu(OtBu)
<220> FEATURE:
<221> NAME/KEY: MISC_FEATURE
<222> LOCATION: (2)..(2)
<223> OTHER INFORMATION: Xaa = Tyr(tBu)
<220> FEATURE:
<221> NAME/KEY: MISC_FEATURE
<222> LOCATION: (3)..(3)
<223> OTHER INFORMATION: Xaa = Arg(Pbf)
<220> FEATURE:
<221> NAME/KEY: MISC_FEATURE <222> LOCATION: (4)..(4)
<223> OTHER INFORMATION: Xaa = d isomer Arg(Pbf)
<220> FEATURE:
<221> NAME/KEY: MISC_FEATURE
<222> LOCATION: (5)..(5)
<223> OTHER INFORMATION: Xaa = 2Nal
<220> FEATURE:
<221> NAME/KEY: MISC_FEATURE
<222> LOCATION: (7)..(7)
<223> OTHER INFORMATION: Xaa = Dap(Boc)
<220> FEATURE:
<221> NAME/KEY: MISC_FEATURE
<222> LOCATION: (8)..(8)
<223> OTHER INFORMATION: Xaa = Arg(Pbf)

<400> SEQUENCE: 11

Xaa Xaa Xaa Xaa Xaa Gly Xaa Xaa
1 5

<210> SEQ ID NO 12
<211> LENGTH: 8
<212> TYPE: PRT
<213> ORGANISM: Artificial
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: Ac modified
<220> FEATURE:
<221> NAME/KEY: MISC_FEATURE
<222> LOCATION: (1)..(1)
<223> OTHER INFORMATION: Xaa = Glu(OtBu)
<220> FEATURE:
<221> NAME/KEY: MISC_FEATURE
<222> LOCATION: (2)..(2)
<223> OTHER INFORMATION: Xaa = Tyr(tBu)
<220> FEATURE:
<221> NAME/KEY: MISC_FEATURE
<222> LOCATION: (3)..(3)
<223> OTHER INFORMATION: Xaa = Arg(Pbf)
<220> FEATURE:
<221> NAME/KEY: MISC_FEATURE
<222> LOCATION: (4)..(4)
<223> OTHER INFORMATION: Xaa = d isomer Arg(Pbf)
<220> FEATURE:
<221> NAME/KEY: MISC_FEATURE
<222> LOCATION: (5)..(5)
<223> OTHER INFORMATION: Xaa = 2Nal
<220> FEATURE:
<221> NAME/KEY: MISC_FEATURE
<222> LOCATION: (7)..(7)
<223> OTHER INFORMATION: Xaa = Dap(Boc)
<220> FEATURE:
<221> NAME/KEY: MISC_FEATURE
<222> LOCATION: (8)..(8)
<223> OTHER INFORMATION: Xaa = Arg(Pbf)
<220> FEATURE:
<221> NAME/KEY: MOD_RES
<222> LOCATION: (8)..(8)
<223> OTHER INFORMATION: AMIDATION

<400> SEQUENCE: 12

Xaa Xaa Xaa Xaa Xaa Gly Xaa Xaa
1 5

<210> SEQ ID NO 13
<211> LENGTH: 8
<212> TYPE: PRT
<213> ORGANISM: Artificial
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: Ac modified <220> FEATURE:
<221> NAME/KEY: MOD_RES
<222> LOCATION: (4)..(4)
<223> OTHER INFORMATION: d isomer
<220> FEATURE:
<221> NAME/KEY: MISC_FEATURE
<222> LOCATION: (5)..(5)
<223> OTHER INFORMATION: Xaa = 2Nal
<220> FEATURE:
<221> NAME/KEY: MISC_FEATURE
<222> LOCATION: (7)..(7)
<223> OTHER INFORMATION: Xaa = Dap
<220> FEATURE:
<221> NAME/KEY: MOD_RES
<222> LOCATION: (8)..(8)
<223> OTHER INFORMATION: AMIDATION

<400> SEQUENCE: 13

Glu Tyr Arg Arg Xaa Gly Xaa Arg
1 5

<210> SEQ ID NO 14
<211> LENGTH: 8
<212> TYPE: PRT
<213> ORGANISM: Artificial
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: Bz modified
<220> FEATURE:
<221> NAME/KEY: MOD_RES
<222> LOCATION: (1)..(7)
<223> OTHER INFORMATION: Lactam bridge
<220> FEATURE:
<221> NAME/KEY: MOD_RES
<222> LOCATION: (4)..(4)
<223> OTHER INFORMATION: d isomer
<220> FEATURE:
<221> NAME/KEY: MISC_FEATURE
<222> LOCATION: (5)..(5)
<223> OTHER INFORMATION: Xaa = 2Nal
<220> FEATURE:
<221> NAME/KEY: MISC_FEATURE
<222> LOCATION: (7)..(7)
<223> OTHER INFORMATION: Xaa = Dap
<220> FEATURE:
<221> NAME/KEY: MOD_RES
<222> LOCATION: (8)..(8)
<223> OTHER INFORMATION: AMIDATION

<400> SEQUENCE: 14

Glu Tyr Arg Arg Xaa Gly Xaa Arg
1 5

<210> SEQ ID NO 15
<211> LENGTH: 8
<212> TYPE: PRT
<213> ORGANISM: Artificial
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: Ac modified
<220> FEATURE:
<221> NAME/KEY: MOD_RES
<222> LOCATION: (1)..(7)
<223> OTHER INFORMATION: Lactam bridge
<220> FEATURE:
<221> NAME/KEY: MOD_RES
<222> LOCATION: (4)..(4)
<223> OTHER INFORMATION: d isomer
<220> FEATURE:
<221> NAME/KEY: MISC_FEATURE <222> LOCATION: (5)..(5)
<223> OTHER INFORMATION: Xaa = 2Nal
<220> FEATURE:
<221> NAME/KEY: MISC_FEATURE
<222> LOCATION: (7)..(7)
<223> OTHER INFORMATION: Xaa = d isomer Dap
<220> FEATURE:
<221> NAME/KEY: MOD_RES
<222> LOCATION: (8)..(8)
<223> OTHER INFORMATION: AMIDATION

<400> SEQUENCE: 15

Glu Tyr Arg Arg Xaa Gly Xaa Arg
1 5

<210> SEQ ID NO 16
<211> LENGTH: 8
<212> TYPE: PRT
<213> ORGANISM: Artificial
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: Ac modified
<220> FEATURE:
<221> NAME/KEY: MOD_RES
<222> LOCATION: (1)..(7)
<223> OTHER INFORMATION: Lactam bridge
<220> FEATURE:
<221> NAME/KEY: MOD_RES
<222> LOCATION: (4)..(4)
<223> OTHER INFORMATION: d isomer
<220> FEATURE:
<221> NAME/KEY: MISC_FEATURE
<222> LOCATION: (5)..(5)
<223> OTHER INFORMATION: Xaa = 2Nal
<220> FEATURE:
<221> NAME/KEY: MOD_RES
<222> LOCATION: (8)..(8)
<223> OTHER INFORMATION: AMIDATION

<400> SEQUENCE: 16

Glu Tyr Arg Arg Xaa Gly Lys Arg
1 5

<210> SEQ ID NO 17
<211> LENGTH: 8
<212> TYPE: PRT
<213> ORGANISM: Artificial
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: Ac modified
<220> FEATURE:
<221> NAME/KEY: MOD_RES
<222> LOCATION: (1)..(7)
<223> OTHER INFORMATION: Lactam bridge
<220> FEATURE:
<221> NAME/KEY: MOD_RES
<222> LOCATION: (4)..(4)
<223> OTHER INFORMATION: d isomer
<220> FEATURE:
<221> NAME/KEY: MISC_FEATURE
<222> LOCATION: (5)..(5)
<223> OTHER INFORMATION: Xaa = 2Nal
<220> FEATURE:
<221> NAME/KEY: MISC_FEATURE
<222> LOCATION: (7)..(7)
<223> OTHER INFORMATION: Xaa = Dab
<220> FEATURE:
<221> NAME/KEY: MOD_RES
<222> LOCATION: (8)..(8)
<223> OTHER INFORMATION: AMIDATION

<400> SEQUENCE: 17

Glu Tyr Arg Arg Xaa Gly Xaa Arg
1 5

<210> SEQ ID NO 18
<211> LENGTH: 8
<212> TYPE: PRT
<213> ORGANISM: Artificial
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: Ac modified
<220> FEATURE:
<221> NAME/KEY: MOD_RES
<222> LOCATION: (1)..(7)
<223> OTHER INFORMATION: Lactam bridge
<220> FEATURE:
<221> NAME/KEY: MOD_RES
<222> LOCATION: (4)..(4)
<223> OTHER INFORMATION: d isomer
<220> FEATURE:
<221> NAME/KEY: MISC_FEATURE
<222> LOCATION: (5)..(5)
<223> OTHER INFORMATION: Xaa = 2Nal
<220> FEATURE:
<221> NAME/KEY: MISC_FEATURE
<222> LOCATION: (7)..(7)
<223> OTHER INFORMATION: Xaa = d or l isomer Agl
<220> FEATURE:
<221> NAME/KEY: MOD_RES
<222> LOCATION: (8)..(8)
<223> OTHER INFORMATION: AMIDATION

<400> SEQUENCE: 18

Glu Tyr Arg Arg Xaa Gly Xaa Arg
1 5

<210> SEQ ID NO 19
<211> LENGTH: 8
<212> TYPE: PRT
<213> ORGANISM: Artificial
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: Bz modified
<220> FEATURE:
<221> NAME/KEY: MOD_RES
<222> LOCATION: (1)..(7)
<223> OTHER INFORMATION: Lactam bridge
<220> FEATURE:
<221> NAME/KEY: MOD_RES
<222> LOCATION: (4)..(4)
<223> OTHER INFORMATION: d isomer
<220> FEATURE:
<221> NAME/KEY: MISC_FEATURE
<222> LOCATION: (5)..(5)
<223> OTHER INFORMATION: Xaa = 2Nal
<220> FEATURE:
<221> NAME/KEY: MISC_FEATURE
<222> LOCATION: (7)..(7)
<223> OTHER INFORMATION: Xaa = d or l isomer Agl
<220> FEATURE:
<221> NAME/KEY: MOD_RES
<222> LOCATION: (8)..(8)
<223> OTHER INFORMATION: AMIDATION

<400> SEQUENCE: 19

Glu Tyr Arg Arg Xaa Gly Xaa Arg
1 5

<210> SEQ ID NO 20
<211> LENGTH: 8
<212> TYPE: PRT
<213> ORGANISM: Artificial
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: Bz modified
<220> FEATURE:
<221> NAME/KEY: MOD_RES
<222> LOCATION: (1)..(7)
<223> OTHER INFORMATION: Lactam bridge
<220> FEATURE:
<221> NAME/KEY: MOD_RES
<222> LOCATION: (4)..(4)
<223> OTHER INFORMATION: d isomer
<220> FEATURE:
<221> NAME/KEY: MISC_FEATURE
<222> LOCATION: (5)..(5)
<223> OTHER INFORMATION: Xaa = 2Nal
<220> FEATURE:
<221> NAME/KEY: MISC_FEATURE
<222> LOCATION: (7)..(7)
<223> OTHER INFORMATION: Xaa = Dab
<220> FEATURE:
<221> NAME/KEY: MOD_RES
<222> LOCATION: (8)..(8)
<223> OTHER INFORMATION: AMIDATION

<400> SEQUENCE: 20

Asp Tyr Arg Arg Xaa Gly Xaa Arg
1 5

<210> SEQ ID NO 21
<211> LENGTH: 8
<212> TYPE: PRT
<213> ORGANISM: Artificial
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: Ac modified
<220> FEATURE:
<221> NAME/KEY: MOD_RES
<222> LOCATION: (1)..(7)
<223> OTHER INFORMATION: Lactam bridge
<220> FEATURE:
<221> NAME/KEY: MOD_RES
<222> LOCATION: (4)..(4)
<223> OTHER INFORMATION: d isomer
<220> FEATURE:
<221> NAME/KEY: MISC_FEATURE
<222> LOCATION: (5)..(5)
<223> OTHER INFORMATION: Xaa = 2Nal
<220> FEATURE:
<221> NAME/KEY: MISC_FEATURE
<222> LOCATION: (7)..(7)
<223> OTHER INFORMATION: Xaa = Dab
<220> FEATURE:
<221> NAME/KEY: MOD_RES
<222> LOCATION: (8)..(8)
<223> OTHER INFORMATION: AMIDATION

<400> SEQUENCE: 21

Asp Tyr Arg Arg Xaa Gly Xaa Arg
1 5

<210> SEQ ID NO 22
<211> LENGTH: 8
<212> TYPE: PRT
<213> ORGANISM: Artificial
<220> FEATURE:

<223> OTHER INFORMATION: Synthetic construct
<220> FEATURE:
<221> NAME/KEY: MOD_RES
<222> LOCATION: (1)..(1)
<223> OTHER INFORMATION: Ac modified
<220> FEATURE:
<221> NAME/KEY: MOD_RES
<222> LOCATION: (1)..(7)
<223> OTHER INFORMATION: Lactam bridge
<220> FEATURE:
<221> NAME/KEY: MOD_RES
<222> LOCATION: (4)..(4)
<223> OTHER INFORMATION: d isomer
<220> FEATURE:
<221> NAME/KEY: MISC_FEATURE
<222> LOCATION: (5)..(5)
<223> OTHER INFORMATION: Xaa = 2Nal
<220> FEATURE:
<221> NAME/KEY: MISC_FEATURE
<222> LOCATION: (7)..(7)
<223> OTHER INFORMATION: Xaa = Dap
<220> FEATURE:
<221> NAME/KEY: MOD_RES
<222> LOCATION: (8)..(8)
<223> OTHER INFORMATION: AMIDATION

<400> SEQUENCE: 22

Asp Tyr Arg Arg Xaa Gly Xaa Arg
1 5

<210> SEQ ID NO 23
<211> LENGTH: 8
<212> TYPE: PRT
<213> ORGANISM: Artificial
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: Bz modified
<220> FEATURE:
<221> NAME/KEY: MOD_RES
<222> LOCATION: (1)..(7)
<223> OTHER INFORMATION: Lactam bridge
<220> FEATURE:
<221> NAME/KEY: MOD_RES
<222> LOCATION: (4)..(4)
<223> OTHER INFORMATION: d isomer
<220> FEATURE:
<221> NAME/KEY: MISC_FEATURE
<222> LOCATION: (5)..(5)
<223> OTHER INFORMATION: Xaa = 2Nal
<220> FEATURE:
<221> NAME/KEY: MISC_FEATURE
<222> LOCATION: (7)..(7)
<223> OTHER INFORMATION: Xaa = Dap
<220> FEATURE:
<221> NAME/KEY: MOD_RES
<222> LOCATION: (8)..(8)
<223> OTHER INFORMATION: AMIDATION

<400> SEQUENCE: 23

Asp Tyr Arg Arg Xaa Gly Xaa Arg
1 5

<210> SEQ ID NO 24
<211> LENGTH: 8
<212> TYPE: PRT
<213> ORGANISM: Artificial
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: Ac modified
<220> FEATURE:

<221> NAME/KEY: MOD_RES
<222> LOCATION: (1)..(7)
<223> OTHER INFORMATION: Lactam bridge
<220> FEATURE:
<221> NAME/KEY: MOD_RES
<222> LOCATION: (4)..(4)
<223> OTHER INFORMATION: d isomer
<220> FEATURE:
<221> NAME/KEY: MISC_FEATURE
<222> LOCATION: (5)..(5)
<223> OTHER INFORMATION: Xaa = 2Nal
<220> FEATURE:
<221> NAME/KEY: MISC_FEATURE
<222> LOCATION: (7)..(7)
<223> OTHER INFORMATION: Xaa = d or l isomer Agl
<220> FEATURE:
<221> NAME/KEY: MOD_RES
<222> LOCATION: (8)..(8)
<223> OTHER INFORMATION: AMIDATION

<400> SEQUENCE: 24

Asp Tyr Arg Arg Xaa Gly Xaa Arg
1 5

<210> SEQ ID NO 25
<211> LENGTH: 8
<212> TYPE: PRT
<213> ORGANISM: Artificial
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: Ac modified
<220> FEATURE:
<221> NAME/KEY: MOD_RES
<222> LOCATION: (1)..(7)
<223> OTHER INFORMATION: Lactam bridge
<220> FEATURE:
<221> NAME/KEY: MISC_FEATURE
<222> LOCATION: (3)..(3)
<223> OTHER INFORMATION: Xaa = Lys(Me2)
<220> FEATURE:
<221> NAME/KEY: MOD_RES
<222> LOCATION: (4)..(4)
<223> OTHER INFORMATION: d isomer
<220> FEATURE:
<221> NAME/KEY: MISC_FEATURE
<222> LOCATION: (5)..(5)
<223> OTHER INFORMATION: Xaa = 2Nal
<220> FEATURE:
<221> NAME/KEY: MISC_FEATURE
<222> LOCATION: (7)..(7)
<223> OTHER INFORMATION: Xaa = Dap
<220> FEATURE:
<221> NAME/KEY: MOD_RES
<222> LOCATION: (8)..(8)
<223> OTHER INFORMATION: AMIDATION

<400> SEQUENCE: 25

Asp Tyr Xaa Arg Xaa Gly Xaa Arg
1 5

<210> SEQ ID NO 26
<211> LENGTH: 8
<212> TYPE: PRT
<213> ORGANISM: Artificial
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: Bz modified
<220> FEATURE:
<221> NAME/KEY: MOD_RES
<222> LOCATION: (1)..(7)

<223> OTHER INFORMATION: Lactam bridge
<220> FEATURE:
<221> NAME/KEY: MISC_FEATURE
<222> LOCATION: (3)..(3)
<223> OTHER INFORMATION: Xaa = Lys(Me2)
<220> FEATURE:
<221> NAME/KEY: MOD_RES
<222> LOCATION: (4)..(4)
<223> OTHER INFORMATION: d isomer
<220> FEATURE:
<221> NAME/KEY: MISC_FEATURE
<222> LOCATION: (5)..(5)
<223> OTHER INFORMATION: Xaa = 2Nal
<220> FEATURE:
<221> NAME/KEY: MISC_FEATURE
<222> LOCATION: (7)..(7)
<223> OTHER INFORMATION: Xaa = Dap
<220> FEATURE:
<221> NAME/KEY: MOD_RES
<222> LOCATION: (8)..(8)
<223> OTHER INFORMATION: AMIDATION

<400> SEQUENCE: 26

Asp Tyr Xaa Arg Xaa Gly Xaa Arg
1 5

<210> SEQ ID NO 27
<211> LENGTH: 7
<212> TYPE: PRT
<213> ORGANISM: Artificial
<220> FEATURE:
<223> OTHER INFORMATION: Synthetic construct
<220> FEATURE:
<221> NAME/KEY: MOD_RES
<222> LOCATION: (1)..(6)
<223> OTHER INFORMATION: Lactam bridge
<220> FEATURE:
<221> NAME/KEY: MOD_RES
<222> LOCATION: (1)..(1)
<223> OTHER INFORMATION: Succinyl modified
<220> FEATURE:
<221> NAME/KEY: MOD_RES
<222> LOCATION: (3)..(3)
<223> OTHER INFORMATION: d isomer
<220> FEATURE:
<221> NAME/KEY: MISC_FEATURE
<222> LOCATION: (4)..(4)
<223> OTHER INFORMATION: Xaa = 2Nal
<220> FEATURE:
<221> NAME/KEY: MISC_FEATURE
<222> LOCATION: (6)..(6)
<223> OTHER INFORMATION: Xaa = d or l isomer Agl
<220> FEATURE:
<221> NAME/KEY: MOD_RES
<222> LOCATION: (7)..(7)
<223> OTHER INFORMATION: AMIDATION

<400> SEQUENCE: 27

Tyr Arg Arg Xaa Gly Xaa Arg
1 5

<210> SEQ ID NO 28
<211> LENGTH: 7
<212> TYPE: PRT
<213> ORGANISM: Artificial
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: Succinyl modified
<220> FEATURE:
<221> NAME/KEY: MOD_RES
<222> LOCATION: (1)..(6)
<223> OTHER INFORMATION: Lactam bridge
<220> FEATURE:

<221> NAME/KEY: MOD_RES
<222> LOCATION: (3)..(3)
<223> OTHER INFORMATION: d isomer
<220> FEATURE:
<221> NAME/KEY: MISC_FEATURE
<222> LOCATION: (4)..(4)
<223> OTHER INFORMATION: Xaa = 2Nal
<220> FEATURE:
<221> NAME/KEY: MISC_FEATURE
<222> LOCATION: (6)..(6)
<223> OTHER INFORMATION: Xaa = Dap
<220> FEATURE:
<221> NAME/KEY: MOD_RES
<222> LOCATION: (7)..(7)
<223> OTHER INFORMATION: AMIDATION

<400> SEQUENCE: 28

Tyr Arg Arg Xaa Gly Xaa Arg
1 5

<210> SEQ ID NO 29
<211> LENGTH: 7
<212> TYPE: PRT
<213> ORGANISM: Artificial
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: Succinyl modified
<220> FEATURE:
<221> NAME/KEY: MOD_RES
<222> LOCATION: (1)..(6)
<223> OTHER INFORMATION: Lactam bridge
<220> FEATURE:
<221> NAME/KEY: MOD_RES
<222> LOCATION: (3)..(3)
<223> OTHER INFORMATION: d isomer
<220> FEATURE:
<221> NAME/KEY: MISC_FEATURE
<222> LOCATION: (4)..(4)
<223> OTHER INFORMATION: Xaa = 2Nal
<220> FEATURE:
<221> NAME/KEY: MISC_FEATURE
<222> LOCATION: (6)..(6)
<223> OTHER INFORMATION: Xaa = Dab
<220> FEATURE:
<221> NAME/KEY: MOD_RES
<222> LOCATION: (7)..(7)
<223> OTHER INFORMATION: AMIDATION

<400> SEQUENCE: 29

Tyr Arg Arg Xaa Gly Xaa Arg
1 5

<210> SEQ ID NO 30
<211> LENGTH: 7
<212> TYPE: PRT
<213> ORGANISM: Artificial
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: Succinyl modified
<220> FEATURE:
<221> NAME/KEY: MOD_RES
<222> LOCATION: (1)..(6)
<223> OTHER INFORMATION: Lactam bridge
<220> FEATURE:
<221> NAME/KEY: MOD_RES
<222> LOCATION: (3)..(3)
<223> OTHER INFORMATION: d isomer
<220> FEATURE:
<221> NAME/KEY: MISC_FEATURE
<222> LOCATION: (4)..(4)

<223> OTHER INFORMATION: Xaa = 2Nal
<220> FEATURE:
<221> NAME/KEY: MISC_FEATURE
<222> LOCATION: (6)..(6)
<223> OTHER INFORMATION: Xaa = Orn
<220> FEATURE:
<221> NAME/KEY: MOD_RES
<222> LOCATION: (7)..(7)
<223> OTHER INFORMATION: AMIDATION

<400> SEQUENCE: 30

Tyr Arg Arg Xaa Gly Xaa Arg
1 5

<210> SEQ ID NO 31
<211> LENGTH: 7
<212> TYPE: PRT
<213> ORGANISM: Artificial
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: Succinyl modified
<220> FEATURE:
<221> NAME/KEY: MOD_RES
<222> LOCATION: (1)..(6)
<223> OTHER INFORMATION: Lactam bridge
<220> FEATURE:
<221> NAME/KEY: MOD_RES
<222> LOCATION: (3)..(3)
<223> OTHER INFORMATION: d isomer
<220> FEATURE:
<221> NAME/KEY: MISC_FEATURE
<222> LOCATION: (4)..(4)
<223> OTHER INFORMATION: Xaa = 2Nal
<220> FEATURE:
<221> NAME/KEY: MOD_RES
<222> LOCATION: (7)..(7)
<223> OTHER INFORMATION: AMIDATION

<400> SEQUENCE: 31

Tyr Arg Arg Xaa Gly Lys Arg
1 5

<210> SEQ ID NO 32
<211> LENGTH: 8
<212> TYPE: PRT
<213> ORGANISM: Artificial
<220> FEATURE:
<223> OTHER INFORMATION: Synthetic construct
<220> FEATURE:
<221> NAME/KEY: MOD_RES
<222> LOCATION: (1)..(7)
<223> OTHER INFORMATION: Lactam bridge
<220> FEATURE:
<221> NAME/KEY: MISC_FEATURE
<222> LOCATION: (3)..(3)
<223> OTHER INFORMATION: Xaa = Lys(iPr)
<220> FEATURE:
<221> NAME/KEY: MOD_RES
<222> LOCATION: (4)..(4)
<223> OTHER INFORMATION: d isomer
<220> FEATURE:
<221> NAME/KEY: MISC_FEATURE
<222> LOCATION: (5)..(5)
<223> OTHER INFORMATION: Xaa = 2Nal
<220> FEATURE:
<221> NAME/KEY: MOD_RES
<222> LOCATION: (7)..(7)
<223> OTHER INFORMATION: d isomer
<220> FEATURE:
<221> NAME/KEY: MOD_RES
<222> LOCATION: (8)..(8)
<223> OTHER INFORMATION: AMIDATION

<400> SEQUENCE: 32

Gly Tyr Xaa Arg Xaa Gly Glu Arg
1 5

<210> SEQ ID NO 33
<211> LENGTH: 8
<212> TYPE: PRT
<213> ORGANISM: Artificial
<220> FEATURE:
<223> OTHER INFORMATION: Synthetic construct
<220> FEATURE:
<221> NAME/KEY: MISC_FEATURE
<222> LOCATION: (2)..(2)
<223> OTHER INFORMATION: Xaa = Tyr(tBu)
<220> FEATURE:
<221> NAME/KEY: MISC_FEATURE
<222> LOCATION: (3)..(3)
<223> OTHER INFORMATION: Xaa = Lys(iPr)(Boc)
<220> FEATURE:
<221> NAME/KEY: MISC_FEATURE
<222> LOCATION: (4)..(4)
<223> OTHER INFORMATION: Xaa = d isomer Arg(Pbf)
<220> FEATURE:
<221> NAME/KEY: MISC_FEATURE
<222> LOCATION: (5)..(5)
<223> OTHER INFORMATION: Xaa = 2Nal
<220> FEATURE:
<221> NAME/KEY: MISC_FEATURE
<222> LOCATION: (7)..(7)
<223> OTHER INFORMATION: Xaa = d isomer Glu(Oallyl)
<220> FEATURE:
<221> NAME/KEY: MISC_FEATURE
<222> LOCATION: (8)..(8)
<223> OTHER INFORMATION: Xaa = Arg(Pbf)

<400> SEQUENCE: 33

Gly Xaa Xaa Xaa Xaa Gly Xaa Xaa
1 5

<210> SEQ ID NO 34
<211> LENGTH: 8
<212> TYPE: PRT
<213> ORGANISM: Artificial
<220> FEATURE:
<223> OTHER INFORMATION: Synthetic construct
<220> FEATURE:
<221> NAME/KEY: MOD_RES
<222> LOCATION: (1)..(7)
<223> OTHER INFORMATION: Lactam bridge
<220> FEATURE:
<221> NAME/KEY: MISC_FEATURE
<222> LOCATION: (3)..(3)
<223> OTHER INFORMATION: Xaa = Lys(iPr)
<220> FEATURE:
<221> NAME/KEY: MOD_RES
<222> LOCATION: (4)..(4)
<223> OTHER INFORMATION: d isomer
<220> FEATURE:
<221> NAME/KEY: MISC_FEATURE
<222> LOCATION: (5)..(5)
<223> OTHER INFORMATION: Xaa = 2Nal
<220> FEATURE:
<221> NAME/KEY: MOD_RES
<222> LOCATION: (7)..(7)
<223> OTHER INFORMATION: d isomer
<220> FEATURE:
<221> NAME/KEY: MOD_RES
<222> LOCATION: (8)..(8)
<223> OTHER INFORMATION: AMIDATION
<220> FEATURE:
<221> NAME/KEY: MISC_FEATURE
<222> LOCATION: (8)..(8)
<223> OTHER INFORMATION: acetic acid salt

<400> SEQUENCE: 34

Gly Tyr Xaa Arg Xaa Gly Glu Arg
1 5

<210> SEQ ID NO 35
<211> LENGTH: 8
<212> TYPE: PRT
<213> ORGANISM: Artificial
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: Fmoc modified
<220> FEATURE:
<221> NAME/KEY: MISC_FEATURE
<222> LOCATION: (2)..(2)
<223> OTHER INFORMATION: Xaa = Tyr(tBu)
<220> FEATURE:
<221> NAME/KEY: MISC_FEATURE
<222> LOCATION: (3)..(3)
<223> OTHER INFORMATION: Xaa = Lys(iPr)(Boc)
<220> FEATURE:
<221> NAME/KEY: MISC_FEATURE
<222> LOCATION: (4)..(4)
<223> OTHER INFORMATION: Xaa = d isomer Arg(Pbf)
<220> FEATURE:
<221> NAME/KEY: MISC_FEATURE
<222> LOCATION: (5)..(5)
<223> OTHER INFORMATION: Xaa = 2Nal
<220> FEATURE:
<221> NAME/KEY: MISC_FEATURE
<222> LOCATION: (7)..(7)
<223> OTHER INFORMATION: Xaa = d isomer Glu(Oallyl)
<220> FEATURE:
<221> NAME/KEY: MISC_FEATURE
<222> LOCATION: (8)..(8)
<223> OTHER INFORMATION: Xaa = Arg(Pbf)
<220> FEATURE:
<221> NAME/KEY: MOD_RES
<222> LOCATION: (8)..(8)
<223> OTHER INFORMATION: AMIDATION

<400> SEQUENCE: 35

Gly Xaa Xaa Xaa Xaa Gly Xaa Xaa
1 5

<210> SEQ ID NO 36
<211> LENGTH: 8
<212> TYPE: PRT
<213> ORGANISM: Artificial
<220> FEATURE:
<223> OTHER INFORMATION: Synthetic construct
<220> FEATURE:
<221> NAME/KEY: MOD_RES
<222> LOCATION: (1)..(7)
<223> OTHER INFORMATION: Lactam bridge
<220> FEATURE:
<221> NAME/KEY: MISC_FEATURE
<222> LOCATION: (2)..(2)
<223> OTHER INFORMATION: Xaa = Tyr(tBu)
<220> FEATURE:
<221> NAME/KEY: MISC_FEATURE
<222> LOCATION: (3)..(3)
<223> OTHER INFORMATION: Xaa = Lys(iPr)(Boc)
<220> FEATURE:
<221> NAME/KEY: MISC_FEATURE
<222> LOCATION: (4)..(4)
<223> OTHER INFORMATION: Xaa = d isomer Arg(Pbf)
<220> FEATURE:
<221> NAME/KEY: MISC_FEATURE
<222> LOCATION: (5)..(5)
<223> OTHER INFORMATION: Xaa = 2Nal
<220> FEATURE:
<221> NAME/KEY: MOD_RES
<222> LOCATION: (7)..(7)
<223> OTHER INFORMATION: d isomer
<220> FEATURE:

<221> NAME/KEY: MISC_FEATURE
<222> LOCATION: (8)..(8)
<223> OTHER INFORMATION: Xaa = Arg(Pbf)
<220> FEATURE:
<221> NAME/KEY: MOD_RES
<222> LOCATION: (8)..(8)
<223> OTHER INFORMATION: AMIDATION

<400> SEQUENCE: 36

Gly Xaa Xaa Xaa Xaa Gly Glu Xaa
1 5

<210> SEQ ID NO 37
<211> LENGTH: 7
<212> TYPE: PRT
<213> ORGANISM: Artificial
<220> FEATURE:
<223> OTHER INFORMATION: Synthetic construct
<220> FEATURE:
<221> NAME/KEY: MOD_RES
<222> LOCATION: (1)..(7)
<223> OTHER INFORMATION: Lactam bridge
<220> FEATURE:
<221> NAME/KEY: MISC_FEATURE
<222> LOCATION: (3)..(3)
<223> OTHER INFORMATION: Xaa = Lys(iPr)
<220> FEATURE:
<221> NAME/KEY: MOD_RES
<222> LOCATION: (4)..(4)
<223> OTHER INFORMATION: d isomer
<220> FEATURE:
<221> NAME/KEY: MISC_FEATURE
<222> LOCATION: (5)..(5)
<223> OTHER INFORMATION: Xaa = 2Nal
<220> FEATURE:
<221> NAME/KEY: MOD_RES
<222> LOCATION: (7)..(7)
<223> OTHER INFORMATION: d isomer
<220> FEATURE:
<221> NAME/KEY: MOD_RES
<222> LOCATION: (7)..(7)
<223> OTHER INFORMATION: AMIDATION

<400> SEQUENCE: 37

Gly Tyr Xaa Arg Xaa Gly Glu
1 5

<210> SEQ ID NO 38
<211> LENGTH: 7
<212> TYPE: PRT
<213> ORGANISM: Artificial
<220> FEATURE:
<223> OTHER INFORMATION: Synthetic construct
<220> FEATURE:
<221> NAME/KEY: MOD_RES
<222> LOCATION: (1)..(7)
<223> OTHER INFORMATION: Lactam bridge
<220> FEATURE:
<221> NAME/KEY: MISC_FEATURE
<222> LOCATION: (3)..(3)
<223> OTHER INFORMATION: Xaa = Lys(iPr)
<220> FEATURE:
<221> NAME/KEY: MOD_RES
<222> LOCATION: (4)..(4)
<223> OTHER INFORMATION: d isomer
<220> FEATURE:
<221> NAME/KEY: MISC_FEATURE
<222> LOCATION: (5)..(5)
<223> OTHER INFORMATION: Xaa = 2Nal
<220> FEATURE:
<221> NAME/KEY: MOD_RES
<222> LOCATION: (7)..(7)
<223> OTHER INFORMATION: d isomer
<220> FEATURE:
<221> NAME/KEY: MOD_RES
<222> LOCATION: (7)..(7)

<223> OTHER INFORMATION: AMIDATION
<220> FEATURE:
<221> NAME/KEY: MISC_FEATURE
<222> LOCATION: (7)..(7)
<223> OTHER INFORMATION: acetic acid salt

<400> SEQUENCE: 38

Gly Tyr Xaa Arg Xaa Gly Glu
1 5

<210> SEQ ID NO 39
<211> LENGTH: 8
<212> TYPE: PRT
<213> ORGANISM: Artificial
<220> FEATURE:
<223> OTHER INFORMATION: Synthetic construct
<220> FEATURE:
<221> NAME/KEY: MOD_RES
<222> LOCATION: (1)..(7)
<223> OTHER INFORMATION: Lactam bridge
<220> FEATURE:
<221> NAME/KEY: MOD_RES
<222> LOCATION: (4)..(4)
<223> OTHER INFORMATION: d isomer
<220> FEATURE:
<221> NAME/KEY: MISC_FEATURE
<222> LOCATION: (5)..(5)
<223> OTHER INFORMATION: Xaa = 2Nal
<220> FEATURE:
<221> NAME/KEY: MOD_RES
<222> LOCATION: (7)..(7)
<223> OTHER INFORMATION: d isomer
<220> FEATURE:
<221> NAME/KEY: MOD_RES
<222> LOCATION: (8)..(8)
<223> OTHER INFORMATION: AMIDATION

<400> SEQUENCE: 39

Gly Tyr Arg Arg Xaa Gly Glu Arg
1 5

<210> SEQ ID NO 40
<211> LENGTH: 8
<212> TYPE: PRT
<213> ORGANISM: Artificial
<220> FEATURE:
<223> OTHER INFORMATION: Synthetic construct
<220> FEATURE:
<221> NAME/KEY: MOD_RES
<222> LOCATION: (1)..(7)
<223> OTHER INFORMATION: Lactam bridge
<220> FEATURE:
<221> NAME/KEY: MISC_FEATURE
<222> LOCATION: (3)..(3)
<223> OTHER INFORMATION: Xaa = Lys(iPr)
<220> FEATURE:
<221> NAME/KEY: MOD_RES
<222> LOCATION: (4)..(4)
<223> OTHER INFORMATION: d isomer
<220> FEATURE:
<221> NAME/KEY: MISC_FEATURE
<222> LOCATION: (5)..(5)
<223> OTHER INFORMATION: Xaa = 2Nal
<220> FEATURE:
<221> NAME/KEY: MOD_RES
<222> LOCATION: (7)..(7)
<223> OTHER INFORMATION: d isomer
<220> FEATURE:
<221> NAME/KEY: MISC_FEATURE
<222> LOCATION: (8)..(8)
<223> OTHER INFORMATION: Xaa = Lys(iPr)
<220> FEATURE:
<221> NAME/KEY: MOD_RES
<222> LOCATION: (8)..(8)
<223> OTHER INFORMATION: AMIDATION

<400> SEQUENCE: 40

Gly Tyr Xaa Arg Xaa Gly Glu Xaa
1 5

<210> SEQ ID NO 41
<211> LENGTH: 7
<212> TYPE: PRT
<213> ORGANISM: Artificial
<220> FEATURE:
<223> OTHER INFORMATION: Synthetic construct
<220> FEATURE:
<221> NAME/KEY: MOD_RES
<222> LOCATION: (1)..(6)
<223> OTHER INFORMATION: Lactam bridge
<220> FEATURE:
<221> NAME/KEY: MOD_RES
<222> LOCATION: (3)..(3)
<223> OTHER INFORMATION: d isomer
<220> FEATURE:
<221> NAME/KEY: MISC_FEATURE
<222> LOCATION: (4)..(4)
<223> OTHER INFORMATION: Xaa = 2Nal
<220> FEATURE:
<221> NAME/KEY: MOD_RES
<222> LOCATION: (7)..(7)
<223> OTHER INFORMATION: AMIDATION

<400> SEQUENCE: 41

Tyr Arg Arg Xaa Gly Glu Arg
1 5

<210> SEQ ID NO 42
<211> LENGTH: 7
<212> TYPE: PRT
<213> ORGANISM: Artificial
<220> FEATURE:
<223> OTHER INFORMATION: Synthetic construct
<220> FEATURE:
<221> NAME/KEY: MOD_RES
<222> LOCATION: (1)..(6)
<223> OTHER INFORMATION: Lactam bridge
<220> FEATURE:
<221> NAME/KEY: MOD_RES
<222> LOCATION: (3)..(3)
<223> OTHER INFORMATION: d isomer
<220> FEATURE:
<221> NAME/KEY: MISC_FEATURE
<222> LOCATION: (4)..(4)
<223> OTHER INFORMATION: Xaa = 2Nal
<220> FEATURE:
<221> NAME/KEY: MOD_RES
<222> LOCATION: (6)..(6)
<223> OTHER INFORMATION: d isomer
<220> FEATURE:
<221> NAME/KEY: MOD_RES
<222> LOCATION: (7)..(7)
<223> OTHER INFORMATION: AMIDATION

<400> SEQUENCE: 42

Tyr Arg Arg Xaa Gly Glu Arg
1 5

<210> SEQ ID NO 43
<211> LENGTH: 7
<212> TYPE: PRT
<213> ORGANISM: Artificial
<220> FEATURE:
<223> OTHER INFORMATION: Synthetic construct
<220> FEATURE:
<221> NAME/KEY: MOD_RES
<222> LOCATION: (1)..(6)
<223> OTHER INFORMATION: Lactam bridge
<220> FEATURE:
<221> NAME/KEY: MOD_RES <222> LOCATION: (3)..(3)
<223> OTHER INFORMATION: d isomer
<220> FEATURE:
<221> NAME/KEY: MISC_FEATURE
<222> LOCATION: (4)..(4)
<223> OTHER INFORMATION: Xaa = 2Nal
<220> FEATURE:
<221> NAME/KEY: MOD_RES
<222> LOCATION: (7)..(7)
<223> OTHER INFORMATION: AMIDATION

<400> SEQUENCE: 43

Tyr Arg Arg Xaa Gly Asp Arg
1 5

<210> SEQ ID NO 44
<211> LENGTH: 8
<212> TYPE: PRT
<213> ORGANISM: Artificial
<220> FEATURE:
<223> OTHER INFORMATION: Synthetic construct
<220> FEATURE:
<221> NAME/KEY: MOD_RES
<222> LOCATION: (1)..(7)
<223> OTHER INFORMATION: Lactam bridge
<220> FEATURE:
<221> NAME/KEY: MOD_RES
<222> LOCATION: (4)..(4)
<223> OTHER INFORMATION: d isomer
<220> FEATURE:
<221> NAME/KEY: MISC_FEATURE
<222> LOCATION: (5)..(5)
<223> OTHER INFORMATION: Xaa = 2Nal
<220> FEATURE:
<221> NAME/KEY: MOD_RES
<222> LOCATION: (8)..(8)
<223> OTHER INFORMATION: AMIDATION

<400> SEQUENCE: 44

Gly Tyr Arg Arg Xaa Gly Asp Arg
1 5

<210> SEQ ID NO 45
<211> LENGTH: 8
<212> TYPE: PRT
<213> ORGANISM: Artificial
<220> FEATURE:
<223> OTHER INFORMATION: Synthetic construct
<220> FEATURE:
<221> NAME/KEY: MOD_RES
<222> LOCATION: (1)..(7)
<223> OTHER INFORMATION: Lactam bridge
<220> FEATURE:
<221> NAME/KEY: MISC_FEATURE
<222> LOCATION: (3)..(3)
<223> OTHER INFORMATION: Xaa = Lys(Me2)
<220> FEATURE:
<221> NAME/KEY: MOD_RES
<222> LOCATION: (4)..(4)
<223> OTHER INFORMATION: d isomer
<220> FEATURE:
<221> NAME/KEY: MISC_FEATURE
<222> LOCATION: (5)..(5)
<223> OTHER INFORMATION: Xaa = 2Nal
<220> FEATURE:
<221> NAME/KEY: MOD_RES
<222> LOCATION: (8)..(8)
<223> OTHER INFORMATION: AMIDATION

<400> SEQUENCE: 45

Gly Tyr Xaa Arg Xaa Gly Asp Arg
1 5

<210> SEQ ID NO 46

<211> LENGTH: 8
<212> TYPE: PRT
<213> ORGANISM: Artificial
<220> FEATURE:
<223> OTHER INFORMATION: Synthetic construct
<220> FEATURE:
<221> NAME/KEY: MOD_RES
<222> LOCATION: (1)..(7)
<223> OTHER INFORMATION: Lactam bridge
<220> FEATURE:
<221> NAME/KEY: MISC_FEATURE
<222> LOCATION: (3)..(3)
<223> OTHER INFORMATION: Xaa = Lys(iPr)
<220> FEATURE:
<221> NAME/KEY: MOD_RES
<222> LOCATION: (4)..(4)
<223> OTHER INFORMATION: d isomer
<220> FEATURE:
<221> NAME/KEY: MISC_FEATURE
<222> LOCATION: (5)..(5)
<223> OTHER INFORMATION: Xaa = 2Nal
<220> FEATURE:
<221> NAME/KEY: MOD_RES
<222> LOCATION: (8)..(8)
<223> OTHER INFORMATION: AMIDATION

<400> SEQUENCE: 46

Gly Tyr Xaa Arg Xaa Gly Asp Arg
1 5

<210> SEQ ID NO 47
<211> LENGTH: 7
<212> TYPE: PRT
<213> ORGANISM: Artificial
<220> FEATURE:
<223> OTHER INFORMATION: Synthetic construct
<220> FEATURE:
<221> NAME/KEY: MOD_RES
<222> LOCATION: (1)..(7)
<223> OTHER INFORMATION: Lactam bridge
<220> FEATURE:
<221> NAME/KEY: MISC_FEATURE
<222> LOCATION: (3)..(3)
<223> OTHER INFORMATION: Xaa = Lys(iPr)
<220> FEATURE:
<221> NAME/KEY: MOD_RES
<222> LOCATION: (4)..(4)
<223> OTHER INFORMATION: d isomer
<220> FEATURE:
<221> NAME/KEY: MISC_FEATURE
<222> LOCATION: (5)..(5)
<223> OTHER INFORMATION: Xaa = 2Nal
<220> FEATURE:
<221> NAME/KEY: MOD_RES
<222> LOCATION: (7)..(7)
<223> OTHER INFORMATION: AMIDATION

<400> SEQUENCE: 47

Gly Tyr Xaa Arg Xaa Gly Asp
1 5

<210> SEQ ID NO 48
<211> LENGTH: 8
<212> TYPE: PRT
<213> ORGANISM: Artificial
<220> FEATURE:
<223> OTHER INFORMATION: Synthetic construct
<220> FEATURE:
<221> NAME/KEY: MOD_RES
<222> LOCATION: (1)..(7)
<223> OTHER INFORMATION: Lactam bridge
<220> FEATURE:
<221> NAME/KEY: MISC_FEATURE
<222> LOCATION: (3)..(3)
<223> OTHER INFORMATION: Xaa = Lys(iPr)
<220> FEATURE:

<221> NAME/KEY: MOD_RES
<222> LOCATION: (4)..(4)
<223> OTHER INFORMATION: d isomer
<220> FEATURE:
<221> NAME/KEY: MISC_FEATURE
<222> LOCATION: (5)..(5)
<223> OTHER INFORMATION: Xaa = 2Nal
<220> FEATURE:
<221> NAME/KEY: MISC_FEATURE
<222> LOCATION: (8)..(8)
<223> OTHER INFORMATION: Xaa = Lys(iPr)
<220> FEATURE:
<221> NAME/KEY: MOD_RES
<222> LOCATION: (8)..(8)
<223> OTHER INFORMATION: AMIDATION

<400> SEQUENCE: 48

Gly Tyr Xaa Arg Xaa Gly Asp Xaa
1 5

<210> SEQ ID NO 49
<211> LENGTH: 8
<212> TYPE: PRT
<213> ORGANISM: Artificial
<220> FEATURE:
<223> OTHER INFORMATION: Synthetic construct
<220> FEATURE:
<221> NAME/KEY: MOD_RES
<222> LOCATION: (1)..(7)
<223> OTHER INFORMATION: Lactam bridge
<220> FEATURE:
<221> NAME/KEY: MISC_FEATURE
<222> LOCATION: (3)..(3)
<223> OTHER INFORMATION: Xaa = Lys(Me2)
<220> FEATURE:
<221> NAME/KEY: MOD_RES
<222> LOCATION: (4)..(4)
<223> OTHER INFORMATION: d isomer
<220> FEATURE:
<221> NAME/KEY: MISC_FEATURE
<222> LOCATION: (5)..(5)
<223> OTHER INFORMATION: Xaa = 2Nal
<220> FEATURE:
<221> NAME/KEY: MOD_RES
<222> LOCATION: (8)..(8)
<223> OTHER INFORMATION: AMIDATION

<400> SEQUENCE: 49

Gly Tyr Xaa Arg Xaa Gly Glu Arg
1 5

<210> SEQ ID NO 50
<211> LENGTH: 8
<212> TYPE: PRT
<213> ORGANISM: Artificial
<220> FEATURE:
<223> OTHER INFORMATION: Synthetic construct
<220> FEATURE:
<221> NAME/KEY: MOD_RES
<222> LOCATION: (1)..(7)
<223> OTHER INFORMATION: Lactam bridge
<220> FEATURE:
<221> NAME/KEY: MOD_RES
<222> LOCATION: (4)..(4)
<223> OTHER INFORMATION: d isomer
<220> FEATURE:
<221> NAME/KEY: MISC_FEATURE
<222> LOCATION: (5)..(5)
<223> OTHER INFORMATION: Xaa = 2Nal
<220> FEATURE:
<221> NAME/KEY: MOD_RES
<222> LOCATION: (8)..(8)
<223> OTHER INFORMATION: AMIDATION

<400> SEQUENCE: 50

Gly Tyr Arg Arg Xaa Gly Glu Arg
1 5

<210> SEQ ID NO 51
<211> LENGTH: 8
<212> TYPE: PRT
<213> ORGANISM: Artificial
<220> FEATURE:
<223> OTHER INFORMATION: Synthetic construct
<220> FEATURE:
<221> NAME/KEY: MOD_RES
<222> LOCATION: (1)..(7)
<223> OTHER INFORMATION: Lactam bridge
<220> FEATURE:
<221> NAME/KEY: MISC_FEATURE
<222> LOCATION: (3)..(3)
<223> OTHER INFORMATION: Xaa = Lys(iPr)
<220> FEATURE:
<221> NAME/KEY: MOD_RES
<222> LOCATION: (4)..(4)
<223> OTHER INFORMATION: d isomer
<220> FEATURE:
<221> NAME/KEY: MISC_FEATURE
<222> LOCATION: (5)..(5)
<223> OTHER INFORMATION: Xaa = 2Nal
<220> FEATURE:
<221> NAME/KEY: MOD_RES
<222> LOCATION: (8)..(8)
<223> OTHER INFORMATION: AMIDATION

<400> SEQUENCE: 51

Gly Tyr Xaa Arg Xaa Gly Glu Arg
1 5

<210> SEQ ID NO 52
<211> LENGTH: 7
<212> TYPE: PRT
<213> ORGANISM: Artificial
<220> FEATURE:
<223> OTHER INFORMATION: Synthetic construct
<220> FEATURE:
<221> NAME/KEY: MOD_RES
<222> LOCATION: (1)..(7)
<223> OTHER INFORMATION: Lactam bridge
<220> FEATURE:
<221> NAME/KEY: MISC_FEATURE
<222> LOCATION: (3)..(3)
<223> OTHER INFORMATION: Xaa = Lys(iPr)
<220> FEATURE:
<221> NAME/KEY: MOD_RES
<222> LOCATION: (4)..(4)
<223> OTHER INFORMATION: d isomer
<220> FEATURE:
<221> NAME/KEY: MISC_FEATURE
<222> LOCATION: (5)..(5)
<223> OTHER INFORMATION: Xaa = 2Nal
<220> FEATURE:
<221> NAME/KEY: MOD_RES
<222> LOCATION: (7)..(7)
<223> OTHER INFORMATION: AMIDATION

<400> SEQUENCE: 52

Gly Tyr Xaa Arg Xaa Gly Glu
1 5

<210> SEQ ID NO 53
<211> LENGTH: 7
<212> TYPE: PRT
<213> ORGANISM: Artificial
<220> FEATURE:
<223> OTHER INFORMATION: Synthetic construct
<220> FEATURE:
<221> NAME/KEY: MOD_RES
<222> LOCATION: (1)..(7)
<223> OTHER INFORMATION: Lactam bridge <220> FEATURE:
<221> NAME/KEY: MISC_FEATURE
<222> LOCATION: (3)..(3)
<223> OTHER INFORMATION: Xaa = Lys(iPr)
<220> FEATURE:
<221> NAME/KEY: MOD_RES
<222> LOCATION: (4)..(4)
<223> OTHER INFORMATION: d isomer
<220> FEATURE:
<221> NAME/KEY: MISC_FEATURE
<222> LOCATION: (5)..(5)
<223> OTHER INFORMATION: Xaa = 2Nal
<220> FEATURE:
<221> NAME/KEY: MOD_RES
<222> LOCATION: (7)..(7)
<223> OTHER INFORMATION: Amidated as NHEt

<400> SEQUENCE: 53

Gly Tyr Xaa Arg Xaa Gly Asp
1 5

<210> SEQ ID NO 54
<211> LENGTH: 7
<212> TYPE: PRT
<213> ORGANISM: Artificial
<220> FEATURE:
<223> OTHER INFORMATION: Synthetic construct
<220> FEATURE:
<221> NAME/KEY: MOD_RES
<222> LOCATION: (1)..(7)
<223> OTHER INFORMATION: Lactam bridge
<220> FEATURE:
<221> NAME/KEY: MISC_FEATURE
<222> LOCATION: (3)..(3)
<223> OTHER INFORMATION: Xaa = Lys(iPr)
<220> FEATURE:
<221> NAME/KEY: MOD_RES
<222> LOCATION: (4)..(4)
<223> OTHER INFORMATION: d isomer
<220> FEATURE:
<221> NAME/KEY: MISC_FEATURE
<222> LOCATION: (5)..(5)
<223> OTHER INFORMATION: Xaa = 2Nal
<220> FEATURE:
<221> NAME/KEY: MOD_RES
<222> LOCATION: (7)..(7)
<223> OTHER INFORMATION: Amidated as NHEt

<400> SEQUENCE: 54

Gly Tyr Xaa Arg Xaa Gly Glu
1 5

<210> SEQ ID NO 55
<211> LENGTH: 7
<212> TYPE: PRT
<213> ORGANISM: Artificial
<220> FEATURE:
<223> OTHER INFORMATION: Synthetic construct
<220> FEATURE:
<221> NAME/KEY: MOD_RES
<222> LOCATION: (1)..(7)
<223> OTHER INFORMATION: Lactam bridge
<220> FEATURE:
<221> NAME/KEY: MISC_FEATURE
<222> LOCATION: (3)..(3)
<223> OTHER INFORMATION: Xaa = Lys(iPr)
<220> FEATURE:
<221> NAME/KEY: MOD_RES
<222> LOCATION: (4)..(4)
<223> OTHER INFORMATION: d isomer
<220> FEATURE:
<221> NAME/KEY: MISC_FEATURE
<222> LOCATION: (5)..(5)
<223> OTHER INFORMATION: Xaa = 2Nal
<220> FEATURE:
<221> NAME/KEY: MOD_RES <222> LOCATION: (7)..(7)
<223> OTHER INFORMATION: d isomer
<220> FEATURE:
<221> NAME/KEY: MOD_RES
<222> LOCATION: (7)..(7)
<223> OTHER INFORMATION: Amidated as NHEt

<400> SEQUENCE: 55

Gly Tyr Xaa Arg Xaa Gly Glu
1 5

<210> SEQ ID NO 56
<211> LENGTH: 8
<212> TYPE: PRT
<213> ORGANISM: Artificial
<220> FEATURE:
<223> OTHER INFORMATION: Synthetic construct
<220> FEATURE:
<221> NAME/KEY: MOD_RES
<222> LOCATION: (1)..(7)
<223> OTHER INFORMATION: Lactam bridge
<220> FEATURE:
<221> NAME/KEY: MISC_FEATURE
<222> LOCATION: (3)..(3)
<223> OTHER INFORMATION: Xaa = Lys(iPr)
<220> FEATURE:
<221> NAME/KEY: MOD_RES
<222> LOCATION: (4)..(4)
<223> OTHER INFORMATION: d isomer
<220> FEATURE:
<221> NAME/KEY: MISC_FEATURE
<222> LOCATION: (5)..(5)
<223> OTHER INFORMATION: Xaa = 2Nal
<220> FEATURE:
<221> NAME/KEY: MOD_RES
<222> LOCATION: (7)..(7)
<223> OTHER INFORMATION: d isomer
<220> FEATURE:
<221> NAME/KEY: MOD_RES
<222> LOCATION: (8)..(8)
<223> OTHER INFORMATION: Amidated as NHEt

<400> SEQUENCE: 56

Gly Tyr Xaa Arg Xaa Gly Glu Arg
1 5

<210> SEQ ID NO 57
<211> LENGTH: 8
<212> TYPE: PRT
<213> ORGANISM: Artificial
<220> FEATURE:
<223> OTHER INFORMATION: Synthetic construct
<220> FEATURE:
<221> NAME/KEY: MOD_RES
<222> LOCATION: (1)..(7)
<223> OTHER INFORMATION: Lactam bridge
<220> FEATURE:
<221> NAME/KEY: MISC_FEATURE
<222> LOCATION: (3)..(3)
<223> OTHER INFORMATION: Xaa = Lys(iPr)
<220> FEATURE:
<221> NAME/KEY: MOD_RES
<222> LOCATION: (4)..(4)
<223> OTHER INFORMATION: d isomer
<220> FEATURE:
<221> NAME/KEY: MISC_FEATURE
<222> LOCATION: (5)..(5)
<223> OTHER INFORMATION: Xaa = 2Nal
<220> FEATURE:
<221> NAME/KEY: MOD_RES
<222> LOCATION: (7)..(7)
<223> OTHER INFORMATION: d isomer
<220> FEATURE:
<221> NAME/KEY: MOD_RES
<222> LOCATION: (8)..(8)
<223> OTHER INFORMATION: Amidated as NHEt <220> FEATURE:
<221> NAME/KEY: MISC_FEATURE
<222> LOCATION: (8)..(8)
<223> OTHER INFORMATION: acetic acid salt

<400> SEQUENCE: 57

Gly Tyr Xaa Arg Xaa Gly Glu Arg
1 5

<210> SEQ ID NO 58
<211> LENGTH: 8
<212> TYPE: PRT
<213> ORGANISM: Artificial
<220> FEATURE:
<223> OTHER INFORMATION: Synthetic construct
<220> FEATURE:
<221> NAME/KEY: MOD_RES
<222> LOCATION: (1)..(7)
<223> OTHER INFORMATION: Lactam bridge
<220> FEATURE:
<221> NAME/KEY: MISC_FEATURE
<222> LOCATION: (3)..(3)
<223> OTHER INFORMATION: Xaa = Lys(iPr)
<220> FEATURE:
<221> NAME/KEY: MOD_RES
<222> LOCATION: (4)..(4)
<223> OTHER INFORMATION: d isomer
<220> FEATURE:
<221> NAME/KEY: MISC_FEATURE
<222> LOCATION: (5)..(5)
<223> OTHER INFORMATION: Xaa = 2Nal
<220> FEATURE:
<221> NAME/KEY: MOD_RES
<222> LOCATION: (7)..(7)
<223> OTHER INFORMATION: d isomer
<220> FEATURE:
<221> NAME/KEY: MISC_FEATURE
<222> LOCATION: (8)..(8)
<223> OTHER INFORMATION: Xaa = Lys(iPr)
<220> FEATURE:
<221> NAME/KEY: MOD_RES
<222> LOCATION: (8)..(8)
<223> OTHER INFORMATION: Amidated as NHEt

<400> SEQUENCE: 58

Gly Tyr Xaa Arg Xaa Gly Glu Xaa
1 5

<210> SEQ ID NO 59
<211> LENGTH: 8
<212> TYPE: PRT
<213> ORGANISM: Artificial
<220> FEATURE:
<223> OTHER INFORMATION: Synthetic construct
<220> FEATURE:
<221> NAME/KEY: MOD_RES
<222> LOCATION: (1)..(7)
<223> OTHER INFORMATION: Lactam bridge
<220> FEATURE:
<221> NAME/KEY: MISC_FEATURE
<222> LOCATION: (1)..(1)
<223> OTHER INFORMATION: Xaa = Lys(Ac)
<220> FEATURE:
<221> NAME/KEY: MISC_FEATURE
<222> LOCATION: (3)..(3)
<223> OTHER INFORMATION: Xaa = Lys(Me2)
<220> FEATURE:
<221> NAME/KEY: MOD_RES
<222> LOCATION: (4)..(4)
<223> OTHER INFORMATION: d isomer
<220> FEATURE:
<221> NAME/KEY: MISC_FEATURE
<222> LOCATION: (5)..(5)
<223> OTHER INFORMATION: Xaa = 2Nal
<220> FEATURE:
<221> NAME/KEY: MOD_RES

<222> LOCATION: (8)..(8)
<223> OTHER INFORMATION: AMIDATION

<400> SEQUENCE: 59

Xaa Tyr Xaa Arg Xaa Gly Glu Arg
1 5

<210> SEQ ID NO 60
<211> LENGTH: 7
<212> TYPE: PRT
<213> ORGANISM: Artificial
<220> FEATURE:
<223> OTHER INFORMATION: Synthetic construct
<220> FEATURE:
<221> NAME/KEY: MOD_RES
<222> LOCATION: (1)..(7)
<223> OTHER INFORMATION: Lactam bridge
<220> FEATURE:
<221> NAME/KEY: MISC_FEATURE
<222> LOCATION: (1)..(1)
<223> OTHER INFORMATION: Xaa = Dap(Ac)
<220> FEATURE:
<221> NAME/KEY: MISC_FEATURE
<222> LOCATION: (3)..(3)
<223> OTHER INFORMATION: Xaa = Lys(Me2)
<220> FEATURE:
<221> NAME/KEY: MOD_RES
<222> LOCATION: (4)..(4)
<223> OTHER INFORMATION: d isomer
<220> FEATURE:
<221> NAME/KEY: MISC_FEATURE
<222> LOCATION: (5)..(5)
<223> OTHER INFORMATION: Xaa = 2Nal
<220> FEATURE:
<221> NAME/KEY: MOD_RES
<222> LOCATION: (7)..(7)
<223> OTHER INFORMATION: AMIDATION

<400> SEQUENCE: 60

Xaa Tyr Xaa Arg Xaa Gly Glu
1 5

<210> SEQ ID NO 61
<211> LENGTH: 7
<212> TYPE: PRT
<213> ORGANISM: Artificial
<220> FEATURE:
<223> OTHER INFORMATION: Synthetic construct
<220> FEATURE:
<221> NAME/KEY: MOD_RES
<222> LOCATION: (1)..(7)
<223> OTHER INFORMATION: Lactam bridge
<220> FEATURE:
<221> NAME/KEY: MISC_FEATURE
<222> LOCATION: (3)..(3)
<223> OTHER INFORMATION: Xaa = Lys(iPr)
<220> FEATURE:
<221> NAME/KEY: MOD_RES
<222> LOCATION: (4)..(4)
<223> OTHER INFORMATION: d isomer
<220> FEATURE:
<221> NAME/KEY: MISC_FEATURE
<222> LOCATION: (5)..(5)
<223> OTHER INFORMATION: Xaa = 2Nal
<220> FEATURE:
<221> NAME/KEY: MOD_RES
<222> LOCATION: (7)..(7)
<223> OTHER INFORMATION: AMIDATION

<400> SEQUENCE: 61

Ala Tyr Xaa Arg Xaa Gly Glu
1 5

<210> SEQ ID NO 62

<211> LENGTH: 7
<212> TYPE: PRT
<213> ORGANISM: Artificial
<220> FEATURE:
<223> OTHER INFORMATION: Synthetic construct
<220> FEATURE:
<221> NAME/KEY: MOD_RES
<222> LOCATION: (1)..(7)
<223> OTHER INFORMATION: Lactam bridge
<220> FEATURE:
<221> NAME/KEY: MOD_RES
<222> LOCATION: (1)..(1)
<223> OTHER INFORMATION: d isomer
<220> FEATURE:
<221> NAME/KEY: MISC_FEATURE
<222> LOCATION: (3)..(3)
<223> OTHER INFORMATION: Xaa = Lys(iPr)
<220> FEATURE:
<221> NAME/KEY: MOD_RES
<222> LOCATION: (4)..(4)
<223> OTHER INFORMATION: d isomer
<220> FEATURE:
<221> NAME/KEY: MISC_FEATURE
<222> LOCATION: (5)..(5)
<223> OTHER INFORMATION: Xaa = 2Nal
<220> FEATURE:
<221> NAME/KEY: MOD_RES
<222> LOCATION: (7)..(7)
<223> OTHER INFORMATION: AMIDATION

<400> SEQUENCE: 62

Ala Tyr Xaa Arg Xaa Gly Glu
1 5

<210> SEQ ID NO 63
<211> LENGTH: 7
<212> TYPE: PRT
<213> ORGANISM: Artificial
<220> FEATURE:
<223> OTHER INFORMATION: Synthetic construct
<220> FEATURE:
<221> NAME/KEY: MOD_RES
<222> LOCATION: (1)..(7)
<223> OTHER INFORMATION: Lactam bridge
<220> FEATURE:
<221> NAME/KEY: MOD_RES
<222> LOCATION: (1)..(1)
<223> OTHER INFORMATION: d isomer
<220> FEATURE:
<221> NAME/KEY: MISC_FEATURE
<222> LOCATION: (3)..(3)
<223> OTHER INFORMATION: Xaa = Lys(iPr)
<220> FEATURE:
<221> NAME/KEY: MOD_RES
<222> LOCATION: (4)..(4)
<223> OTHER INFORMATION: d isomer
<220> FEATURE:
<221> NAME/KEY: MISC_FEATURE
<222> LOCATION: (5)..(5)
<223> OTHER INFORMATION: Xaa = 2Nal
<220> FEATURE:
<221> NAME/KEY: MOD_RES
<222> LOCATION: (7)..(7)
<223> OTHER INFORMATION: d isomer
<220> FEATURE:
<221> NAME/KEY: MOD_RES
<222> LOCATION: (7)..(7)
<223> OTHER INFORMATION: AMIDATION

<400> SEQUENCE: 63

Ala Tyr Xaa Arg Xaa Gly Glu
1 5

<210> SEQ ID NO 64
<211> LENGTH: 7
<212> TYPE: PRT

<213> ORGANISM: Artificial
<220> FEATURE:
<223> OTHER INFORMATION: Synthetic construct
<220> FEATURE:
<221> NAME/KEY: MOD_RES
<222> LOCATION: (1)..(7)
<223> OTHER INFORMATION: Lactam bridge
<220> FEATURE:
<221> NAME/KEY: MISC_FEATURE
<222> LOCATION: (3)..(3)
<223> OTHER INFORMATION: Xaa = Lys(iPr)
<220> FEATURE:
<221> NAME/KEY: MOD_RES
<222> LOCATION: (4)..(4)
<223> OTHER INFORMATION: d isomer
<220> FEATURE:
<221> NAME/KEY: MISC_FEATURE
<222> LOCATION: (5)..(5)
<223> OTHER INFORMATION: Xaa = 2Nal
<220> FEATURE:
<221> NAME/KEY: MOD_RES
<222> LOCATION: (7)..(7)
<223> OTHER INFORMATION: d isomer
<220> FEATURE:
<221> NAME/KEY: MOD_RES
<222> LOCATION: (7)..(7)
<223> OTHER INFORMATION: AMIDATION

<400> SEQUENCE: 64

Ala Tyr Xaa Arg Xaa Gly Glu
1 5

<210> SEQ ID NO 65
<211> LENGTH: 7
<212> TYPE: PRT
<213> ORGANISM: Artificial
<220> FEATURE:
<223> OTHER INFORMATION: Synthetic construct
<220> FEATURE:
<221> NAME/KEY: MOD_RES
<222> LOCATION: (1)..(7)
<223> OTHER INFORMATION: Lactam bridge
<220> FEATURE:
<221> NAME/KEY: MISC_FEATURE
<222> LOCATION: (3)..(3)
<223> OTHER INFORMATION: Xaa = Lys(iPr)
<220> FEATURE:
<221> NAME/KEY: MOD_RES
<222> LOCATION: (4)..(4)
<223> OTHER INFORMATION: d isomer
<220> FEATURE:
<221> NAME/KEY: MISC_FEATURE
<222> LOCATION: (5)..(5)
<223> OTHER INFORMATION: Xaa = 2Nal
<220> FEATURE:
<221> NAME/KEY: MOD_RES
<222> LOCATION: (7)..(7)
<223> OTHER INFORMATION: d isomer
<220> FEATURE:
<221> NAME/KEY: MOD_RES
<222> LOCATION: (7)..(7)
<223> OTHER INFORMATION: AMIDATION

<400> SEQUENCE: 65

Leu Tyr Xaa Arg Xaa Gly Glu
1 5

<210> SEQ ID NO 66
<211> LENGTH: 7
<212> TYPE: PRT
<213> ORGANISM: Artificial
<220> FEATURE:
<223> OTHER INFORMATION: Synthetic construct
<220> FEATURE:
<221> NAME/KEY: MOD_RES
<222> LOCATION: (1)..(7)

<223> OTHER INFORMATION: Lactam bridge
<220> FEATURE:
<221> NAME/KEY: MISC_FEATURE
<222> LOCATION: (3)..(3)
<223> OTHER INFORMATION: Xaa = Lys(iPr)
<220> FEATURE:
<221> NAME/KEY: MOD_RES
<222> LOCATION: (4)..(4)
<223> OTHER INFORMATION: d isomer
<220> FEATURE:
<221> NAME/KEY: MISC_FEATURE
<222> LOCATION: (5)..(5)
<223> OTHER INFORMATION: Xaa = 2Nal
<220> FEATURE:
<221> NAME/KEY: MOD_RES
<222> LOCATION: (7)..(7)
<223> OTHER INFORMATION: AMIDATION

<400> SEQUENCE: 66

Leu Tyr Xaa Arg Xaa Gly Glu
1 5

<210> SEQ ID NO 67
<211> LENGTH: 7
<212> TYPE: PRT
<213> ORGANISM: Artificial
<220> FEATURE:
<223> OTHER INFORMATION: Synthetic construct
<220> FEATURE:
<221> NAME/KEY: MOD_RES
<222> LOCATION: (1)..(7)
<223> OTHER INFORMATION: lactam bridge
<220> FEATURE:
<221> NAME/KEY: MOD_RES
<222> LOCATION: (1)..(1)
<223> OTHER INFORMATION: d isomer
<220> FEATURE:
<221> NAME/KEY: MISC_FEATURE
<222> LOCATION: (3)..(3)
<223> OTHER INFORMATION: Xaa = Lys(iPr)
<220> FEATURE:
<221> NAME/KEY: MOD_RES
<222> LOCATION: (4)..(4)
<223> OTHER INFORMATION: d isomer
<220> FEATURE:
<221> NAME/KEY: MISC_FEATURE
<222> LOCATION: (5)..(5)
<223> OTHER INFORMATION: Xaa = 2Nal
<220> FEATURE:
<221> NAME/KEY: MOD_RES
<222> LOCATION: (7)..(7)
<223> OTHER INFORMATION: AMIDATION

<400> SEQUENCE: 67

Phe Tyr Xaa Arg Xaa Gly Glu
1 5

<210> SEQ ID NO 68
<211> LENGTH: 7
<212> TYPE: PRT
<213> ORGANISM: Artificial
<220> FEATURE:
<223> OTHER INFORMATION: Synthetic construct
<220> FEATURE:
<221> NAME/KEY: MOD_RES
<222> LOCATION: (1)..(7)
<223> OTHER INFORMATION: Lactam bridge
<220> FEATURE:
<221> NAME/KEY: MISC_FEATURE
<222> LOCATION: (3)..(3)
<223> OTHER INFORMATION: Xaa = Lys(iPr)
<220> FEATURE:
<221> NAME/KEY: MOD_RES
<222> LOCATION: (4)..(4)
<223> OTHER INFORMATION: d isomer
<220> FEATURE:

<221> NAME/KEY: MISC_FEATURE
<222> LOCATION: (5)..(5)
<223> OTHER INFORMATION: Xaa = 2Nal
<220> FEATURE:
<221> NAME/KEY: MOD_RES
<222> LOCATION: (7)..(7)
<223> OTHER INFORMATION: AMIDATION

<400> SEQUENCE: 68

Phe Tyr Xaa Arg Xaa Gly Glu
1 5

<210> SEQ ID NO 69
<211> LENGTH: 7
<212> TYPE: PRT
<213> ORGANISM: Artificial
<220> FEATURE:
<223> OTHER INFORMATION: Synthetic construct
<220> FEATURE:
<221> NAME/KEY: MOD_RES
<222> LOCATION: (1)..(7)
<223> OTHER INFORMATION: Lactam bridge
<220> FEATURE:
<221> NAME/KEY: MOD_RES
<222> LOCATION: (1)..(1)
<223> OTHER INFORMATION: d isomer
<220> FEATURE:
<221> NAME/KEY: MISC_FEATURE
<222> LOCATION: (3)..(3)
<223> OTHER INFORMATION: Xaa = Lys(iPr)
<220> FEATURE:
<221> NAME/KEY: MOD_RES
<222> LOCATION: (4)..(4)
<223> OTHER INFORMATION: d isomer
<220> FEATURE:
<221> NAME/KEY: MISC_FEATURE
<222> LOCATION: (5)..(5)
<223> OTHER INFORMATION: Xaa = 2Nal
<220> FEATURE:
<221> NAME/KEY: MOD_RES
<222> LOCATION: (7)..(7)
<223> OTHER INFORMATION: d isomer
<220> FEATURE:
<221> NAME/KEY: MOD_RES
<222> LOCATION: (7)..(7)
<223> OTHER INFORMATION: AMIDATION

<400> SEQUENCE: 69

Phe Tyr Xaa Arg Xaa Gly Glu
1 5

<210> SEQ ID NO 70
<211> LENGTH: 8
<212> TYPE: PRT
<213> ORGANISM: Artificial
<220> FEATURE:
<223> OTHER INFORMATION: Synthetic construct
<220> FEATURE:
<221> NAME/KEY: MOD_RES
<222> LOCATION: (1)..(7)
<223> OTHER INFORMATION: Lactam bridge
<220> FEATURE:
<221> NAME/KEY: MISC_FEATURE
<222> LOCATION: (3)..(3)
<223> OTHER INFORMATION: Xaa = Lys(iPr)
<220> FEATURE:
<221> NAME/KEY: MOD_RES
<222> LOCATION: (4)..(4)
<223> OTHER INFORMATION: d isomer
<220> FEATURE:
<221> NAME/KEY: MISC_FEATURE
<222> LOCATION: (5)..(5)
<223> OTHER INFORMATION: Xaa = 2Nal
<220> FEATURE:
<221> NAME/KEY: MOD_RES
<222> LOCATION: (7)..(7)

<223> OTHER INFORMATION: d isomer
<220> FEATURE:
<221> NAME/KEY: MISC_FEATURE
<222> LOCATION: (8)..(8)
<223> OTHER INFORMATION: Xaa = Lys(iPr)
<220> FEATURE:
<221> NAME/KEY: MOD_RES
<222> LOCATION: (8)..(8)
<223> OTHER INFORMATION: AMIDATION

<400> SEQUENCE: 70

Phe Tyr Xaa Arg Xaa Gly Glu Xaa
1 5

<210> SEQ ID NO 71
<211> LENGTH: 8
<212> TYPE: PRT
<213> ORGANISM: Artificial
<220> FEATURE:
<223> OTHER INFORMATION: Synthetic construct
<220> FEATURE:
<221> NAME/KEY: MOD_RES
<222> LOCATION: (1)..(7)
<223> OTHER INFORMATION: Lactam bridge
<220> FEATURE:
<221> NAME/KEY: MISC_FEATURE
<222> LOCATION: (3)..(3)
<223> OTHER INFORMATION: Xaa = Lys(iPr)
<220> FEATURE:
<221> NAME/KEY: MOD_RES
<222> LOCATION: (4)..(4)
<223> OTHER INFORMATION: d isomer
<220> FEATURE:
<221> NAME/KEY: MISC_FEATURE
<222> LOCATION: (5)..(5)
<223> OTHER INFORMATION: Xaa = 2Nal
<220> FEATURE:
<221> NAME/KEY: MOD_RES
<222> LOCATION: (7)..(7)
<223> OTHER INFORMATION: d isomer
<220> FEATURE:
<221> NAME/KEY: MISC_FEATURE
<222> LOCATION: (8)..(8)
<223> OTHER INFORMATION: Xaa = Lys(iPr)
<220> FEATURE:
<221> NAME/KEY: MOD_RES
<222> LOCATION: (8)..(8)
<223> OTHER INFORMATION: AMIDATION
<220> FEATURE:
<221> NAME/KEY: MISC_FEATURE
<222> LOCATION: (8)..(8)
<223> OTHER INFORMATION: acetic acid salt

<400> SEQUENCE: 71

Phe Tyr Xaa Arg Xaa Gly Glu Xaa
1 5

<210> SEQ ID NO 72
<211> LENGTH: 8
<212> TYPE: PRT
<213> ORGANISM: Artificial
<220> FEATURE:
<223> OTHER INFORMATION: Synthetic construct
<220> FEATURE:
<221> NAME/KEY: MOD_RES
<222> LOCATION: (1)..(7)
<223> OTHER INFORMATION: Lactam bridge
<220> FEATURE:
<221> NAME/KEY: MISC_FEATURE
<222> LOCATION: (3)..(3)
<223> OTHER INFORMATION: Xaa = Lys(iPr)
<220> FEATURE:
<221> NAME/KEY: MOD_RES
<222> LOCATION: (4)..(4)
<223> OTHER INFORMATION: d isomer
<220> FEATURE:

<221> NAME/KEY: MISC_FEATURE
<222> LOCATION: (5)..(5)
<223> OTHER INFORMATION: Xaa = 2Nal
<220> FEATURE:
<221> NAME/KEY: MOD_RES
<222> LOCATION: (7)..(7)
<223> OTHER INFORMATION: d isomer
<220> FEATURE:
<221> NAME/KEY: MOD_RES
<222> LOCATION: (8)..(8)
<223> OTHER INFORMATION: AMIDATION

<400> SEQUENCE: 72

Phe Tyr Xaa Arg Xaa Gly Glu Arg
1 5

<210> SEQ ID NO 73
<211> LENGTH: 7
<212> TYPE: PRT
<213> ORGANISM: Artificial
<220> FEATURE:
<223> OTHER INFORMATION: Synthetic construct
<220> FEATURE:
<221> NAME/KEY: MOD_RES
<222> LOCATION: (1)..(7)
<223> OTHER INFORMATION: Lactam bridge
<220> FEATURE:
<221> NAME/KEY: MISC_FEATURE
<222> LOCATION: (3)..(3)
<223> OTHER INFORMATION: Xaa = Lys(iPr)
<220> FEATURE:
<221> NAME/KEY: MOD_RES
<222> LOCATION: (4)..(4)
<223> OTHER INFORMATION: d isomer
<220> FEATURE:
<221> NAME/KEY: MISC_FEATURE
<222> LOCATION: (5)..(5)
<223> OTHER INFORMATION: Xaa = 2Nal
<220> FEATURE:
<221> NAME/KEY: MOD_RES
<222> LOCATION: (7)..(7)
<223> OTHER INFORMATION: d isomer
<220> FEATURE:
<221> NAME/KEY: MOD_RES
<222> LOCATION: (7)..(7)
<223> OTHER INFORMATION: AMIDATION

<400> SEQUENCE: 73

Phe Tyr Xaa Arg Xaa Gly Glu
1 5

<210> SEQ ID NO 74
<211> LENGTH: 8
<212> TYPE: PRT
<213> ORGANISM: Artificial
<220> FEATURE:
<223> OTHER INFORMATION: Synthetic construct
<220> FEATURE:
<221> NAME/KEY: MOD_RES
<222> LOCATION: (1)..(7)
<223> OTHER INFORMATION: Lactam bridge
<220> FEATURE:
<221> NAME/KEY: MISC_FEATURE
<222> LOCATION: (3)..(3)
<223> OTHER INFORMATION: Xaa = Lys(iPr)
<220> FEATURE:
<221> NAME/KEY: MOD_RES
<222> LOCATION: (4)..(4)
<223> OTHER INFORMATION: d isomer
<220> FEATURE:
<221> NAME/KEY: MISC_FEATURE
<222> LOCATION: (5)..(5)
<223> OTHER INFORMATION: Xaa = 2Nal
<220> FEATURE:
<221> NAME/KEY: MOD_RES
<222> LOCATION: (7)..(7)

<223> OTHER INFORMATION: d isomer
<220> FEATURE:
<221> NAME/KEY: MISC_FEATURE
<222> LOCATION: (8)..(8)
<223> OTHER INFORMATION: Xaa = Lys(iPr)
<220> FEATURE:
<221> NAME/KEY: MOD_RES
<222> LOCATION: (8)..(8)
<223> OTHER INFORMATION: Amidated as NHEt

<400> SEQUENCE: 74

Phe Tyr Xaa Arg Xaa Gly Glu Xaa
1 5

<210> SEQ ID NO 75
<211> LENGTH: 8
<212> TYPE: PRT
<213> ORGANISM: Artificial
<220> FEATURE:
<223> OTHER INFORMATION: Synthetic construct
<220> FEATURE:
<221> NAME/KEY: MOD_RES
<222> LOCATION: (1)..(7)
<223> OTHER INFORMATION: Lactam bridge
<220> FEATURE:
<221> NAME/KEY: MISC_FEATURE
<222> LOCATION: (3)..(3)
<223> OTHER INFORMATION: Xaa = Lys(iPr)
<220> FEATURE:
<221> NAME/KEY: MOD_RES
<222> LOCATION: (4)..(4)
<223> OTHER INFORMATION: d isomer
<220> FEATURE:
<221> NAME/KEY: MISC_FEATURE
<222> LOCATION: (5)..(5)
<223> OTHER INFORMATION: Xaa = 2Nal
<220> FEATURE:
<221> NAME/KEY: MOD_RES
<222> LOCATION: (7)..(7)
<223> OTHER INFORMATION: d isomer
<220> FEATURE:
<221> NAME/KEY: MISC_FEATURE
<222> LOCATION: (8)..(8)
<223> OTHER INFORMATION: Xaa = Lys(iPr)
<220> FEATURE:
<221> NAME/KEY: MOD_RES
<222> LOCATION: (8)..(8)
<223> OTHER INFORMATION: Amidated as NHEt
<220> FEATURE:
<221> NAME/KEY: MISC_FEATURE
<222> LOCATION: (8)..(8)
<223> OTHER INFORMATION: acetic acid salt

<400> SEQUENCE: 75

Phe Tyr Xaa Arg Xaa Gly Glu Xaa
1 5

<210> SEQ ID NO 76
<211> LENGTH: 7
<212> TYPE: PRT
<213> ORGANISM: Artificial
<220> FEATURE:
<223> OTHER INFORMATION: Synthetic construct
<220> FEATURE:
<221> NAME/KEY: MOD_RES
<222> LOCATION: (1)..(7)
<223> OTHER INFORMATION: Lactam bridge
<220> FEATURE:
<221> NAME/KEY: MOD_RES
<222> LOCATION: (1)..(1)
<223> OTHER INFORMATION: d isomer
<220> FEATURE:
<221> NAME/KEY: MISC_FEATURE
<222> LOCATION: (3)..(3)
<223> OTHER INFORMATION: Xaa = Lys(iPr)
<220> FEATURE:

<221> NAME/KEY: MOD_RES
<222> LOCATION: (4)..(4)
<223> OTHER INFORMATION: d isomer
<220> FEATURE:
<221> NAME/KEY: MISC_FEATURE
<222> LOCATION: (5)..(5)
<223> OTHER INFORMATION: Xaa = 2Nal
<220> FEATURE:
<221> NAME/KEY: MOD_RES
<222> LOCATION: (7)..(7)
<223> OTHER INFORMATION: Amidated as NHEt

<400> SEQUENCE: 76

Ala Tyr Xaa Arg Xaa Gly Glu
1 5

<210> SEQ ID NO 77
<211> LENGTH: 7
<212> TYPE: PRT
<213> ORGANISM: Artificial
<220> FEATURE:
<223> OTHER INFORMATION: Synthetic construct
<220> FEATURE:
<221> NAME/KEY: MOD_RES
<222> LOCATION: (1)..(7)
<223> OTHER INFORMATION: Lactam bridge
<220> FEATURE:
<221> NAME/KEY: MISC_FEATURE
<222> LOCATION: (1)..(1)
<223> OTHER INFORMATION: Xaa = 2Nal
<220> FEATURE:
<221> NAME/KEY: MISC_FEATURE
<222> LOCATION: (3)..(3)
<223> OTHER INFORMATION: Xaa = Lys(iPr)
<220> FEATURE:
<221> NAME/KEY: MOD_RES
<222> LOCATION: (4)..(4)
<223> OTHER INFORMATION: d isomer
<220> FEATURE:
<221> NAME/KEY: MISC_FEATURE
<222> LOCATION: (5)..(5)
<223> OTHER INFORMATION: Xaa = 2Nal
<220> FEATURE:
<221> NAME/KEY: MOD_RES
<222> LOCATION: (7)..(7)
<223> OTHER INFORMATION: Amidated as NHEt

<400> SEQUENCE: 77

Xaa Tyr Xaa Arg Xaa Gly Glu
1 5

<210> SEQ ID NO 78
<211> LENGTH: 7
<212> TYPE: PRT
<213> ORGANISM: Artificial
<220> FEATURE:
<223> OTHER INFORMATION: Synthetic construct
<220> FEATURE:
<221> NAME/KEY: MOD_RES
<222> LOCATION: (1)..(7)
<223> OTHER INFORMATION: Lactam bridge
<220> FEATURE:
<221> NAME/KEY: MOD_RES
<222> LOCATION: (1)..(1)
<223> OTHER INFORMATION: d isomer
<220> FEATURE:
<221> NAME/KEY: MISC_FEATURE
<222> LOCATION: (3)..(3)
<223> OTHER INFORMATION: Xaa = Lys(iPr)
<220> FEATURE:
<221> NAME/KEY: MOD_RES
<222> LOCATION: (4)..(4)
<223> OTHER INFORMATION: d isomer
<220> FEATURE:
<221> NAME/KEY: MISC_FEATURE
<222> LOCATION: (5)..(5)

<223> OTHER INFORMATION: Xaa = 2Nal
<220> FEATURE:
<221> NAME/KEY: MOD_RES
<222> LOCATION: (7)..(7)
<223> OTHER INFORMATION: Amidated as NHEt

<400> SEQUENCE: 78

Phe Tyr Xaa Arg Xaa Gly Glu
1 5

<210> SEQ ID NO 79
<211> LENGTH: 7
<212> TYPE: PRT
<213> ORGANISM: Artificial
<220> FEATURE:
<223> OTHER INFORMATION: Synthetic construct
<220> FEATURE:
<221> NAME/KEY: MOD_RES
<222> LOCATION: (1)..(7)
<223> OTHER INFORMATION: Lactam bridge
<220> FEATURE:
<221> NAME/KEY: MISC_FEATURE
<222> LOCATION: (3)..(3)
<223> OTHER INFORMATION: Xaa = Lys(iPr)
<220> FEATURE:
<221> NAME/KEY: MOD_RES
<222> LOCATION: (4)..(4)
<223> OTHER INFORMATION: d isomer
<220> FEATURE:
<221> NAME/KEY: MISC_FEATURE
<222> LOCATION: (5)..(5)
<223> OTHER INFORMATION: Xaa = 2Nal
<220> FEATURE:
<221> NAME/KEY: MOD_RES
<222> LOCATION: (7)..(7)
<223> OTHER INFORMATION: Amidated as NHEt

<400> SEQUENCE: 79

Phe Tyr Xaa Arg Xaa Gly Glu
1 5

<210> SEQ ID NO 80
<211> LENGTH: 9
<212> TYPE: PRT
<213> ORGANISM: Artificial
<220> FEATURE:
<223> OTHER INFORMATION: Synthetic construct
<220> FEATURE:
<221> NAME/KEY: MOD_RES
<222> LOCATION: (1)..(7)
<223> OTHER INFORMATION: Lactam bridge
<220> FEATURE:
<221> NAME/KEY: MISC_FEATURE
<222> LOCATION: (3)..(3)
<223> OTHER INFORMATION: Xaa = Lys(iPr)
<220> FEATURE:
<221> NAME/KEY: MOD_RES
<222> LOCATION: (4)..(4)
<223> OTHER INFORMATION: d isomer
<220> FEATURE:
<221> NAME/KEY: MISC_FEATURE
<222> LOCATION: (5)..(5)
<223> OTHER INFORMATION: Xaa = 2Nal
<220> FEATURE:
<221> NAME/KEY: MOD_RES
<222> LOCATION: (7)..(7)
<223> OTHER INFORMATION: d isomer
<220> FEATURE:
<221> NAME/KEY: MISC_FEATURE
<222> LOCATION: (9)..(9)
<223> OTHER INFORMATION: Xaa = 2Nal
<220> FEATURE:
<221> NAME/KEY: MOD_RES
<222> LOCATION: (9)..(9)
<223> OTHER INFORMATION: AMIDATION

<400> SEQUENCE: 80

Gly Tyr Xaa Arg Xaa Gly Glu Gly Xaa
1 5

<210> SEQ ID NO 81
<211> LENGTH: 9
<212> TYPE: PRT
<213> ORGANISM: Artificial
<220> FEATURE:
<223> OTHER INFORMATION: Synthetic construct
<220> FEATURE:
<221> NAME/KEY: MOD_RES
<222> LOCATION: (1)..(7)
<223> OTHER INFORMATION: Lactam bridge
<220> FEATURE:
<221> NAME/KEY: MISC_FEATURE
<222> LOCATION: (3)..(3)
<223> OTHER INFORMATION: Xaa = Lys(iPr)
<220> FEATURE:
<221> NAME/KEY: MOD_RES
<222> LOCATION: (4)..(4)
<223> OTHER INFORMATION: d isomer
<220> FEATURE:
<221> NAME/KEY: MISC_FEATURE
<222> LOCATION: (5)..(5)
<223> OTHER INFORMATION: Xaa = 2Nal
<220> FEATURE:
<221> NAME/KEY: MISC_FEATURE
<222> LOCATION: (8)..(8)
<223> OTHER INFORMATION: Xaa = beta-Ala
<220> FEATURE:
<221> NAME/KEY: MISC_FEATURE
<222> LOCATION: (9)..(9)
<223> OTHER INFORMATION: Xaa = d isomer 2Nal
<220> FEATURE:
<221> NAME/KEY: MOD_RES
<222> LOCATION: (9)..(9)
<223> OTHER INFORMATION: AMIDATION

<400> SEQUENCE: 81

Gly Tyr Xaa Arg Xaa Gly Glu Xaa Xaa
1 5

<210> SEQ ID NO 82
<211> LENGTH: 8
<212> TYPE: PRT
<213> ORGANISM: Artificial
<220> FEATURE:
<223> OTHER INFORMATION: Synthetic construct
<220> FEATURE:
<221> NAME/KEY: MOD_RES
<222> LOCATION: (1)..(7)
<223> OTHER INFORMATION: Lactam bridge
<220> FEATURE:
<221> NAME/KEY: MISC_FEATURE
<222> LOCATION: (1)..(1)
<223> OTHER INFORMATION: Xaa = beta-Ala
<220> FEATURE:
<221> NAME/KEY: MOD_RES
<222> LOCATION: (4)..(4)
<223> OTHER INFORMATION: d isomer
<220> FEATURE:
<221> NAME/KEY: MISC_FEATURE
<222> LOCATION: (5)..(5)
<223> OTHER INFORMATION: Xaa = 2Nal
<220> FEATURE:
<221> NAME/KEY: MOD_RES
<222> LOCATION: (8)..(8)
<223> OTHER INFORMATION: AMIDATION

<400> SEQUENCE: 82

Xaa Tyr Arg Arg Xaa Gly Glu Arg
1 5

<210> SEQ ID NO 83
<211> LENGTH: 8
<212> TYPE: PRT
<213> ORGANISM: Artificial
<220> FEATURE:
<223> OTHER INFORMATION: Synthetic construct
<220> FEATURE:
<221> NAME/KEY: MOD_RES
<222> LOCATION: (1)..(7)
<223> OTHER INFORMATION: Lactam bridge
<220> FEATURE:
<221> NAME/KEY: MISC_FEATURE
<222> LOCATION: (1)..(1)
<223> OTHER INFORMATION: Xaa = beta-Ala
<220> FEATURE:
<221> NAME/KEY: MOD_RES
<222> LOCATION: (4)..(4)
<223> OTHER INFORMATION: d isomer
<220> FEATURE:
<221> NAME/KEY: MISC_FEATURE
<222> LOCATION: (5)..(5)
<223> OTHER INFORMATION: Xaa = 2Nal
<220> FEATURE:
<221> NAME/KEY: MOD_RES
<222> LOCATION: (8)..(8)
<223> OTHER INFORMATION: AMIDATION

<400> SEQUENCE: 83

Xaa Tyr Arg Arg Xaa Gly Asp Arg
1 5

<210> SEQ ID NO 84
<211> LENGTH: 7
<212> TYPE: PRT
<213> ORGANISM: Artificial
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: 5-aminovaleryl modified
<220> FEATURE:
<221> NAME/KEY: MOD_RES
<222> LOCATION: (1)..(6)
<223> OTHER INFORMATION: Lactam bridge
<220> FEATURE:
<221> NAME/KEY: MOD_RES
<222> LOCATION: (3)..(3)
<223> OTHER INFORMATION: d isomer
<220> FEATURE:
<221> NAME/KEY: MISC_FEATURE
<222> LOCATION: (4)..(4)
<223> OTHER INFORMATION: Xaa = 2Nal
<220> FEATURE:
<221> NAME/KEY: MOD_RES
<222> LOCATION: (7)..(7)
<223> OTHER INFORMATION: AMIDATION

<400> SEQUENCE: 84

Tyr Arg Arg Xaa Gly Glu Arg
1 5

<210> SEQ ID NO 85
<211> LENGTH: 7
<212> TYPE: PRT
<213> ORGANISM: Artificial
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: 5-aminovaleryl modified
<220> FEATURE:
<221> NAME/KEY: MOD_RES
<222> LOCATION: (1)..(6)
<223> OTHER INFORMATION: Lactam bridge <220> FEATURE:
<221> NAME/KEY: MOD_RES
<222> LOCATION: (3)..(3)
<223> OTHER INFORMATION: d isomer
<220> FEATURE:
<221> NAME/KEY: MISC_FEATURE
<222> LOCATION: (4)..(4)
<223> OTHER INFORMATION: Xaa = 2Nal
<220> FEATURE:
<221> NAME/KEY: MOD_RES
<222> LOCATION: (7)..(7)
<223> OTHER INFORMATION: AMIDATION

<400> SEQUENCE: 85

Tyr Arg Arg Xaa Gly Asp Arg
1 5

<210> SEQ ID NO 86
<211> LENGTH: 7
<212> TYPE: PRT
<213> ORGANISM: Artificial
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: 4-AMPA modified
<220> FEATURE:
<221> NAME/KEY: MOD_RES
<222> LOCATION: (1)..(6)
<223> OTHER INFORMATION: Lactam bridge
<220> FEATURE:
<221> NAME/KEY: MOD_RES
<222> LOCATION: (3)..(3)
<223> OTHER INFORMATION: d isomer
<220> FEATURE:
<221> NAME/KEY: MISC_FEATURE
<222> LOCATION: (4)..(4)
<223> OTHER INFORMATION: Xaa = 2 Nal
<220> FEATURE:
<221> NAME/KEY: MOD_RES
<222> LOCATION: (7)..(7)
<223> OTHER INFORMATION: AMIDATION

<400> SEQUENCE: 86

Tyr Arg Arg Xaa Gly Asp Arg
1 5

<210> SEQ ID NO 87
<211> LENGTH: 7
<212> TYPE: PRT
<213> ORGANISM: Artificial
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: 4-AMPA modified
<220> FEATURE:
<221> NAME/KEY: MOD_RES
<222> LOCATION: (1)..(6)
<223> OTHER INFORMATION: Lactam bridge
<220> FEATURE:
<221> NAME/KEY: MOD_RES
<222> LOCATION: (3)..(3)
<223> OTHER INFORMATION: d isomer
<220> FEATURE:
<221> NAME/KEY: MISC_FEATURE
<222> LOCATION: (4)..(4)
<223> OTHER INFORMATION: Xaa = 2Nal
<220> FEATURE:
<221> NAME/KEY: MOD_RES
<222> LOCATION: (7)..(7)
<223> OTHER INFORMATION: AMIDATION

<400> SEQUENCE: 87

Tyr Arg Arg Xaa Gly Glu Arg
1 5

<210> SEQ ID NO 88
<211> LENGTH: 7
<212> TYPE: PRT
<213> ORGANISM: Artificial
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: 4-AMPA modified
<220> FEATURE:
<221> NAME/KEY: MOD_RES
<222> LOCATION: (1)..(6)
<223> OTHER INFORMATION: Lactam bridge
<220> FEATURE:
<221> NAME/KEY: MOD_RES
<222> LOCATION: (3)..(3)
<223> OTHER INFORMATION: d isomer
<220> FEATURE:
<221> NAME/KEY: MISC_FEATURE
<222> LOCATION: (4)..(4)
<223> OTHER INFORMATION: Xaa = 2Nal
<220> FEATURE:
<221> NAME/KEY: MOD_RES
<222> LOCATION: (7)..(7)
<223> OTHER INFORMATION: d isomer
<220> FEATURE:
<221> NAME/KEY: MOD_RES
<222> LOCATION: (7)..(7)
<223> OTHER INFORMATION: AMIDATION

<400> SEQUENCE: 88

Tyr Arg Arg Xaa Gly Glu Arg
1 5

<210> SEQ ID NO 89
<211> LENGTH: 7
<212> TYPE: PRT
<213> ORGANISM: Artificial
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: 4-AMB modified
<220> FEATURE:
<221> NAME/KEY: MOD_RES
<222> LOCATION: (1)..(6)
<223> OTHER INFORMATION: Lactam bridge
<220> FEATURE:
<221> NAME/KEY: MOD_RES
<222> LOCATION: (3)..(3)
<223> OTHER INFORMATION: d isomer
<220> FEATURE:
<221> NAME/KEY: MISC_FEATURE
<222> LOCATION: (4)..(4)
<223> OTHER INFORMATION: Xaa = 2Nal
<220> FEATURE:
<221> NAME/KEY: MOD_RES
<222> LOCATION: (7)..(7)
<223> OTHER INFORMATION: AMIDATION

<400> SEQUENCE: 89

Tyr Arg Arg Xaa Gly Glu Arg
1 5

<210> SEQ ID NO 90
<211> LENGTH: 10
<212> TYPE: PRT
<213> ORGANISM: Artificial
<220> FEATURE:

<223> OTHER INFORMATION: Synthetic construct
<220> FEATURE:
<221> NAME/KEY: MOD_RES
<222> LOCATION: (1)..(7)
<223> OTHER INFORMATION: Lactam bridge
<220> FEATURE:
<221> NAME/KEY: MISC_FEATURE
<222> LOCATION: (3)..(3)
<223> OTHER INFORMATION: Xaa = Lys(iPr)
<220> FEATURE:
<221> NAME/KEY: MOD_RES
<222> LOCATION: (4)..(4)
<223> OTHER INFORMATION: d isomer
<220> FEATURE:
<221> NAME/KEY: MISC_FEATURE
<222> LOCATION: (5)..(5)
<223> OTHER INFORMATION: Xaa = 2Nal
<220> FEATURE:
<221> NAME/KEY: MOD_RES
<222> LOCATION: (7)..(7)
<223> OTHER INFORMATION: d isomer
<220> FEATURE:
<221> NAME/KEY: MISC_FEATURE
<222> LOCATION: (8)..(8)
<223> OTHER INFORMATION: Xaa = Lys(iPr)
<220> FEATURE:
<221> NAME/KEY: MISC_FEATURE
<222> LOCATION: (10)..(10)
<223> OTHER INFORMATION: Xaa = 2Nal
<220> FEATURE:
<221> NAME/KEY: MOD_RES
<222> LOCATION: (10)..(10)
<223> OTHER INFORMATION: AMIDATION

<400> SEQUENCE: 90

Gly Tyr Xaa Arg Xaa Gly Glu Xaa Gly Xaa
1 5 10

<210> SEQ ID NO 91
<211> LENGTH: 10
<212> TYPE: PRT
<213> ORGANISM: Artificial
<220> FEATURE:
<223> OTHER INFORMATION: Synthetic construct
<220> FEATURE:
<221> NAME/KEY: MOD_RES
<222> LOCATION: (1)..(7)
<223> OTHER INFORMATION: Lactam bridge
<220> FEATURE:
<221> NAME/KEY: MISC_FEATURE
<222> LOCATION: (3)..(3)
<223> OTHER INFORMATION: Xaa = Lys(iPr)
<220> FEATURE:
<221> NAME/KEY: MOD_RES
<222> LOCATION: (4)..(4)
<223> OTHER INFORMATION: d isomer
<220> FEATURE:
<221> NAME/KEY: MISC_FEATURE
<222> LOCATION: (5)..(5)
<223> OTHER INFORMATION: Xaa = 2Nal
<220> FEATURE:
<221> NAME/KEY: MOD_RES
<222> LOCATION: (7)..(7)
<223> OTHER INFORMATION: d isomer
<220> FEATURE:
<221> NAME/KEY: MISC_FEATURE
<222> LOCATION: (8)..(8)
<223> OTHER INFORMATION: Xaa = Lys(iPr)
<220> FEATURE:
<221> NAME/KEY: MISC_FEATURE
<222> LOCATION: (10)..(10)
<223> OTHER INFORMATION: Xaa = 2Nal
<220> FEATURE:
<221> NAME/KEY: MOD_RES
<222> LOCATION: (10)..(10)
<223> OTHER INFORMATION: AMIDATION

<400> SEQUENCE: 91

```
Phe Tyr Xaa Arg Xaa Gly Glu Xaa Gly Xaa
1               5                   10


<210> SEQ ID NO 92
<211> LENGTH: 9
<212> TYPE: PRT
<213> ORGANISM: Artificial
<220> FEATURE:
<223> OTHER INFORMATION: Synthetic construct
<220> FEATURE:
<221> NAME/KEY: MOD_RES
<222> LOCATION: (1)..(7)
<223> OTHER INFORMATION: Lactam bridge
<220> FEATURE:
<221> NAME/KEY: MISC_FEATURE
<222> LOCATION: (3)..(3)
<223> OTHER INFORMATION: Xaa = Lys(iPr)
<220> FEATURE:
<221> NAME/KEY: MOD_RES
<222> LOCATION: (4)..(4)
<223> OTHER INFORMATION: d isomer
<220> FEATURE:
<221> NAME/KEY: MISC_FEATURE
<222> LOCATION: (5)..(5)
<223> OTHER INFORMATION: Xaa = 2Nal
<220> FEATURE:
<221> NAME/KEY: MOD_RES
<222> LOCATION: (7)..(7)
<223> OTHER INFORMATION: d isomer
<220> FEATURE:
<221> NAME/KEY: MOD_RES
<222> LOCATION: (9)..(9)
<223> OTHER INFORMATION: d isomer
<220> FEATURE:
<221> NAME/KEY: MOD_RES
<222> LOCATION: (9)..(9)
<223> OTHER INFORMATION: AMIDATION

<400> SEQUENCE: 92

Gly Tyr Xaa Arg Xaa Gly Glu Gly Phe
1               5


<210> SEQ ID NO 93
<211> LENGTH: 9
<212> TYPE: PRT
<213> ORGANISM: Artificial
<220> FEATURE:
<223> OTHER INFORMATION: Synthetic construct
<220> FEATURE:
<221> NAME/KEY: MOD_RES
<222> LOCATION: (1)..(7)
<223> OTHER INFORMATION: Lactam bridge
<220> FEATURE:
<221> NAME/KEY: MISC_FEATURE
<222> LOCATION: (3)..(3)
<223> OTHER INFORMATION: Xaa = Lys(iPr)
<220> FEATURE:
<221> NAME/KEY: MOD_RES
<222> LOCATION: (4)..(4)
<223> OTHER INFORMATION: d isomer
<220> FEATURE:
<221> NAME/KEY: MISC_FEATURE
<222> LOCATION: (5)..(5)
<223> OTHER INFORMATION: Xaa = 2Nal
<220> FEATURE:
<221> NAME/KEY: MOD_RES
<222> LOCATION: (7)..(7)
<223> OTHER INFORMATION: d isomer
<220> FEATURE:
<221> NAME/KEY: MISC_FEATURE
<222> LOCATION: (8)..(8)
<223> OTHER INFORMATION: Xaa = Lys(iPr)
<220> FEATURE:
<221> NAME/KEY: MOD_RES
<222> LOCATION: (9)..(9)
<223> OTHER INFORMATION: d isomer
```

<220> FEATURE:
<221> NAME/KEY: MOD_RES
<222> LOCATION: (9)..(9)
<223> OTHER INFORMATION: AMIDATION

<400> SEQUENCE: 93

Gly Tyr Xaa Arg Xaa Gly Glu Xaa Phe
1 5

<210> SEQ ID NO 94
<211> LENGTH: 8
<212> TYPE: PRT
<213> ORGANISM: Artificial
<220> FEATURE:
<223> OTHER INFORMATION: Synthetic construct
<220> FEATURE:
<221> NAME/KEY: MOD_RES
<222> LOCATION: (1)..(7)
<223> OTHER INFORMATION: Lactam bridge
<220> FEATURE:
<221> NAME/KEY: MISC_FEATURE
<222> LOCATION: (3)..(3)
<223> OTHER INFORMATION: Xaa = Lys(iPr)
<220> FEATURE:
<221> NAME/KEY: MOD_RES
<222> LOCATION: (4)..(4)
<223> OTHER INFORMATION: d isomer
<220> FEATURE:
<221> NAME/KEY: MISC_FEATURE
<222> LOCATION: (5)..(5)
<223> OTHER INFORMATION: Xaa = 2Nal
<220> FEATURE:
<221> NAME/KEY: MOD_RES
<222> LOCATION: (7)..(7)
<223> OTHER INFORMATION: d isomer
<220> FEATURE:
<221> NAME/KEY: MISC_FEATURE
<222> LOCATION: (8)..(8)
<223> OTHER INFORMATION: Xaa = Lys(iPr)
<220> FEATURE:
<221> NAME/KEY: MOD_RES
<222> LOCATION: (8)..(8)
<223> OTHER INFORMATION: AMIDATION

<400> SEQUENCE: 94

Lys Tyr Xaa Arg Xaa Gly Glu Xaa
1 5

<210> SEQ ID NO 95
<211> LENGTH: 8
<212> TYPE: PRT
<213> ORGANISM: Artificial
<220> FEATURE:
<223> OTHER INFORMATION: Synthetic construct
<220> FEATURE:
<221> NAME/KEY: MOD_RES
<222> LOCATION: (1)..(7)
<223> OTHER INFORMATION: Lactam bridge
<220> FEATURE:
<221> NAME/KEY: MOD_RES
<222> LOCATION: (4)..(4)
<223> OTHER INFORMATION: d isomer
<220> FEATURE:
<221> NAME/KEY: MISC_FEATURE
<222> LOCATION: (5)..(5)
<223> OTHER INFORMATION: Xaa = 2Nal
<220> FEATURE:
<221> NAME/KEY: MOD_RES
<222> LOCATION: (7)..(7)
<223> OTHER INFORMATION: d isomer
<220> FEATURE:
<221> NAME/KEY: MISC_FEATURE
<222> LOCATION: (8)..(8)
<223> OTHER INFORMATION: Xaa = Lys(iPr)
<220> FEATURE:
<221> NAME/KEY: MOD_RES

<222> LOCATION: (8)..(8)
<223> OTHER INFORMATION: AMIDATION

<400> SEQUENCE: 95

Phe Tyr Lys Arg Xaa Gly Glu Xaa
1 5

<210> SEQ ID NO 96
<211> LENGTH: 8
<212> TYPE: PRT
<213> ORGANISM: Artificial
<220> FEATURE:
<223> OTHER INFORMATION: Synthetic construct
<220> FEATURE:
<221> NAME/KEY: MOD_RES
<222> LOCATION: (1)..(7)
<223> OTHER INFORMATION: Lactam bridge
<220> FEATURE:
<221> NAME/KEY: MISC_FEATURE
<222> LOCATION: (3)..(3)
<223> OTHER INFORMATION: Xaa = Lys(iPr)
<220> FEATURE:
<221> NAME/KEY: MOD_RES
<222> LOCATION: (4)..(4)
<223> OTHER INFORMATION: d isomer
<220> FEATURE:
<221> NAME/KEY: MISC_FEATURE
<222> LOCATION: (5)..(5)
<223> OTHER INFORMATION: Xaa = 2Nal
<220> FEATURE:
<221> NAME/KEY: MOD_RES
<222> LOCATION: (7)..(7)
<223> OTHER INFORMATION: d isomer
<220> FEATURE:
<221> NAME/KEY: MOD_RES
<222> LOCATION: (8)..(8)
<223> OTHER INFORMATION: AMIDATION

<400> SEQUENCE: 96

Phe Tyr Xaa Arg Xaa Gly Glu Lys
1 5

<210> SEQ ID NO 97
<211> LENGTH: 8
<212> TYPE: PRT
<213> ORGANISM: Artificial
<220> FEATURE:
<223> OTHER INFORMATION: Synthetic construct
<220> FEATURE:
<221> NAME/KEY: MOD_RES
<222> LOCATION: (1)..(7)
<223> OTHER INFORMATION: Lactam bridge
<220> FEATURE:
<221> NAME/KEY: MISC_FEATURE
<222> LOCATION: (3)..(3)
<223> OTHER INFORMATION: Xaa = Lys(iPr)
<220> FEATURE:
<221> NAME/KEY: MOD_RES
<222> LOCATION: (4)..(4)
<223> OTHER INFORMATION: d isomer
<220> FEATURE:
<221> NAME/KEY: MISC_FEATURE
<222> LOCATION: (5)..(5)
<223> OTHER INFORMATION: Xaa = 2Nal
<220> FEATURE:
<221> NAME/KEY: MOD_RES
<222> LOCATION: (7)..(7)
<223> OTHER INFORMATION: d isomer
<220> FEATURE:
<221> NAME/KEY: MISC_FEATURE
<222> LOCATION: (8)..(8)
<223> OTHER INFORMATION: Xaa = Orn
<220> FEATURE:
<221> NAME/KEY: MOD_RES
<222> LOCATION: (8)..(8)
<223> OTHER INFORMATION: AMIDATION

<400> SEQUENCE: 97

Phe Tyr Xaa Arg Xaa Gly Glu Xaa
1 5

<210> SEQ ID NO 98
<211> LENGTH: 8
<212> TYPE: PRT
<213> ORGANISM: Artificial
<220> FEATURE:
<223> OTHER INFORMATION: Synthetic construct
<220> FEATURE:
<221> NAME/KEY: MOD_RES
<222> LOCATION: (1)..(7)
<223> OTHER INFORMATION: Lactam bridge
<220> FEATURE:
<221> NAME/KEY: MOD_RES
<222> LOCATION: (4)..(4)
<223> OTHER INFORMATION: d isomer
<220> FEATURE:
<221> NAME/KEY: MISC_FEATURE
<222> LOCATION: (5)..(5)
<223> OTHER INFORMATION: Xaa = 2Nal
<220> FEATURE:
<221> NAME/KEY: MOD_RES
<222> LOCATION: (7)..(7)
<223> OTHER INFORMATION: d isomer
<220> FEATURE:
<221> NAME/KEY: MOD_RES
<222> LOCATION: (8)..(8)
<223> OTHER INFORMATION: AMIDATION

<400> SEQUENCE: 98

Phe Tyr Lys Arg Xaa Gly Glu Lys
1 5

<210> SEQ ID NO 99
<211> LENGTH: 8
<212> TYPE: PRT
<213> ORGANISM: Artificial
<220> FEATURE:
<223> OTHER INFORMATION: Synthetic construct
<220> FEATURE:
<221> NAME/KEY: MOD_RES
<222> LOCATION: (1)..(7)
<223> OTHER INFORMATION: Lactam bridge
<220> FEATURE:
<221> NAME/KEY: MOD_RES
<222> LOCATION: (4)..(4)
<223> OTHER INFORMATION: d isomer
<220> FEATURE:
<221> NAME/KEY: MISC_FEATURE
<222> LOCATION: (5)..(5)
<223> OTHER INFORMATION: Xaa = 2Nal
<220> FEATURE:
<221> NAME/KEY: MOD_RES
<222> LOCATION: (7)..(7)
<223> OTHER INFORMATION: d isomer
<220> FEATURE:
<221> NAME/KEY: MOD_RES
<222> LOCATION: (8)..(8)
<223> OTHER INFORMATION: Amidated as NHEt

<400> SEQUENCE: 99

Phe Tyr Lys Arg Xaa Gly Glu Lys
1 5

<210> SEQ ID NO 100
<211> LENGTH: 8
<212> TYPE: PRT
<213> ORGANISM: Artificial
<220> FEATURE:
<223> OTHER INFORMATION: Synthetic construct
<220> FEATURE:

<221> NAME/KEY: MOD_RES
<222> LOCATION: (1)..(1)
<223> OTHER INFORMATION: FMOC modified
<220> FEATURE:
<221> NAME/KEY: MISC_FEATURE
<222> LOCATION: (2)..(2)
<223> OTHER INFORMATION: Xaa = Tyr(tBu)
<220> FEATURE:
<221> NAME/KEY: MISC_FEATURE
<222> LOCATION: (3)..(3)
<223> OTHER INFORMATION: Xaa = Lys(Boc)
<220> FEATURE:
<221> NAME/KEY: MISC_FEATURE
<222> LOCATION: (4)..(4)
<223> OTHER INFORMATION: Xaa = d isomer Arg(Pbf)
<220> FEATURE:
<221> NAME/KEY: MISC_FEATURE
<222> LOCATION: (5)..(5)
<223> OTHER INFORMATION: Xaa = 2Nal
<220> FEATURE:
<221> NAME/KEY: MISC_FEATURE
<222> LOCATION: (7)..(7)
<223> OTHER INFORMATION: Xaa = d isomer Glu(OAllyl)
<220> FEATURE:
<221> NAME/KEY: MISC_FEATURE
<222> LOCATION: (8)..(8)
<223> OTHER INFORMATION: Xaa = Lys(Boc)
<220> FEATURE:
<221> NAME/KEY: MOD_RES
<222> LOCATION: (8)..(8)
<223> OTHER INFORMATION: AMIDATION

<400> SEQUENCE: 100

Phe Xaa Xaa Xaa Xaa Gly Xaa Xaa
1 5

<210> SEQ ID NO 101
<211> LENGTH: 8
<212> TYPE: PRT
<213> ORGANISM: artificial
<220> FEATURE:
<223> OTHER INFORMATION: Synthetic construct
<220> FEATURE:
<221> NAME/KEY: MOD_RES
<222> LOCATION: (1)..(7)
<223> OTHER INFORMATION: lactam bridge
<220> FEATURE:
<221> NAME/KEY: MISC_FEATURE
<222> LOCATION: (2)..(2)
<223> OTHER INFORMATION: Xaa = Tyr(tBu)
<220> FEATURE:
<221> NAME/KEY: MISC_FEATURE
<222> LOCATION: (3)..(3)
<223> OTHER INFORMATION: Xaa = Lys(Boc)
<220> FEATURE:
<221> NAME/KEY: MISC_FEATURE
<222> LOCATION: (4)..(4)
<223> OTHER INFORMATION: Xaa = d isomer Arg(Pbf)
<220> FEATURE:
<221> NAME/KEY: MISC_FEATURE
<222> LOCATION: (5)..(5)
<223> OTHER INFORMATION: Xaa = 2Nal
<220> FEATURE:
<221> NAME/KEY: MOD_RES
<222> LOCATION: (7)..(7)
<223> OTHER INFORMATION: d isomer
<220> FEATURE:
<221> NAME/KEY: MISC_FEATURE
<222> LOCATION: (8)..(8)
<223> OTHER INFORMATION: Xaa = Lys(Boc)
<220> FEATURE:
<221> NAME/KEY: MOD_RES
<222> LOCATION: (8)..(8)
<223> OTHER INFORMATION: AMIDATION

<400> SEQUENCE: 101

Phe Xaa Xaa Xaa Xaa Gly Glu Xaa 1 5

<210> SEQ ID NO 102
<211> LENGTH: 8
<212> TYPE: PRT
<213> ORGANISM: artificial
<220> FEATURE:
<223> OTHER INFORMATION: synthetic construct
<220> FEATURE:
<221> NAME/KEY: MOD_RES
<222> LOCATION: (1)..(1)
<223> OTHER INFORMATION: Fmoc modified
<220> FEATURE:
<221> NAME/KEY: MISC_FEATURE
<222> LOCATION: (2)..(2)
<223> OTHER INFORMATION: Xaa = Tyr(2-Br-Z)
<220> FEATURE:
<221> NAME/KEY: MISC_FEATURE
<222> LOCATION: (3)..(3)
<223> OTHER INFORMATION: Xaa = Lys(2-Cl-Z)
<220> FEATURE:
<221> NAME/KEY: MISC_FEATURE
<222> LOCATION: (4)..(4)
<223> OTHER INFORMATION: Xaa = d isomer Arg(Tos)
<220> FEATURE:
<221> NAME/KEY: MISC_FEATURE
<222> LOCATION: (5)..(5)
<223> OTHER INFORMATION: Xaa = 2Nal
<220> FEATURE:
<221> NAME/KEY: MISC_FEATURE
<222> LOCATION: (7)..(7)
<223> OTHER INFORMATION: Xaa = d isomer Glu(OFm)
<220> FEATURE:
<221> NAME/KEY: MISC_FEATURE
<222> LOCATION: (8)..(8)
<223> OTHER INFORMATION: Xaa = Lys(2-Cl-Z)

<400> SEQUENCE: 102

Phe Xaa Xaa Xaa Xaa Gly Xaa Xaa
1 5

<210> SEQ ID NO 103
<211> LENGTH: 8
<212> TYPE: PRT
<213> ORGANISM: artificial
<220> FEATURE:
<223> OTHER INFORMATION: synthetic construct
<220> FEATURE:
<221> NAME/KEY: MOD_RES
<222> LOCATION: (1)..(1)
<223> OTHER INFORMATION: Boc modified
<220> FEATURE:
<221> NAME/KEY: MISC_FEATURE
<222> LOCATION: (2)..(2)
<223> OTHER INFORMATION: Xaa = Tyr(2-Br-Z)
<220> FEATURE:
<221> NAME/KEY: MISC_FEATURE
<222> LOCATION: (3)..(3)
<223> OTHER INFORMATION: Xaa = Lys(Fmoc)
<220> FEATURE:
<221> NAME/KEY: MISC_FEATURE
<222> LOCATION: (4)..(4)
<223> OTHER INFORMATION: Xaa = d isomer Arg(Tos)
<220> FEATURE:
<221> NAME/KEY: MISC_FEATURE
<222> LOCATION: (5)..(5)
<223> OTHER INFORMATION: Xaa = 2Nal
<220> FEATURE:
<221> NAME/KEY: MISC_FEATURE
<222> LOCATION: (7)..(7)
<223> OTHER INFORMATION: Xaa = d isomer Glu(OBzl)
<220> FEATURE:
<221> NAME/KEY: MISC_FEATURE
<222> LOCATION: (8)..(8)
<223> OTHER INFORMATION: Xaa = Lys(Fmoc)

<400> SEQUENCE: 103

Phe Xaa Xaa Xaa Xaa Gly Xaa Xaa
1 5

<210> SEQ ID NO 104
<211> LENGTH: 8
<212> TYPE: PRT
<213> ORGANISM: artificial
<220> FEATURE:
<223> OTHER INFORMATION: synthetic construct
<220> FEATURE:
<221> NAME/KEY: MISC_FEATURE
<222> LOCATION: (3)..(3)
<223> OTHER INFORMATION: Xaa = Lys(Fmoc)
<220> FEATURE:
<221> NAME/KEY: MOD_RES
<222> LOCATION: (4)..(4)
<223> OTHER INFORMATION: d isomer
<220> FEATURE:
<221> NAME/KEY: MISC_FEATURE
<222> LOCATION: (5)..(5)
<223> OTHER INFORMATION: Xaa = 2Nal
<220> FEATURE:
<221> NAME/KEY: MOD_RES
<222> LOCATION: (7)..(7)
<223> OTHER INFORMATION: d isomer
<220> FEATURE:
<221> NAME/KEY: MISC_FEATURE
<222> LOCATION: (8)..(8)
<223> OTHER INFORMATION: Xaa = Lys(Fmoc)
<220> FEATURE:
<221> NAME/KEY: MOD_RES
<222> LOCATION: (8)..(8)
<223> OTHER INFORMATION: AMIDATED

<400> SEQUENCE: 104

Phe Tyr Xaa Arg Xaa Gly Glu Xaa
1 5

<210> SEQ ID NO 105
<211> LENGTH: 8
<212> TYPE: PRT
<213> ORGANISM: artificial
<220> FEATURE:
<223> OTHER INFORMATION: synthetic construct
<220> FEATURE:
<221> NAME/KEY: MISC_FEATURE
<222> LOCATION: (2)..(2)
<223> OTHER INFORMATION: Xaa = Tyr(tBu)
<220> FEATURE:
<221> NAME/KEY: MISC_FEATURE
<222> LOCATION: (3)..(3)
<223> OTHER INFORMATION: Xaa = Lys(iPr,Boc)
<220> FEATURE:
<221> NAME/KEY: MISC_FEATURE
<222> LOCATION: (4)..(4)
<223> OTHER INFORMATION: Xaa = d isomer Arg(Pbf)
<220> FEATURE:
<221> NAME/KEY: MISC_FEATURE
<222> LOCATION: (5)..(5)
<223> OTHER INFORMATION: Xaa = 2Nal
<220> FEATURE:
<221> NAME/KEY: MISC_FEATURE
<222> LOCATION: (7)..(7)
<223> OTHER INFORMATION: Xaa = d isomer Glu(2-CTC resin)
<220> FEATURE:
<221> NAME/KEY: MISC_FEATURE
<222> LOCATION: (8)..(8)
<223> OTHER INFORMATION: Xaa = Lys(iPr,Z)
<220> FEATURE:
<221> NAME/KEY: MOD_RES
<222> LOCATION: (8)..(8)
<223> OTHER INFORMATION: AMIDATION

<400> SEQUENCE: 105

Phe Xaa Xaa Xaa Xaa Gly Xaa Xaa 1 5

<210> SEQ ID NO 106
<211> LENGTH: 8
<212> TYPE: PRT
<213> ORGANISM: artificial
<220> FEATURE:
<223> OTHER INFORMATION: synthetic construct
<220> FEATURE:
<221> NAME/KEY: MISC_FEATURE
<222> LOCATION: (2)..(2)
<223> OTHER INFORMATION: Xaa = Tyr(tBu)
<220> FEATURE:
<221> NAME/KEY: MISC_FEATURE
<222> LOCATION: (3)..(3)
<223> OTHER INFORMATION: Xaa = Lys(iPr,Boc)
<220> FEATURE:
<221> NAME/KEY: MISC_FEATURE
<222> LOCATION: (4)..(4)
<223> OTHER INFORMATION: Xaa = d isomer Arg(Pbf)
<220> FEATURE:
<221> NAME/KEY: MISC_FEATURE
<222> LOCATION: (5)..(5)
<223> OTHER INFORMATION: Xaa = 2Nal
<220> FEATURE:
<221> NAME/KEY: MISC_FEATURE
<222> LOCATION: (7)..(7)
<223> OTHER INFORMATION: Xaa = d isomer Glu(OH)
<220> FEATURE:
<221> NAME/KEY: MISC_FEATURE
<222> LOCATION: (8)..(8)
<223> OTHER INFORMATION: Xaa = Lys(iPr,Z)
<220> FEATURE:
<221> NAME/KEY: MOD_RES
<222> LOCATION: (8)..(8)
<223> OTHER INFORMATION: AMIDATION

<400> SEQUENCE: 106

Phe Xaa Xaa Xaa Xaa Gly Xaa Xaa
1 5

<210> SEQ ID NO 107
<211> LENGTH: 8
<212> TYPE: PRT
<213> ORGANISM: artificial
<220> FEATURE:
<223> OTHER INFORMATION: synthetic construct
<220> FEATURE:
<221> NAME/KEY: MOD_RES
<222> LOCATION: (1)..(7)
<223> OTHER INFORMATION: lactam bridge
<220> FEATURE:
<221> NAME/KEY: MISC_FEATURE
<222> LOCATION: (2)..(2)
<223> OTHER INFORMATION: Xaa = Tyr(tBu)
<220> FEATURE:
<221> NAME/KEY: MISC_FEATURE
<222> LOCATION: (3)..(3)
<223> OTHER INFORMATION: Xaa = Lys(iPr,Boc)
<220> FEATURE:
<221> NAME/KEY: MISC_FEATURE
<222> LOCATION: (4)..(4)
<223> OTHER INFORMATION: Xaa = d isomer Arg(Pbf)
<220> FEATURE:
<221> NAME/KEY: MISC_FEATURE
<222> LOCATION: (5)..(5)
<223> OTHER INFORMATION: Xaa = 2Nal
<220> FEATURE:
<221> NAME/KEY: MOD_RES
<222> LOCATION: (7)..(7)
<223> OTHER INFORMATION: d isomer
<220> FEATURE:
<221> NAME/KEY: MISC_FEATURE
<222> LOCATION: (8)..(8)
<223> OTHER INFORMATION: Xaa = Lys(iPr,Z)
<220> FEATURE:
<221> NAME/KEY: MOD_RES -continued

```
<222> LOCATION: (8)..(8)
<223> OTHER INFORMATION: AMIDATION

<400> SEQUENCE: 107

Phe Xaa Xaa Xaa Xaa Gly Glu Xaa
1               5


<210> SEQ ID NO 108
<211> LENGTH: 8
<212> TYPE: PRT
<213> ORGANISM: artificial
<220> FEATURE:
<223> OTHER INFORMATION: synthetic construct
<220> FEATURE:
<221> NAME/KEY: MOD_RES
<222> LOCATION: (1)..(7)
<223> OTHER INFORMATION: lactam bridge
<220> FEATURE:
<221> NAME/KEY: MISC_FEATURE
<222> LOCATION: (3)..(3)
<223> OTHER INFORMATION: Xaa = Lys(iPr-d6)
<220> FEATURE:
<221> NAME/KEY: MOD_RES
<222> LOCATION: (4)..(4)
<223> OTHER INFORMATION: d isomer
<220> FEATURE:
<221> NAME/KEY: MISC_FEATURE
<222> LOCATION: (5)..(5)
<223> OTHER INFORMATION: Xaa = 2Nal
<220> FEATURE:
<221> NAME/KEY: MOD_RES
<222> LOCATION: (7)..(7)
<223> OTHER INFORMATION: d isomer
<220> FEATURE:
<221> NAME/KEY: MISC_FEATURE
<222> LOCATION: (8)..(8)
<223> OTHER INFORMATION: Xaa = Lys(iPr-d6)
<220> FEATURE:
<221> NAME/KEY: MOD_RES
<222> LOCATION: (8)..(8)
<223> OTHER INFORMATION: AMIDATION

<400> SEQUENCE: 108

Phe Tyr Xaa Arg Xaa Gly Glu Xaa
1               5
```

What is claimed is:

1. A lactam-cyclized peptide of formula I:

(I) (SEQ ID NO: 1)

$R_1$-cyclo[$X_1$-Tyr-$X_3$-DArg-2Nal-Gly-$X_7$]-$X_8$-$X_9$-$X_{10}$-$R_2$ wherein:

a) said lactam is formed by an amide bond between the side chain amino group of $X_1$ and the side chain carboxyl group of $X_7$, wherein $X_1$ and $X_7$ are, respectively, a pair selected from the group consisting of (D/L)Agl/Glu, Dab/Glu, and Dap/Glu, and $R_1$ is Ac or n-hexanoyl; or b) said lactam is formed by an amide bond between the side chain carboxyl group of $X_1$ and the side chain amino group of $X_7$, wherein $X_1$ and $X_7$ are, respectively, a pair selected from the group consisting of Asp/(D/L)Agl, Asp/Dab, Asp/Dap, Glu/(D/L)Agl, Glu/Dab, Glu/Dap, Glu/DDap, and Glu/Lys, and $R_1$ is Ac or Bz, or wherein $X_1$ and $X_7$ are, respectively, a pair selected from the group consisting of succinyl/(D/L)Agl, succinyl/Dab, succinyl/Dap, succinyl/Lys, and succinyl/Orn, and $R_1$ is absent; or c) said lactam is formed by an amide bond between the α-amino group of $X_1$ and the side chain carboxyl group of $X_7$, wherein $X_1$ and $X_7$ are, respectively, a pair selected from the group consisting of Ala/Glu, Ala/DGlu, DAla/DGlu, Dap(Ac)/Glu, Gly/Asp, Gly/Glu, Gly/DGlu, Leu/Glu, Leu/DGlu, Lys/DGlu, Lys(Ac)/Glu, 2Nal/Glu, Phe/Glu, Phe/DGlu, DPhe/Glu, and DPhe/DGlu, and $R_1$ is absent; or d) said lactam is formed by an amide bond between a non-α, non-side-chain amino group of $X_1$ and the side chain carboxyl group of $X_7$, wherein $X_1$ and $X_7$ are, respectively, a pair selected from the group consisting of β-Ala/Asp, β-Ala/Glu, 5-amino-valeryl/Asp, 5-aminovaleryl/Glu, 4-AMB/Glu, 4-AMPA/Asp, and 4-AMPA/Glu, and $R_1$ is absent; or e) said lactam is formed by an amide bond between the α-amino group of $X_2$ and the side chain carboxyl group of $X_7$, wherein $X_2$ and $X_7$ are, respectively, a pair selected from the group consisting of Tyr/Asp, Tyr/Glu, and Tyr/DGlu, and $R_1$ and $X_1$ are each absent;

$R_1$ is a substituent on the α-amino group of $X_1$ when $X_1$ contains an α-amino group and said α-amino group is not a constituent of said lactam amide bond, selected from the group consisting of Ac, Bz, and n-hexanoyl, or is absent, wherein $X_1$ is selected from the group consisting of (D/L)Agl, Asp, Dab, Dap, and Glu;

$X_1$ is selected from the group consisting of (D/L)Agl, Ala, β-Ala, DAla, 5-aminovaleryl, 4-AMB, 4-AMPA, Asp, Dab, Dap, Dap(Ac), Glu, Gly, Leu, Lys, Lys(Ac), 2Nal, Phe, DPhe, and succinyl, or is absent;

$X_3$ is selected from the group consisting of Arg, Lys, Lys(iPr), and Lys($Me_2$);

$X_7$ is selected from the group consisting of(D/L)Agl, Asp, Dab, Dap, DDap, Glu, DGlu, Lys, and Orn;

$X_8$ is selected from the group consisting of β-Ala, Arg, DArg, Gly, Lys, Lys(iPr), and Orn, or is absent;

$X_9$ is selected from the group consisting of Gly, 2Nal, D2Nal, and DPhe, or is absent;

$X_{10}$ is 2Nal, or is absent;

wherein when $X_8$ is absent, $X_9$ and $X_{10}$ are each absent, and when $X_9$ is absent, $X_{10}$ is absent, and $R_2$ is selected from the group consisting of $NH_2$ and NHEt, or a pharmaceutically acceptable salt thereof.

2. The lactam-cyclized peptide or pharmaceutically acceptable salt thereof of claim 1, wherein:

$R_1$ is selected from the group consisting of Ac and Bz, or is absent;

$X_1$ is selected from the group consisting of β-Ala, 4-AMB, 4-AMPA, Asp, Dab, Dap, Dap(Ac), Glu, 2Nal, Phe, and succinyl, or is absent;

$X_3$ is selected from the group consisting of Arg, Lys, Lys (iPr), and Lys($Me_2$);

$X_7$ is selected from the group consisting of Asp, Dab, Dap, Glu, DGlu, Lys, and Orn;

$X_8$ is selected from the group consisting of Arg and Lys, or is absent;

$X_9$ is absent;

$X_{10}$ is absent; and $R_2$ is selected from the group consisting of $NH_2$ and NHEt.

3. The lactam-cyclized peptide or pharmaceutically acceptable salt thereof of claim 1, wherein:

$R_1$ is selected from the group consisting of Ac and Bz, or is absent;

$X_1$ is selected from the group consisting of DAla, 5-aminovaleryl, 4-AMPA, Asp, Glu, Leu, Lys(Ac), Phe, DPhe, and succinyl;

$X_3$ is selected from the group consisting of Arg, Lys, Lys (iPr), and Lys($Me_2$);

$X_7$ is selected from the group consisting of (D/L)Agl, Asp, Dab, Dap, DDap, Glu, and DGlu;

$X_8$ is selected from the group consisting of Arg, DArg, and Lys, or is absent;

$X_9$ is absent;

$X_{10}$ is absent; and $R_2$ is selected from the group consisting of $NH_2$ and NHEt.

4. The lactam-cyclized peptide or pharmaceutically acceptable salt thereof of claim 1, wherein:

$R_1$ is selected from the group consisting of Ac, Bz, and n-hexanoyl, or is absent;

$X_1$ is selected from the group consisting of (D/L)Agl, Ala, β-Ala, Asp, Dap, Glu, Gly, Lys, and Phe;

$X_3$ is selected from the group consisting of Arg, Lys, Lys (iPr), and Lys($Me_2$);

$X_7$ is selected from the group consisting of (D/L)Agl, Asp, Dap, Glu, and DGlu;

$X_8$ is selected from the group consisting of β-Ala, Arg, Gly, Lys, Lys(iPr), and Orn, or is absent;

$X_9$ is selected from the group consisting of Gly, 2Nal, D2Nal, and DPhe, or is absent;

$X_{10}$ is 2Nal, or is absent; and $R_2$ is selected from the group consisting of $NH_2$ and NHEt.

5. The lactam-cyclized peptide or pharmaceutically acceptable salt thereof of claim 1, wherein:

$R_1$ is selected from the group consisting of Ac and Bz, or is absent;

$X_1$ is selected from the group consisting of Ala, 5-aminovaleryl, Asp, Glu, Gly, Phe, DPhe, and succinyl;

$X_3$ is selected from the group consisting of Arg, Lys(iPr), and Lys($Me_2$);

$X_7$ is selected from the group consisting of (D/L)Agl, Asp, Dap, Glu, and DGlu;

$X_8$ is selected from the group consisting of β-Ala, Arg, Gly, Lys, Lys(iPr), and Orn, or is absent;

$X_9$ is selected from the group consisting of Gly, D2Nal, and DPhe, or is absent;

$X_{10}$ is 2Nal, or is absent; and $R_2$ is selected from the group consisting of $NH_2$ and NHEt.

6. The lactam-cyclized peptide or pharmaceutically acceptable salt thereof of claim 1, wherein:

$X_1$ is selected from the group consisting of Gly and Phe;

$X_3$ is Lys(iPr); and $X_7$ is DGlu.

7. The lactam-cyclized peptide or pharmaceutically acceptable salt thereof of claim 5, wherein:

$R_1$ is absent;

$X_1$ is selected from the group consisting of Gly and Phe;

$X_3$ is Lys(iPr);

$X_7$ is DGlu;

$X_8$ is selected from the group consisting of Arg and Lys (iPr), or is absent;

$X_9$ is absent;

$X_{10}$ is absent; and $R_2$ is selected from the group consisting of $NH_2$ and NHEt.

8. A lactam-cyclized peptide of the formula:

(SEQ ID NO: 70)

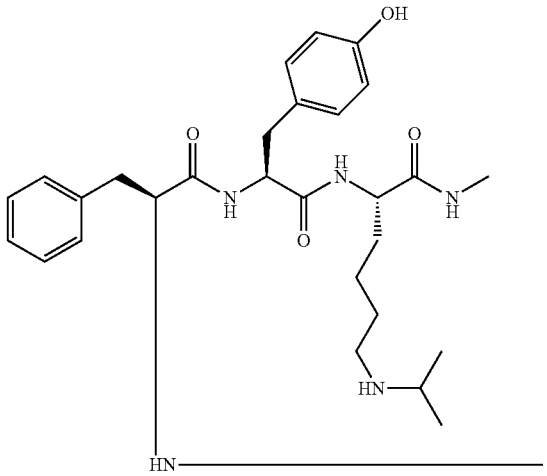

-continued

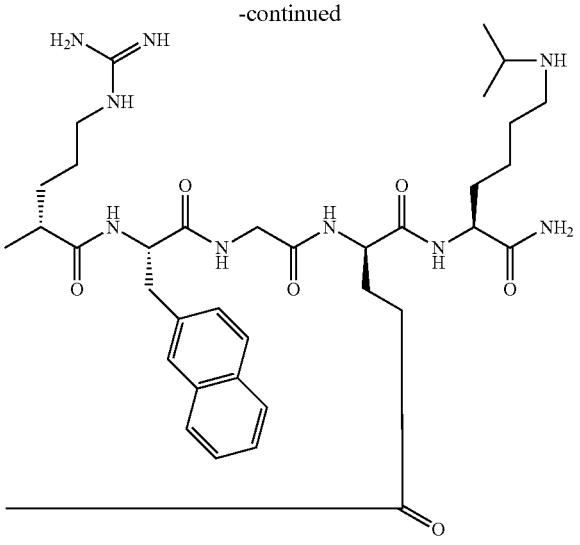

or a pharmaceutically acceptable salt thereof.

9. The lactam-cyclized peptide of claim 8, wherein said pharmaceutically acceptable salt is an acetic acid salt.

10. A pharmaceutical composition, comprising a lactam-cyclized peptide or pharmaceutically acceptable salt thereof of claim 1, and a pharmaceutically acceptable carrier, diluent, or excipient.

11. A pharmaceutical composition, comprising said acetic acid salt of said lactam-cyclized peptide of claim 9, and a pharmaceutically acceptable carrier, diluent, or excipient.

12. A method of treating rheumatoid arthritis, pulmonary fibrosis, HIV infection, or a cancer selected from the group consisting of breast cancer, pancreatic cancer, melanoma, prostate cancer, kidney cancer, neuroblastoma, non-Hodgkin's lymphoma, lung cancer, ovarian cancer, colorectal cancer, multiple myeloma, glioblastoma multiforme, and chronic lymphocytic leukemia, comprising administering to a patient in need thereof an effective amount of a lactam-cyclized peptide or pharmaceutically acceptable salt thereof of claim 1.

13. A method of treating rheumatoid arthritis, pulmonary fibrosis, HIV infection, or a cancer selected from the group consisting of breast cancer, pancreatic cancer, melanoma, prostate cancer, kidney cancer, neuroblastoma, non-Hodgkin's lymphoma, lung cancer, ovarian cancer, colorectal cancer, multiple myeloma, glioblastoma multiforme, and chronic lymphocytic leukemia, comprising administering to a patient in need thereof an effective amount of said lactam-cyclized peptide or pharmaceutically acceptable salt thereof of claim 8.

14. The method of claim 13, wherein said pharmaceutically acceptable salt of said lactam-cyclized peptide is an acetic acid salt.

* * * * *

UNITED STATES PATENT AND TRADEMARK OFFICE

CERTIFICATE OF CORRECTION

PATENT NO. : RE42,274 E
APPLICATION NO. : 12/807694
DATED : April 5, 2011
INVENTOR(S) : Wayne David Kohn It is certified that error appears in the above-identified patent and that said Letters Patent is hereby corrected as shown below:

In the issued patent, please note the following corrections:

In Claim 1, Column 166, Line 52, after "Ala/DGlu," insert --DAla/Glu--

Signed and Sealed this
Fourteenth Day of June, 2011

David J. Kappos

David J. Kappos
*Director of the United States Patent and Trademark Office*